US008007805B2

(12) United States Patent
George et al.

(10) Patent No.: US 8,007,805 B2
(45) **Date of Patent: *Aug. 30, 2011**

(54) CHIMERIC ANTIGENS FOR BREAKING HOST TOLERANCE TO FOREIGN ANTIGENS

(75) Inventors: Rajan George, Edmonton (CA); Lorne Tyrrell, Edmonton (CA); Antoine Noujaim, Edmonton (CA); Dakun Wang, Edmonton (CA); Allan Ma, Edmonton (CA)

(73) Assignee: Paladin Labs, Inc. (CA)

(*) Notice: Subject to any disclaimer, the term of this patent is extended or adjusted under 35 U.S.C. 154(b) by 0 days.

This patent is subject to a terminal disclaimer.

(21) Appl. No.: 10/913,171

(22) Filed: Aug. 5, 2004

(65) Prior Publication Data

US 2005/0031628 A1 Feb. 10, 2005

Related U.S. Application Data

(60) Provisional application No. 60/493,449, filed on Aug. 8, 2003.

(51) Int. Cl.
*A61K 39/29* (2006.01)
*C12P 21/00* (2006.01)

(52) U.S. Cl. .................................. 424/178.1; 424/227.1

(58) Field of Classification Search ........................ None
See application file for complete search history.

(56) References Cited

U.S. PATENT DOCUMENTS

| | | | |
|---|---|---|---|
| 4,088,748 | A | 5/1978 | McAleer et al. |
| 4,181,713 | A | 1/1980 | McAleer et al. |
| 4,235,871 | A | 11/1980 | Papahadjopoulos et al. |
| 4,428,941 | A | 1/1984 | Galibert et al. |
| 4,433,059 | A | 2/1984 | Chang et al. |
| 4,501,728 | A | 2/1985 | Geho et al. |
| 4,569,794 | A | 2/1986 | Smith et al. |
| 4,599,230 | A | 7/1986 | Milich et al. |
| 4,599,231 | A | 7/1986 | Milich et al. |
| 4,722,840 | A | 2/1988 | Valenzuela et al. |
| 4,816,249 | A | 3/1989 | Levy et al. |
| 4,816,567 | A | 3/1989 | Cabilly et al. |
| 4,837,028 | A | 6/1989 | Allen |
| 4,877,830 | A | 10/1989 | Dobeli et al. |
| 5,019,369 | A | 5/1991 | Presant et al. |
| 5,023,252 | A | 6/1991 | Hseih |
| 5,047,513 | A | 9/1991 | Dobeli et al. |
| 5,053,224 | A | 10/1991 | Koprowski et al. |
| 5,098,833 | A | 3/1992 | Lasky et al. |
| 5,116,964 | A | 5/1992 | Capon et al. |
| 5,155,027 | A | 10/1992 | Sledziewski et al. |
| 5,196,194 | A | 3/1993 | Rutter et al. |
| 5,216,131 | A | 6/1993 | Lasky et al. |
| 5,225,538 | A | 7/1993 | Capon et al. |
| 5,284,933 | A | 2/1994 | Dobeli et al. |
| 5,310,663 | A | 5/1994 | Dobeli et al. |
| 5,336,603 | A | 8/1994 | Capon et al. |
| 5,346,994 | A | 9/1994 | Chomczynski |
| 5,420,264 | A | 5/1995 | Seed et al. |
| 5,428,130 | A | 6/1995 | Capon et al. |
| 5,455,030 | A | 10/1995 | Ladner et al. |
| 5,455,165 | A | 10/1995 | Capon et al. |
| 5,514,582 | A | 5/1996 | Capon et al. |
| 5,565,335 | A | 10/1996 | Capon et al. |
| 5,567,584 | A | 10/1996 | Sledziewski et al. |
| 5,589,466 | A | 12/1996 | Felgner et al. |
| 5,686,600 | A | 11/1997 | Carozzi et al. |
| 5,715,147 | A | 2/1998 | Nagano |
| 5,750,375 | A | 5/1998 | Sledziewski et al. |
| 5,792,463 | A | 8/1998 | Valenzuela et al. |
| 5,840,844 | A | 11/1998 | Lasky et al. |
| 5,843,725 | A | 12/1998 | Sledziewski et al. |
| 5,928,902 | A | 7/1999 | De Wilde et al. |
| 5,942,234 | A | 8/1999 | Ralston et al. |
| 5,965,140 | A | 10/1999 | Valenzuela et al. |
| 5,969,109 | A | 10/1999 | Bona et al. |
| 5,977,315 | A | 11/1999 | Chatterjee et al. |
| 6,004,781 | A | 12/1999 | Seed |
| 6,018,026 | A | 1/2000 | Sledziewski et al. |
| 6,074,846 | A | 6/2000 | Ralston et al. |
| 6,074,852 | A | 6/2000 | Ralston et al. |
| 6,086,873 | A | 7/2000 | Sykes et al. |
| 6,087,476 | A | 7/2000 | Kenten et al. |
| 6,117,655 | A | 9/2000 | Capon et al. |

(Continued)

FOREIGN PATENT DOCUMENTS

WO WO 92/01470 2/1992

(Continued)

OTHER PUBLICATIONS

You et al., Targeting Dendritic Cells to Enhance DNA Vaccine Potency, Cancer Research, May 1, 2001, vol. 61, pp. 3704-3711.*
Loirat et al., Multiepitopic HLA-A 0201-Restricted Immune Response Against Hepatitis B Surface Antigen After DNA-Based Immunization, The Journal of Immunology, 2000, vol. 165, pp. 4748-4755.*
Eyles et al. Journal of Controlled Release, 2003, vol. 86, pp. 25-32.*
Lutsiak et al. Pharmaceutical Research, Oct. 2002, vol. 19, No. 10, pp. 1480-1487, see 2 page summary.*
Baumert et al. Journal of Virology, 1998, vol. 72, No. 5, pp. 3827-3836.*
Altman, et al., "Insect Cells as Hosts for the Expression of Recombinant Glycoproteins." *Glycoconjugate Journal* 16: 109-123 (1999).

(Continued)

*Primary Examiner* — Bao Li
(74) *Attorney, Agent, or Firm* — Sheridan Ross P.C.

(57) ABSTRACT

Disclosed herein are compositions and methods for eliciting immune responses against antigens. In particular, the compounds and methods elicit immune responses against foreign antigens that are otherwise recognized by the host as "self" antigens, thus breaking host tolerance to those antigens. Presenting the host immune system with a chimeric antigen comprising an immune response domain and a target binding domain, wherein the target binding domain comprises an antibody fragment, enhances the immune response against the foreign or tolerated antigen. Antigen presenting cells take up, process, and present the chimeric antigen, eliciting both a humoral and cellular immune response against the desired antigen.

29 Claims, 5 Drawing Sheets

U.S. PATENT DOCUMENTS

Figure 1A:
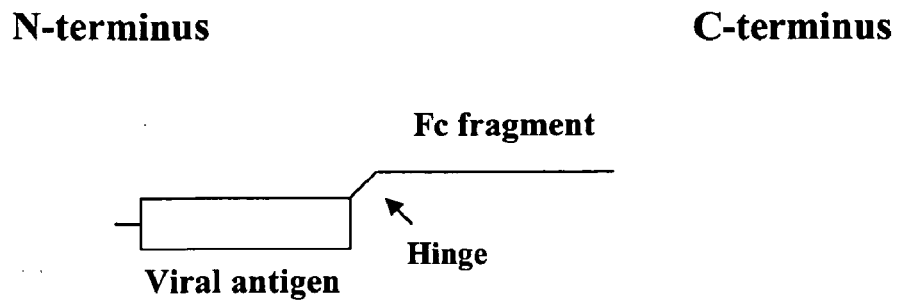

| | | |
|---|---|---|
| 6,207,153 B1 | 3/2001 | Dan et al. |
| 6,241,985 B1 | 6/2001 | Madiyalakan et al. |
| 6,242,195 B1 | 6/2001 | Idusogie et al. |
| 6,274,148 B1 | 8/2001 | Ralston et al. |
| 6,277,375 B1 | 8/2001 | Ward |
| 6,291,212 B1 | 9/2001 | Sledziewski et al. |
| 6,291,646 B1 | 9/2001 | Sledziewski et al. |
| 6,300,099 B1 | 10/2001 | Sledziewski et al. |
| 6,323,323 B1 | 11/2001 | Sledziewski et al. |
| 6,406,697 B1 | 6/2002 | Capon et al. |
| 6,500,641 B1 | 12/2002 | Chen et al. |
| 6,521,423 B1 | 2/2003 | Houghton et al. |
| 6,555,114 B1 | 4/2003 | Leroux-Roels et al. |
| 6,613,333 B1 | 9/2003 | Leroux-Roels et al. |
| 6,689,355 B2 | 2/2004 | Schultes et al. |
| 6,710,169 B2 | 3/2004 | Capon et al. |
| 6,716,623 B2 | 4/2004 | Chen et al. |
| 6,716,966 B1 | 4/2004 | Madiyalakan |
| 6,808,901 B1 | 10/2004 | Neuberger et al. |
| 6,838,281 B2 | 1/2005 | Scott et al. |
| 7,067,110 B1 * | 6/2006 | Gillies et al. ............. 424/1.49 |
| 2001/0044135 A1 | 11/2001 | Stahl et al. |
| 2001/0048922 A1 | 12/2001 | Romet-Lemonne et al. |
| 2002/0004048 A1 | 1/2002 | Ralston et al. |
| 2002/0048583 A1 | 4/2002 | Schultes et al. |
| 2003/0118592 A1 * | 6/2003 | Ledbetter et al. ......... 424/178.1 |
| 2003/0149254 A1 * | 8/2003 | Anderson et al. ............ 536/23.1 |
| 2003/0235536 A1 | 12/2003 | Blumberg et al. |
| 2004/0001854 A1 | 1/2004 | Houghton et al. |
| 2004/0047877 A1 | 3/2004 | Leroux-Roels et al. |
| 2004/0063912 A1 | 4/2004 | Blumberg et al. |
| 2004/0096426 A1 | 5/2004 | Chen et al. |
| 2005/0089843 A1 | 4/2005 | Ralston et al. |
| 2005/0186662 A1 | 8/2005 | Low |
| 2009/0238822 A1 | 9/2009 | George et al. |

FOREIGN PATENT DOCUMENTS

| | | |
|---|---|---|
| WO | 92/05793 | 4/1992 |
| WO | WO 96/01650 | 1/1996 |
| WO | 96/08570 | 3/1996 |
| WO | WO 96/40941 | 12/1996 |
| WO | 97/07218 | 2/1997 |
| WO | WO 97/36932 | 10/1997 |
| WO | 98/20141 | 5/1998 |
| WO | 99/65517 | 12/1999 |
| WO | 00/20460 | 4/2000 |
| WO | WO 00/20460 | 4/2000 |
| WO | 01/07081 | 2/2001 |
| WO | WO 01/07081 | 2/2001 |
| WO | 01/32893 | 5/2001 |
| WO | WO 01/32714 | 5/2001 |
| WO | WO 01/77137 A1 * | 8/2001 |
| WO | 01/85203 | 11/2001 |
| WO | WO 02/04484 | 1/2002 |
| WO | WO 02/056830 | 7/2002 |
| WO | 2004/004798 | 1/2004 |
| WO | 2004/100882 | 11/2004 |
| WO | 2004/101740 | 11/2004 |
| WO | 2004/108885 | 12/2004 |
| WO | 2005/001025 | 1/2005 |
| WO | WO 2005/014838 | 2/2005 |
| WO | 2005/073383 | 8/2005 |
| WO | WO 2005/087813 | 9/2005 |

OTHER PUBLICATIONS

Apostolopoulos et al., "Aldehyde-mannan antigen complexes target the MHC class I antigen-presentation pathway." *Eur. J. Immunol.* 30:1714-1723 (2000).

Apostolopoulos and McKenzie, "Role of the mannose receptor in the immune response," *Curr. Mol. Med.* 1:469-474 (2001).

Ashkenazi et al., "Immunoadhesins as research tools and therapeutic agents", *Curr. Op Immunol.* 9: 195-200, (1997).

Banchereau, and Steinman "Dendritic cells and the control of immunity," *Nature* 392: 245-252 (1998).

Bartenschlager et al., "Novel Insights into Hepatitis C Virus Replication and Persistence", *Advances in Virus Research* 63: 71-180 (2004).

Beasley, "Hepatitis B Virus. The major etiology of hepatocellular carcinoma," *Cancer* 61(10): 1942-1956, (1988).

Berlyn, et al., "Generation of CD4(+) and CD8(+) T lymphocyte responses by dendritic cells armed with PSA/anti-PSA (antigen/antibody) complexes," *Clin. Immunol.*, 101(3):276-283 (2001).

Bonini et al., "Targeting antigen in mature dendritic cells for simultaneous stimulation of CD4+ and CD8+ T cells", *Journal Immunology* 166: 5250-5257, (2001).

Campton, et al. "Tumor antigen presentation by dermal antigen-presenting cells", *J. Invest. Dermatol.* 115: 57-61 (2000).

Chamow et al., Immunoadshesins: principles and applications, *Tibtech* 14: 52-59 (1996).

Chapman-Smith et al., "The enzyme biotinylation of proteins: a post-translational modification of exceptional specificity", *TIBS*, 24: 359-363 (1999).

Clarke, "Molecular virology of hepatitis C virus" *J. Gen. Virol.* 78: 2397-2410 (1997).

Coughlan et al. "Enhanced proliferation of CD4+ T cells induced by dendritic cells following antigen uptake in the presence of specific antibody", *Vetrinary Immunology and Immunopathology* 49: 321-330, 1996.

Deres, et al., "In vivo priming of virus-specific cytotoxic T lymphocytes with synthetic lipopeptide vaccine," *Nature* 342: 561-564 (1989).

Donnelly, et al. "DNA vaccines." *Annu. Rev. Immunol.* 15: 617-648 (1997).

Dwyer, M.A. et al., "Expression and characterization of a Dnase I-Fc fusion enzyme", *Journal of Biological Chemistry*: 274(14): 9738-9743 (1999).

Fanger, N.A. "Characterization of expression, cytokine regulation, and effector function of the high affinity IgG receptor FcγRI(CD64) expressed on human blood dendritic cells", *Journal of Immunology* 158: 3090-3098 (1997).

Fanger et al., "Type I (CD64) and Type II (CD32) Fcγ receptor-mediated phagocytosis by human blood dendritic cells", *Journal of Immunology* 157: 541-548 (1996).

Feng, Z-H et al., "Construction and expression of chrimeid plasmid pHCV-IgFc", Elsevier Science Publishers and World Chinese Journal of Digestology, 11:6, pp. 697-700, Jun. 1, 2003, Database Embase ' Online!, Database accession No. EMB-2003261340.

Ferlazzo et al., "Dendritic cells generated either from CD34+ progenitor cells or from monocytes differ in their ability to activate antigen-specific CD8+ T cells", *Journal of Immunology* 163: 3597-3604 (1999).

Finkleman et al., "Dendritic cells can present antigen in vivo in a tolerogenic or immunogenic fashion", *Journal of Immunology* 157: 1406-1414 (1996).

Fong and Engleman "Dendritic cells in cancer immunotherapy." *Annu. Rev. Immunol.* 18: 245-273 (2000).

Fried et al., "Peginterferon alfa-2a plus ribavirin for chronic hepatitis C virus infection." *N. Engl. J. Med.* 347(13): 975-982 (2002).

Ganem, "Perspectives: Virology: The X files—one step closer to closure." *Science* 294: 2299-2300 (2001).

Grohmann et al., "CD40 litigation ablates the tolerogenic potential of lymphoid dendritic cells", *Journal of Immunology* 166: 277-283 (2001).

Guermonprez et al., "Antigen presentation and T cell stimulation by dendritic cells", *Annual Review Immunology* 20: 621-667 (2002).

Gust, et al., "Taxonomic classification of human hepatitis B virus," *Intervirology* 25:14-29 (1986).

Hartgers et al., "Toward a molecular understanding of dendritic cell immunobiology", *Immunology Today* 21(11): 542-545 (2000).

Hellström et al., "Significance of Pre-S2 Peptide of Hepatitis B Virus: Should it be in the Vaccine?", *Prog. Med. Virol.* 35: 76-106 (1998).

Henikoff and Henikoff, "Amino acid substitution matrices from protein blocks," *PNAS* 89:10915-10919 (1992).

Hilgers, et al. "Sulfolipo-cyclodextrin in squalane-in-water as a novel and safe vaccine adjuvant." *Vaccine* 17: 219-228 (1999).

Hochrein et al., "Differential production of IL-12, IFN-α and IFN-γ by mouse dendritic cell subsets", *Journal of Immunology* 166: 5448-5455 (2001).

Jenne et al., "Viral vectors for dendritic cell-based immunotherapy", *Trends in Immunology* 22(2): 102-107 (2001).

Jonuleit et al., "Dendritic cells as a tool to induce anergic and regulatory T cells", *Trends in Immunology* 22(7): 394-400 (2001).

Kane, "Global programme for control of hepatitis B infection", *Vaccine* 13(Supplement 1): S47-S49 (1995).

Kotenko et al. "Identification of the Functional Interleukin-22 (IL-22) Receptor Complex", *Journal of Biological Chemistry* 276(4): 2725-2732 (2002).

Kozak, "Adherence to the first-AUG rule when a second AUG codon follows closely upon the first," *PNAS* 92: 2662-2666 (1995).

Kozak, "An analysis of 5'-noncoding sequences from 699 vertebrate messenger RNAs," *NAR* 15(20): 8125-8132 (1987).

Kozak, "Context Effects and Inefficient Initiation at Non-AUG Codons in Eucaryotic Cell-Free Translation Systems," *Mol. Cell. Biol.*, 9(11): 5073-5080 (1989).

Lai and Bennett "DNA vaccines." *Crit. Rev. Immunol.* 18: 449-484 (1998).

Larsson, et al. "Dendritic cells resurrect antigens from dead cells." *Trends Immunol.* 22(3): 141-148 (2001).

Lauer and Walker, "Medical Progress: Hepatitis C Virus Infection", *N. Engl. J. Med.* 345(1):41-52 (2001).

Laupéze, et al. "Differential expression of major histocompatibility complex class Ia, Ib, and II molecules on monocytes and monocyte-derived dendritic and macrophagic cells." *Hum. Immunol.* 60: 591-597 (1999).

Lei et al., "Structure-function analysis of human glucose-6-phosphatase, the enzyme deficient in glycogen storage disease type 1a," *J. Biol. Chem.* 270(20):11882-11886 (1995).

Lorenz et al., "Induction of Ani-Tumor Immunity Elicited yb Tumor Cells Expressing a Murine LFA-3 Analog via a Recombinant Vaccinia virus", *Hum. Gene Ther.* 10: 623-631 (1999).

Lorenz, et al. "Anti-tumor immunity elicited by a recombinant vaccinia virus expressing CD70 (CD27L)."*Hum. Gene Ther.* 10: 1095-103 (1999).

Manns, et al., "Peginterferon alfa-2b plus ribavirin compared with interferon alfa-2b plus ribavirin for initial treatment of chronic hepatitis C: a randomised trial," *Lancet* 358:958-965 (2001).

Marion "Use of animal models to study hepatitis B virus."*Prog. Med. Virol.* 35:43-75 (1988).

Mason, et al. "Virus of Pekin Ducks with Structural and Biological Relatedness to Human Hepatitis B Virus." *J. Virol.* 36(3): 829-36 (1980).

Merad et al., "Differentiation of myeloid dendritic cells into CD8α-positive", *Blood* 96(5): 1865-1872 (2000).

Moore et al., "Interleukin-10 and the interleukin-10 receptor", *Annual Review Immunology* 19: 683-765 (2001).

Nagarajan et al., "Ligand binding and phagocytosis by CD16 (Fcγ receptor III) isoforms", *Journal of Biological Chemistry* 270(43): 25672-25770 (1995).

Neuhaus et al., "Multiple sclerosis: comparison of copolymer-1-reactive T cell lines from treated and untreated subjects reveals cytokine shift from T helper 1 to T helper 2 cells", *PNAS* 97(13): 7452-7457 (2000).

Newman, et al. "Uptake of poly(D,L-lactic-*co*-glycolic acid) microspheres by antigen-presenting cells in vivo," *J. Biomed Mater Res.* 603: 480-486 (2002).

Newman, et al. "Ovalbumin peptide encapsulated in poly(*d,l* lactic-co-glycolic acid) microspheres is capable of inducing a T helper type 1 immune response." *J. Control Release* 54: 49-59 (1998).

Newman, et al. "Cytoplasmic delivery of a macromolecular fluorescent probe by poly(*d, l*-lactic-co-glycolic acid) microspheres." *J. Biomed Mater Res.* 50: 591-597 (2000).

Novak et al., "Engagement of FcεRI on human monocytes induces the production of IL-10 and prevents their differnetation in dendritic cells", *Journal of Immunology* 167: 797-804 (2001).

Qin et al. "Fcγ receptor IIb on follicular dendritic cells regulates the B cell recall response", *Journal of Immunology* 164: 6268-6275 (2000).

Quarantino et al., "Fully competent dendritic cells as inducers of T cell anergy in autoimmunity", *PNAS* 97(20): 10911-10916 (2000).

Ramakrishna et al., "Mannose receptor targeting of tumor antigen pmel17 to human dendritic cells directs anti-melanoma T cell responses via multiple HLA molecules," *J. Immunol.* 172: 2845-2852 (2004).

Regnault et al., "Fcγ receptor-mediated induction of dendritic cell maturation and major histocompatibility complex Class 1-restricted antigen presentation after immune complex internalization", *Journal Exp. Medicine* 189(2): 371-380, (1999).

Roncarolo et al., "Differentation of T regulatory cells by immature dendritic cells", *Journal Exp. Medicine* 193(2): F5-F9 (2001).

Saito et. al., "Hepatitis C virus infection is associated with the development of hepatocellular carcinoma" *PNAS USA* 87: 6547-6549 (1990).

Schultz et al., "Duck Hepatitis B Virus: An Invaluable Model System for HBV Infection", *Advances in Virus Research* 63: 1-70 (2004).

Schuurhuis et al., "Antigen-antibody immune complexes empower dendritic cells to efficiently prime specific CD8+ CTL responses in vivo", *Journal of Immunology* 168: 2240-2246, (2002).

Sprengel, et al. "Isolation and characterization of a hepatitis B virus endemic in herons." *J. of Virol.* 62(10): 3832-3839 (1988).

Steinman, et al. "Antigen capture, processing, and presentation by dendritic cells: recent cell biological studies." *Hum. Immunol.* 60(7): 562-567 (1999).

Summers, , et al. "A virus similar to human hepatitis B virus associated with hepatitis and hepatoma in woodchucks." *Proc. Natl. Acad. Sci. USA* 75(9): 4533-7 (1978).

Szoka, et al., "Comparative properties and methods of preparation of lipid vesicles (liposomes),"*Ann. Rev. Biophys. Bioeng.* 9:467-508 (1980).

Tan and Katze, "How hepatitis C virus counteracts the interferon response: the jury is still out on NS5A" *Virology* 284: 1-12 (2001).

Whitton et al., "The Regulation and Maturation of Antiviral Immune Responses", *Advances in Virus Research*, 63: 181-238 (2004).

You, Z. et al., "Targeting dentritic cells to enhance DNA vaccine potency", *Cancer Research*, vol. 61, pp. 3704-3711, (2001).

You, Z. et al., "Induction of vigorous helper and cytotoxic T cell as well as B cell responses by dentritic cells expressing a modified antigen targeting receptor-mediated internalization pathway", *Journal of Immunology*, 165:8, pp. 4581-4591, Oct. 15, 2001.

Zhu et al., "MHC class 1-related neonatal Fc receptor for IgG is functionally expressed in monocytes, intestinal macrophages, and dendritic cells", *Journal of Immunology* 166: 3266-3276, (2001).

Zuckerman, "More than third of world's population has been infected with hepatitis B virus", *BMJ* 318(7192): 1213 (1999).

He et al, "A novel human cancer vaccine elicits cellular responses to the tumor-associated antigen, human chorionic gonadotropin" *Clin Cancer Res.* 10(6): 1920-1927, (2004).

Motyka et al., "CD8+ T Cell Responses to a Novel Class of Therapeutic Vaccines for the Treatment of Chronic Hepatitis B Infection", Abstract No. 2481, 12th International Congress of Immunology and 4th Annual Conference of FOCIS, [online] Jul. 18-23, 2004 [retrieved Nov. 19, 2004] retrieved from the Internet URL: http://www.immuno2004.org/onlineabstracts/index.html.

Stevenson et al., "Vaccine therapy in NGL: Future Promises and Current Limitations", *Leuk Lymphoma* 44 Suppl 3: S85-90 (2003).

Wang et al., "Characterization of Immne Resp;onses of a Novel Therapeutic Vaccine for the Treatment of Chronic Heaptitis B Virus Infections", Abstract No. 2293, 12th International Congress of Immunology and 4th Annual Conference of FOCIS,(2004), [online] Jul. 18-23, 2004 [retrieved Nov. 19, 2004] retrieved from the Internet URL: http://www.immuno2004.org/onlineabstracts/index.html.

You, Z., et al., "A retrogen strategy for presentation of an intracellular tumor antigen as an exogenous antigen by dendritic cells induces potent antitumor T helper and CTL responses", *Cancer Research*, 61(1): 197-205 (2001).

Adema et al., "Migration of dendritic cell based cancer vaccines: in vivo veritas?," Current Opinion in Immunology 2005, 17:1-5.

Arribillaga et al., "Enhancement of CD4 and CD8 immunity by anti-CD137 (4-1BB) monoclonal antibodies during hepatitis C vaccination with recombinant adenovirus," Vaccine 23 (2005) 3493-3499.

Barth et al., "Uptake and presentation of hepatitis C virus-like particles by human dendritic cells," Blood, May 1, 2005, vol. 105, No. 9, pp. 3605-3614.

Berzofsky et al., "Progress on new vaccine strategies against chronic viral infections," The Journal of Clinical Investigation, vol. 114, No. 4, Aug. 2004, pp. 450-462.

Boruchov et al., "Activating and inhibitory IgG Fc receptors on human DCs mediate opposing functions," The Journal of Clinical Investigation, vol. 115, No. 10, Oct. 2005, pp. 2914-2923.

Chisari, "Unscrambling hepatitis C virus-host interactions," Nature, vol. 436, Aug. 18, 2005, pp. 930-932.

Encke et al., "Prophylactic and therapeutic vaccination with dendritic cells against hepatitis C virus infection," 2005 British Society for Immunology, Clinical and Experimental Immunology, 142: 362-369.

Faith et al., "Targeting the dendritic cell: the key to immunotherapy in cancer?", 2005 British Society for Immunology, Clinical and Experimental Immunology, 139: 395-397.

Foumillier et al., "Primary and memory T cell responses induced by hepatitis C virus multiepitope long peptides," Vaccine 24 (2006) 3153-3164.

Houghton et al., "Prospects for a vaccine against the hepatitis C virus," Nature, vol. 436, Aug. 18, 2005, pp. 961-966.

Jefferis, "Glycosylation of Recombinant Antibody Therapeutics," Biotechnol. Prog. 2005, 21, 11-16.

Langhans et al., "Cytotoxic Capacity of Hepatitis C Virus (HCV)-Specific Lymphocytes After In Vitro Immunization with HCV-Derived Lipopeptides," Cytometry Part A 65A: 59-68 (2005).

Leyssen et al., "Perspectives for the Treatment of Infections with Flaviviridae," Clinical Microbiology Reviews, Jan. 2000, pp. 67-82, vol. 13, No. 1.

Li et al., "A novel HBV DNA vaccine based on T cell epitopes and its potential therapeutic effect in HBV transgenic mice," International Immunology, vol. 17, No. 10, pp. 1293-1302.

Liang et al., "Pathogenesis, Natural History, Treatment, and Prevention of Hepatitis C," Annals of Internal Medicine, vol. 132, No. 4, Feb. 15, 2000, pp. 296-305.

McGreal et al., "Ligand recognition by antigen-presenting cell C-type lectin receptors," Current Opinion in Immunology 2005, 17: 18-24.

Michel et al., "Therapeutic vaccination against chronic hepatitis B virus infection," Journal of Clinical Virology 34 Suppl. 1 (2005) S108-S114.

Mihailova et al., "Recombinant virus-like particles as a carrier of B- and T-cell epitopes of hepatitis C virus (HCV)," Vaccine (2006) pp. 1-9.

Nestle et al., "Dendritic-cell-based therapeutic vaccination against cancer," Current Opinion in Immunology 2005, 17: 1-7.

Peng et al., "Novel vaccines for the treatment of chronic HBV infection based on mycobacterial heat shock protein 70," Vaccine 24 (2006) 887-896.

Roque et al., "Antibodies and Genetically Engineered Related Molecules: Production and Purification," Biotechnol. Prog. 2004, 20, 639-654.

Taylor et al., "The mannose receptor: linking homeostasis and immunity through sugar recognition," Trends in Immunology, vol. 26, No. 2, Feb. 2005, pp. 104-110.

Wang et al., "Induction of hepatitis C virus-specific cytotoxic T and B cell responses by dendritic cells expressing a modified antigen targeting receptor," World J Gatroenterol 2005, 11(4) 557-560.

Xu et al., "Endoplasmic reticulum targeting sequence enhances HBV-specific cytotoxic T lymphocytes induced by a CTL epitope-based DNA vaccine," Virology 334 (2005) 255-263.

Zou, "Regulatory T cells, tumour immunity and immunotherapy," Nature Reviews, Immunology, vol. 6, Apr. 2006, pp. 295-307.

Apostolopoulos et al., "Aldehyde-mannan antigen complexes target the MHC class I antigen-presentation pathway", Eur. J. Immunol., 2000, 30(6):1714-1723.

You et al, "Targeting dendritic cells to enhance DNA vaccine potency", Can. Res., 61:3704-3711 (May 2001).

"Faculty of Medicine Immunology Bookcase", Dalhousie University website, available at http://pim.medieine.dal.ealabfe.htm, pp. 1-2, published in 2005, modified on Nov. 29, 2006, printed Aug. 29, 2007.

Akiyama, et al., "Targeting apoptotic tumor cells to FcγR provides efficient and versatile vaccination against tumors by dendritic cells", J. Immunol., 2003, vol. 170, pp. 1641-1648.

Alter, et al., "The Prevalence of Hepatitis C Virus Infection in the United States, 1988 through 1994"N. Eng. J. Med., 1999, vol. 341, pp. 556-562.

Babiuk, et al., "Needle-free topical electroporation improves gene expression from plasmids administered in porcine skin", Molecular Therapy, 2003, vol. 8, pp. 992-998.

Bartenschlager, et al., "Nonstructural Protein 3 of the Hepatitis C Virus Encodes a Serine-Type Proteinase Required for Cleavage at the NS3/4 and NS4/5 Junctions", J. Virol., 1993, vol. 67, pp. 3835-3844.

Batista, et al., "The two membrane isoforms of human IgE assemble into functionally distinct B cell antigen receptors", J. Exp. Med., 1996, vol. 184, pp. 2197-2206.

Behrens, et al., "Identification and properties of the RNA-dependent RNA polymerase of Hepatitis C virus", EMBO, 1996, vol. 15, pp. 12-22.

Bouige, et al., "Molecular analysis of the modulatory factors of the response to HBsAg in mice as an approach to HBV vaccine enhancement", FEMS Immunology & Medical Microbiology, Jan. 1996, vol. 13, No. 1 p. 71-79.

Bruss, et al., "Mapping a Region of the Large Envelope Protein Required for Hepatitis B Virion Maturation", J. Virol., 1994, vol. 68, No. 3, pp. 1643-1650.

Cao, et al., "In Vivo Inhibition of Anti-Hepatitis B Virus Core Antigen (HBcAg) Immunoglobulin G Production by HBcAg-Specific CD4+ Th1-Type T-Cell Clones in a hu-PBL-NOD/SCID Mouse Model", Journal of Virology, Dec. 2001, vol. 75, No. 23, pp. 11449-11456.

Cooper, et al., "Analysis of a successful immune response against hepatitis C virus", Immunity, 1999, vol. 10, pp. 439-449.

Delwaide, et al., "Evidence-based medicine: treatment of chronic hepatitis C. Liege Study Group on Viral Hepatitis", Rev. Med. Liege, 2000, vol. 55, pp. 337-340 (Abstract).

Dodson, et al., "Prevention of de novo hepatitis B infection in recipients of hepatic allografts from anti-HBc positive donors", Transplantation, 1999, vol. 68, No. 7, pp. 1058-1061.

Dolganiuc, et al., "Hepatitis C Virus Core and Nonstructural Protein 3 Proteins Induce Pro- and Anti-inflammatory Cytokines and Inhibit Dendritic Cell Differentiation", J. Immunol., 2003, vol. 170, pp. 5615-5624.

Grakoui, et al., "HCV persistence and immune evasion in the absence of memory T cell help", Science, 2003, vol. 302, pp. 659-662.

Guyre, et al., "Colocalization of FcγRI-targeted antigen with class I MHC: implications for antigen processing", J. Immunol., 2001, vol. 166, pp. 2469-2478.

Hamann, et al., "Phenotypic and functional separation of memory and effector human CD8+ T cells", J. Exp. Med., 1997, vol. 186, p. 1407.

Hameed, et al., "Immunohistochemical identification of cytotoxic lymphocytes using human perforin monoclonal antibody" Am. J. Pathol., 1992, vol. 140, pp. 1025-1030.

Hewlett, et al., "The coated pit and macropinocytic pathways serve distinct endosome populations." J. Cell Biology, 1994, vol. 124, pp. 689-703.

Hijikkata, et al., "Gene mapping of the putative structural region of the hepatitis C virus genome by in vitro processing analysis", Proc. Natl. Acad. Sci. USA, 1991, vol. 88, pp. 5547-5551.

Ho, et al., "The likelihood of aggregation during protein renaturation can be assessed using the second viral coefficient", Prot. Sci., 2003, vol. 12, pp. 708-716.

Hoofnagle, "Course and outcome of hepatitis C", Hepatology, 2002, vol. 36, pp. S21-S29.

Jilg, et al., "Novel hepatitis B vaccines", Vaccine, 1998, vol. 16, pp. s65-s68.

Koo et al. "Construction and expression of a bifunctional single-chain antibody against Bacillus cereus p6ores." Applied and Environmental Microbiology 1998, vol. 64, No. 7, pp. 2490-2496.

Lebensztein, et al., "Current knowledge on treatment of chronic hepatitis B in children", Med. Sci. Monit., 2000, vol. 6, No. 1, pp. 198-203.

Lechner, et al., "Analysis of successful immune responses in persons infected with hepatitis C virus.", J. Exp. Med., 2000, vol. 191, pp. 1499-1522.

Lin, et al, "In vitro resistance studies of hepatitis C virus serine protease inhibitors, VX-950 and BILN 2061: structural analysis indicates different resistance 5 mechanisms", J. Biol. Chem, 2004, vol. 279, pp. 17508-17514.

Lindenbach, et al, Complete Replication of hepatitis C Virus in culture, Science, 2005, vol. 309, pp. 623-626.

Liu, et al., "Dendritic cell lineage, plasticity and cross-regulation", Nature immunology, 2001, vol. 2, No. 7, pp. 585-589).

Lu, et al, "Mutations conferring resistance to a potent hepatitis C virus serine protease inhibitors in vitro." Antimicrob Agents Chemother., 2004, vol. 48, pp. 2260-2266.

Maini, et al., "The role of virus-specific CD8(+) cells in liver damage and viral control during persistent hepatitis B virus infection" J. Exp. Med., 2000, vol. 191, pp. 1269-1280.

McCluskie et al., "Immunization Against Hepatitis B Virus by Mucosal Administration of Antigen-Antibody Complexes", Viral Immunology, 1998, vol. 11, No. 4, pp. 245-252.

McHutchison, et al., "Current therapy for hepatitis C: pegylated interferon and ribavirin",Clin. Liver Dis., 2003, vol. 7, pp. 149-161.

Moll, et al., "Designed heterodimerizing leucine zippers with a range of pIs and stabilities up to 10-15 M.", Protein Science, 2001, vol. 10, pp. 649-655.

Morris, et al., "Incorporation of an Isoleucine Zipper Motif Enhances the Biiological Activity of Soluble CD40L (CD154)", The Journal of Biological Chemistry, Jan. 1999, vol. 274, No. 1, pp. 418-422.

Penin et al. (2004) Structural Biology of hepatitis C virus.Hepatology 39: 5-19.

Polyak, et al., "Hepatitis C Virus Nonstructural 5A Protein Induces Interleukin-8, Leading to Partial Inhibition of the Interferon-Induced Antiviral Response", J. Virol., 2001, vol. 75, pp. 6095-6106.

Post, et al., "Clearance of Hepatitis C Viremia Associated with Cellular Immunity in the Absence of Seroconversion in the Hepatitis C Incidence and Transmission in Prisons Study Cohort", J. Infect. Dis., 2004, vol. 189, pp. 1846-1855.

Reiser, et al, "Antiviral efficacy of NS3-serine protease inhibitor BILN-2061 in patients with chronic genotype 2 and 3 hepatitis C", Hepatology, 2005, vol. 41, pp. 832-835.

Sarobe, et al., "Abnormal priming of CD4(+) T cells by dendritic cells expressing hepatitis C virus core and E1 proteins" J. Virol., 2002, vol. 76, pp. 5062-5070.

Sarobe, et al., "Hepatitis C virus structural proteins impair dendritic cell maturation and inhibit in vivo induction of cellular immune responses", J. Virol., 2002, vol. 77, pp. 10862-10871.

Schirmbeck, et al. "Ongoing murine T1 or T2 immune responses to the hepatitis B surface antigen are excluded from the liver that expresses transgene-encoded hepatitis B surface antigen", J. Immunol., Apr. 15, 2000, vol. 164, No. 8), pp. 4235-4243.

Seeff, "Natural history of chronic hepatitis C", Hepatology, 2002, vol. 36, pp. s35-s46.

Shoukry, et al., "Memory CD8+ T cells are required for protection from persistent hepatitis C virus infection", J. Exp. Med., 2003, vol. 197, pp. 1645-1655.

Spaeny-Dekking, et al., "Extracellular granzymes A and B in humans: detection of native species during CTL responses in vitro and in vivo", J. Immunol., 1988, vol. 160, p. 3610.

Strader, "Understudied populations with hepatitis C", Hepatology, 2002, vol. 36, pp. S226-S236.

Strader, et al., (2004) "Diagnosis, management, and treatment of hepatitis C", Hepatology, 2004, vol. 39, pp. 1147-1171.

Tarte, et al., "Dendritic cell-based vaccine: a promising 5 approach for cancer immunotherapy", Leukemia, 1999, vol. 13, pp. 653-663.

Thimme, et al., "Determinants of viral clearance and persistence during acute hepatitis C virus infection", J. Exp. Med., 2002, vol. 194, pp. 1395-1406.

Thimme, et al., "Viral and immunological determinants of hepatitis C virus clearance, persistence, and disease", Proc. Natl. Acad. Sci. USA, 2001, vol. 99, pp. 15661-15668.

Trozzi, et al. "In vitro selection and characterization of hepatitis C virus serine protease variants resistant to an active-site peptide inhibitor", J. Virol., 2003, vol. 77, pp. 3669-3679.

Wei, et al., "Development of the diagnostic immunossay to detect anti-PreS1 (21-47aa) antibody—a marker suggesting the health improvement of hepatitis B patients", Clinical Chemica Acta, 2002, vol. 317, pp. 159-169.

Wen, et al., "Antigen-antibody complex as therapeutic vaccine for viral hepatitis B", Int. Rev. Immunol., 1999, vol. 18, pp. 251-258.

Wen, et al., "Hepatitis B vaccine and anti-HBs complex as approach for vaccine therapy", The Lacent 1995, vol. 345, No. 8964, pp. 1575-1576.

Wetlaufer, et al., "Control of aggregation in protein refolding: A variety of surfactants promote renaturation of carbonice anhydrase II", Prot. Sci., 1995, vol. 4, pp. 1535-1543.

Wieland, et al., "Stealth and cunning: Hepatitis B and Hepatitis C viruses.", J. Virol., 2005, vol. 79, pp. 9369-9380.

Yanagi, et al, "Transcripts from a single full-length cDNA clone of hepatitis C virus are infectious when directly transfected into the liver of a chimpanzee", Proc. Natl. Acad. Sci. USA, 1997, vol. 94, pp. 8738-8743.

Yu, et al., "Priming with CpG-enriched plasmid and boosting with protein formulated with CpG oligodeoxynucleotides and Quil A induces strong cellular and humoral immune responses to hepatitis C virus NS3", J. Gen. Virol., 2004, vol. 85, pp. 1533-1543.

Zheng, et al., "Therapeutic efficacy of hepatitis B surface antigen-antibodies-recombinant ONA composite in HBsAg transgenic mice", Vaccine, Jul. 2001, vol. 19, No. 30, pp. 4219-4225.

Zhong, et al, 2005 "Robust hepatitis C infection in vitro", Proc. Natl. Acad. Sci. USA, 2005, vol. 102, pp. 9294-9299.

Zhong, et al., "A Study of Humoral Immune Responses Induced by Anti-HBs-HBsAg Immunogenic Complexes", Zhonghua Weishengwuxue He Mianyixue Zazhi (Chinese Journal of Microbiology and Immunology) ,1998, vol. 18, No. 4, pp. 331-335 (English Translation Provided).

Alter, et al., "Recovery, persistence and sequelae in hepatitis C virus infection: a perspective on long-term outcome", Semin. Liver Dis., 2000, vol. 20, pp. 17-35.

Andoniou, et al., "Interation between conventional dendritic cells and natural killer cells is integral to the activation of effective antiviral immunity", Nature Immunol. Online, 2005, vol. 6, No. 10, pp. 1011-1019.

Babiuk et al. "Electroporation improves the efficacy of DNA vaccines in large animals." Vaccine, 2002, 20: 3399-3408.

Babiuk et al., "Increased gene expression and inflammatory cell infiltration causedby electroporation are both important for improving the efficacy of DNA vaccines." J. Biotechnol, 2004, 110: 1-10.

Bartenschlager, "Hepatitis C virus replicons: potential role for drug development", Nature Rev. Drug. Discov., 2002, vol. 1, pp. 911-916.

Biochemistry 4th Ed., Lubert Stryer ed., W. H. Freeman and Co., 1995, pp. 18-23.

Björklunda, et al., "Characterization of recombinant human IgE-Fc fragments expressed in baculovirus-infected insect cells", Mol. Immunol., 2000, vol. 37, pp. 169-177.

Bowen, et al., "Adaptive immune responses in acute and chronic hepatitis C virus infection." Nature, 2005, vol. 436, pp. 946-952.

Brown, "Hepatitis C and Liver transplantation", Nature, 2005, vol. 436, No. 7053, pp. 973-978.

Carroll, "The complement system in regulation of adaptive immunity", Nature Immunol., 2005, vol. 5, pp. 981-986.

De Francesco, et al., "Challenges and successes in developing new therapies for hepatitis C", Nature, 2005, vol. 436, pp. 953-960.

Diepolder, et al., "Possible mechanism involving T lymphocyte response to non-structural protein 3 in viral clearance in acute hepatitis C infection", Lancet, 1995, vol. 36, pp. 1006-1007.

Ewen, et al., "A novel cytotoxicity assay to evaluate antigen-specific CTL responses using a colorimetric substrate for Granzyme B" J. Immunol. Meth., 2003, vol. 276, pp. 89-101.

Feld, et al., "Mechanism of action of interferon and ribavirin in treatment of hepatitis C", Nature, 2005, vol. 436, pp. 967-972.

Gale, Jr, et al., "Evasion of intracellular host defence by hepatitis C virus", Nature, 2005, vol. 436, pp. 939-945.

Geijtenbeek, et al., "Self- and nonself-recognition by C-type lectins on dendritic cells", Annu. Rev. Immunol., 2004, vol. 22, pp. 33-54.

George et al. (2006) A new class of therapeutic vaccines for the treatment of chronic hepatitis B infections. In "Framing the Knowledge of Viral Hepatitis" Schinazi, R. F. Editor, 1HL Press USA, pp. 379-403.

George, et al. "Chimigen Vaccines: A novel class of therapeutic vaccines for the treatment of chronic viral infections." International Meeting of the Molecular Biology of Hepatitis B Viruses, Sep. 7-10, 2003, Centro Congressi Giovanni XXIII, Bergamo, Italy, 1 page.

George, et al., "A novel Class of Therapeutic Vaccines for the Treatment of Chronic Viral Infections: Evaluation in Ducks Chronically Infected with Duck Hepatitis B Virus (DHBV)", Hepdart 2003, Frontiers in Drug Development for Viral Hepatitis, Dec. 14-18, Kauai, Hawaii, USA., 1 page.

George, et al., "A New Class of Therapeutic Vaccines Produced in Insect Cells for the Treatment of Chronic Viral Infections", BioProcessing Journal, 2005, vol. 4, pp. 38-44.

George, et al., "Immunological Evaluation of a Novel Chimeric Therapeutic Vaccine for the Treatment of Chronic Hepatitis B Infections", International Meeting of the Molecular Biology of Hepatitis B Viruses, Woods Hole, MA, Oct. 24-27, 2004, 1 page.

Hahn, "Subversion of immune responses by hepatitis C virus: 25 immunomodulatory strategies beyond evasion?", Curr. Opin. Immunol., 2003, vol. 15, pp. 443-449.

Hinrichsen, et al, "Short-term antiviral efficacy of BILN 2061, a hepatitis C 30 virus serine protease inhibitor, in hepatitis C genotype 1 patients", Gastroenterology, 2004, vol. 127, pp. 1347-1355.

Iwasaki, et al., "Toll-like receptor control of the adaptive immune responses", Nature Immunol., 2004, vol. 5, pp. 987-995.

Kozlowski, et al., "Lactacystin inhibits cathepsin A activity in melanoma cell lines", Tumour Biol., 2001, vol. 22, No. 4, pp. 211-215.

Lindenbach, et al., "Unravelling hepatitis C virus replication from genome to function", Nature, 2005, vol. 436, pp. 933-938.

Lizée, et al., "Tails of wonder: endocytic-sorting motifs key for exogenous antigen presentation" Trends Immunol., 2005, vol. 26, No. 3, pp. 141-149.

Lobe, et al, "Novel serine proteases encoded by two cytotoxic T lymphocyte-specific genes." Science, 1986, vol. 232, pp. 858-861.

Lohmann, et al., "Processing pathways of 15 the hepatitis C virus proteins", J. Hepatol., 1996, vol. 24, pp. 11-19.

Yotsuyanagi et al. "Prolonged Fecal Excretion of Hepatitis A Virus in Adult Patients With Hepatitis A as Determined by Polymerase Chain Reaction", Hepatology vol. 24, No. 1, 1996, pp. 10-13.

Mehta, et al, "Protection against persistence of hepatitis C", 2002, Lancet, 2002, vol. 359, pp. 1478-1483.

Mercer, et al, "Hepatitis C virus replication in mice with chimeric human livers", Nat. Med., 2001, vol. 7, pp. 927-933.

Middelberg, "Preparative protein refolding", Trends Biotech., 2002, vol. 20, pp. 437-443.

Pawlotsky, "Diagnostic tests for hepatitis", J. Hepatol., 1999, vol. 31(suppl), pp. 71-79.

Rehermann, et al., "Immunology of hepatitis B and hepatitis C virus infection", Nature Rev. Immunol., 2005, vol. 5, pp. 215-229.

Rozema, et al., "Artificial chaperone-assisted refolding of denatured-reduced lysozyme: Modulation of competition between renaturation and aggregation", Biochem., 1996, vol. 35, pp. 15760-15771.

Shoji, et al., "Internal Processing of Hepatitis C Virus NS3 Protein" Virology, 1999, vol. 254, pp. 315-323.

Shoukry, et al., "Cell-mediated immunity 15 and the outcome of hepatitis C virus infection", Ann. Rev. Microbiol, 2004, vol. 58, pp. 391-424.

Takeda, et al, "Toll-like receptors", Annu. Rev. Immunol., 2003, vol. 21, pp. 335-376.

Taylor, et al., "Macrophage receptors and immune recognition", Annu. Rev. Immunol., 2005, vol. 23, pp. 901-944.

Wakita, et al., 2005 "Production of infectious hepatitis C virus in tissue culture from a cloned viral genome", Nature Med., 2005, vol. 11, pp. 791-796.

Wild, et al., "Primary prevention of hepatocellular carcinoma in developing countries", Mutation Res., 2000, vol. 462, pp. 381-393.

Dieckman et al. "High throughput methods for gene cloning and expression." Protein Expression and Purification published on line Jun. 19, 2002, vol. 25, No. 1, pp. 8-15.

Shiraki et al. "Processing of hepatitis B virus surface antigen expressed by recombinant Oka varicella vaccine virus" J. General Virol. 1992, vol. 73, pp. 1401-1407.

Purcell, "The Hepatitis C Virus: Overview," Hepatology, 1997, vol. 26(3), pp. 11S-14S.

Wines et al. "The IgG Fc Contains Distinct Fc Receptor (FcR) Binding Sites: The Leukocyte Receptors Fc{gamma}RI and Fc{gamma}RIIa Bind to a Region in the Fc Distinct from That Recognized by Neonatal FcR and Protein A," J. Immuno., 2000, vol. 164, pp. 5313-5318.

* cited by examiner

SEQUENCE LISTING

```
<160> NUMBER OF SEQ ID NOS: 51

<210> SEQ ID NO 1
<211> LENGTH: 8
<212> TYPE: PRT
<213> ORGANISM: Artificial
<220> FEATURE:
<223> OTHER INFORMATION: linker peptide
<220> FEATURE:
<221> NAME/KEY: misc_feature
<222> LOCATION: (1)..(1)
<223> OTHER INFORMATION: Xaa can be Val or Ser

<400> SEQUENCE: 1

Xaa Arg Pro Gln Gly Gly Gly Ser
1               5

<210> SEQ ID NO 2
<211> LENGTH: 5
<212> TYPE: PRT
<213> ORGANISM: Mus musculus
```

<400> SEQUENCE: 2

Val Asp Lys Lys Ile
1               5

<210> SEQ ID NO 3
<211> LENGTH: 55
<212> TYPE: DNA
<213> ORGANISM: artificial sequence
<220> FEATURE:
<223> OTHER INFORMATION: primer sequence

<400> SEQUENCE: 3
tgtcattctg cggccgcaag gcggcggatc cgtggacaag aaaattgtgc ccagg        55

<210> SEQ ID NO 4
<211> LENGTH: 36
<212> TYPE: DNA
<213> ORGANISM: artificial sequence
<220> FEATURE:
<223> OTHER INFORMATION: primer sequence

<400> SEQUENCE: 4
acgaatcaag ctttgcagcc caggagagtg ggagag                             36

<210> SEQ ID NO 5
<211> LENGTH: 21
<212> TYPE: DNA
<213> ORGANISM: artificial sequence
<220> FEATURE:
<223> OTHER INFORMATION: primer sequence

<400> SEQUENCE: 5
tattccggat tattcatacc g                                             21

<210> SEQ ID NO 6
<211> LENGTH: 20
<212> TYPE: DNA
<213> ORGANISM: artificial sequence
<220> FEATURE:
<223> OTHER INFORMATION: primer sequence

<400> SEQUENCE: 6
ctctacaaat gtggtatggc                                               20

<210> SEQ ID NO 7
<211> LENGTH: 20
<212> TYPE: DNA
<213> ORGANISM: artificial sequence
<220> FEATURE:
<223> OTHER INFORMATION: primer sequence

<400> SEQUENCE: 7
ggatctgtac gacgatgacg                                               20

<210> SEQ ID NO 8
<211> LENGTH: 39
<212> TYPE: DNA
<213> ORGANISM: artificial sequence
<220> FEATURE:
<223> OTHER INFORMATION: primer sequence

<400> SEQUENCE: 8
agtcattctg cggccgcgag ttcgtcacag ggtccccgg                          39

<210> SEQ ID NO 9
<211> LENGTH: 34

```
<212> TYPE: DNA
<213> ORGANISM: artificial sequence
<220> FEATURE:
<223> OTHER INFORMATION: primer sequence

<400> SEQUENCE: 9
gataaggatc ctatgggagg ttggtcatca aaac                             34

<210> SEQ ID NO 10
<211> LENGTH: 40
<212> TYPE: DNA
<213> ORGANISM: artificial sequence
<220> FEATURE:
<223> OTHER INFORMATION: primer sequence

<400> SEQUENCE: 10
gtcatactgc ggccgcgaaa tgtataccca gagacaaaag                       40

<210> SEQ ID NO 11
<211> LENGTH: 31
<212> TYPE: DNA
<213> ORGANISM: artificial sequence
<220> FEATURE:
<223> OTHER INFORMATION: primer sequence

<400> SEQUENCE: 11
tgcgctacca tggacattga cccttataaa g                                31

<210> SEQ ID NO 12
<211> LENGTH: 42
<212> TYPE: DNA
<213> ORGANISM: artificial sequence
<220> FEATURE:
<223> OTHER INFORMATION: primer sequence

<400> SEQUENCE: 12
tgtcattctg cggccgcgaa cattgagatt cccgagattg ag                    42

<210> SEQ ID NO 13
<211> LENGTH: 40
<212> TYPE: DNA
<213> ORGANISM: artificial sequence
<220> FEATURE:
<223> OTHER INFORMATION: primer sequence

<400> SEQUENCE: 13
tgtcattcag cggccgcgaa ctcttgtaaa aaagagcaga                       40

<210> SEQ ID NO 14
<211> LENGTH: 40
<212> TYPE: DNA
<213> ORGANISM: artificial sequence
<220> FEATURE:
<223> OTHER INFORMATION: primer sequence

<400> SEQUENCE: 14
tgtcattctg cggccgcgtt ttcttcttca aggggggagt                       40

<210> SEQ ID NO 15
<211> LENGTH: 33
<212> TYPE: DNA
<213> ORGANISM: artificial sequence
<220> FEATURE:
<223> OTHER INFORMATION: primer sequence

<400> SEQUENCE: 15
tgcgctacca tggatatcaa tgcttctaga gcc                              33
```

```
<210> SEQ ID NO 16
<211> LENGTH: 43
<212> TYPE: DNA
<213> ORGANISM: artificial sequence
<220> FEATURE:
<223> OTHER INFORMATION: primer sequence

<400> SEQUENCE: 16
tgtcattctg cggccgcgat ttcctaggcg agggagatct atg          43

<210> SEQ ID NO 17
<211> LENGTH: 27
<212> TYPE: DNA
<213> ORGANISM: artificial sequence
<220> FEATURE:
<223> OTHER INFORMATION: primer sequence

<400> SEQUENCE: 17
cggaattcat gagcacgaat cctaaac                             27

<210> SEQ ID NO 18
<211> LENGTH: 38
<212> TYPE: DNA
<213> ORGANISM: artificial sequence
<220> FEATURE:
<223> OTHER INFORMATION: primer sequence

<400> SEQUENCE: 18
ggactagtcc ggctgaagcg ggcacagtca ggcaagag                 38

<210> SEQ ID NO 19
<211> LENGTH: 27
<212> TYPE: DNA
<213> ORGANISM: artificial sequence
<220> FEATURE:
<223> OTHER INFORMATION: primer sequence

<400> SEQUENCE: 19
ggactagtcc gaagatagag aaagagc                             27

<210> SEQ ID NO 20
<211> LENGTH: 27
<212> TYPE: DNA
<213> ORGANISM: artificial sequence
<220> FEATURE:
<223> OTHER INFORMATION: primer sequence

<400> SEQUENCE: 20
ccggaattct ccggttcctg gctaagg                             27

<210> SEQ ID NO 21
<211> LENGTH: 28
<212> TYPE: DNA
<213> ORGANISM: artificial sequence
<220> FEATURE:
<223> OTHER INFORMATION: primer sequence

<400> SEQUENCE: 21
ggactagtcc gcacacgaca tcttccgt                            28

<210> SEQ ID NO 22
<211> LENGTH: 28
<212> TYPE: DNA
<213> ORGANISM: artificial sequence
<220> FEATURE:
<223> OTHER INFORMATION: primer sequence
```

```
<400> SEQUENCE: 22
ccggaattct accaagtgcg caattcct                                              28

<210> SEQ ID NO 23
<211> LENGTH: 32
<212> TYPE: DNA
<213> ORGANISM: artificial sequence
<220> FEATURE:
<223> OTHER INFORMATION: primer sequence

<400> SEQUENCE: 23
ggactagtcc ttccgcgtcg acgccggcaa at                                         32

<210> SEQ ID NO 24
<211> LENGTH: 32
<212> TYPE: DNA
<213> ORGANISM: artificial sequence
<220> FEATURE:
<223> OTHER INFORMATION: primer sequence

<400> SEQUENCE: 24
gcggaattca cccacgtcac cgggggaaat gc                                         32

<210> SEQ ID NO 25
<211> LENGTH: 35
<212> TYPE: DNA
<213> ORGANISM: artificial sequence
<220> FEATURE:
<223> OTHER INFORMATION: primer sequence

<400> SEQUENCE: 25
ggactagtcc agccgcctcc gcttgggata tgagt                                      35

<210> SEQ ID NO 26
<211> LENGTH: 1359
<212> TYPE: DNA
<213> ORGANISM: Artificial
<220> FEATURE:
<223> OTHER INFORMATION: HBV plus TBD
<220> FEATURE:
<221> NAME/KEY: CDS
<222> LOCATION: (1)..(1359)

<400> SEQUENCE: 26 atg tcg tac tac cat cac cat cac cat cac gat tac gat atc cca acg         48
Met Ser Tyr Tyr His His His His His His Asp Tyr Asp Ile Pro Thr
 1               5                  10                  15 acc gaa aac ctg tat ttt cag ggc gcc atg gat cct atg aaa aaa tgg         96
Thr Glu Asn Leu Tyr Phe Gln Gly Ala Met Asp Pro Met Lys Lys Trp
             20                  25                  30 tca tca aaa cct cgc aaa ggc atg ggg acg aat ctt tct gtt ccc aac        144
Ser Ser Lys Pro Arg Lys Gly Met Gly Thr Asn Leu Ser Val Pro Asn
         35                  40                  45 cct ctg gga ttc ttt ccc gat cat cag ttg gac cct gta ttc gga gcc        192
Pro Leu Gly Phe Phe Pro Asp His Gln Leu Asp Pro Val Phe Gly Ala
     50                  55                  60 aac tca aac aat cca gat tgg gac ttc aac ccc atc aag gac cac tgg        240
Asn Ser Asn Asn Pro Asp Trp Asp Phe Asn Pro Ile Lys Asp His Trp
 65                  70                  75                  80 cca gca gcc aac cag gta gga gtg gga gca ttc ggg cca ggg ttc acc        288
Pro Ala Ala Asn Gln Val Gly Val Gly Ala Phe Gly Pro Gly Phe Thr
                 85                  90                  95 cct cca cac ggc ggt gtt ttg ggg tgg agc cct cag gct cag ggc atg        336
Pro Pro His Gly Gly Val Leu Gly Trp Ser Pro Gln Ala Gln Gly Met
```

-continued

```
                100                 105                 110
ttg acc cca gtg tca aca att cct cct cct gcc tcc gcc aat cgg cag      384
Leu Thr Pro Val Ser Thr Ile Pro Pro Pro Ala Ser Ala Asn Arg Gln
        115                 120                 125 tca gga agg cag cct act ccc atc tct cca cct cta aga gac agt cat      432
Ser Gly Arg Gln Pro Thr Pro Ile Ser Pro Pro Leu Arg Asp Ser His
130                 135                 140 cct cag gcc atg cag tgg aat tcc act gcc ttc cac caa gct ctg caa      480
Pro Gln Ala Met Gln Trp Asn Ser Thr Ala Phe His Gln Ala Leu Gln
145                 150                 155                 160 gac ccc aga gtc agg ggt ctg tat ttt cct gct ggt ggc tcc agt tca      528
Asp Pro Arg Val Arg Gly Leu Tyr Phe Pro Ala Gly Gly Ser Ser Ser
                165                 170                 175 gga aca gta aac cct gct ccg aat att gcc tct cac atc tcg tca atc      576
Gly Thr Val Asn Pro Ala Pro Asn Ile Ala Ser His Ile Ser Ser Ile
        180                 185                 190 tcc gcg agg acc ggg gac cct gtg acg aac tcg cgg ccg caa ggc ggc      624
Ser Ala Arg Thr Gly Asp Pro Val Thr Asn Ser Arg Pro Gln Gly Gly
    195                 200                 205 gga tcc gtg gac aag aaa att gtg ccc agg gat tgt ggt tgt aag cct      672
Gly Ser Val Asp Lys Lys Ile Val Pro Arg Asp Cys Gly Cys Lys Pro
210                 215                 220 tgc ata tgt aca gtc cca gaa gta tca tct gtc ttc atc ttc ccc cca      720
Cys Ile Cys Thr Val Pro Glu Val Ser Ser Val Phe Ile Phe Pro Pro
225                 230                 235                 240 aag ccc aag gat gtg ctc acc att act ctg act cct aag gtc acg tgt      768
Lys Pro Lys Asp Val Leu Thr Ile Thr Leu Thr Pro Lys Val Thr Cys
                245                 250                 255 gtt gtg gta gac atc agc aag gat gat ccc gag gtc cag ttc agc tgg      816
Val Val Val Asp Ile Ser Lys Asp Asp Pro Glu Val Gln Phe Ser Trp
        260                 265                 270 ttt gta gat gat gtg gag gtg cac aca gct cag acg caa ccc cgg gag      864
Phe Val Asp Asp Val Glu Val His Thr Ala Gln Thr Gln Pro Arg Glu
    275                 280                 285 gag cag ttc aac agc act ttc cgc tca gtc agt gaa ctt ccc atc atg      912
Glu Gln Phe Asn Ser Thr Phe Arg Ser Val Ser Glu Leu Pro Ile Met
290                 295                 300 cac cag gac tgg ctc aat ggc aag gag ttc aaa tgc agg gtc aac agt      960
His Gln Asp Trp Leu Asn Gly Lys Glu Phe Lys Cys Arg Val Asn Ser
305                 310                 315                 320 gca gct ttc cct gcc ccc atc gag aaa acc atc tcc aaa acc aaa ggc     1008
Ala Ala Phe Pro Ala Pro Ile Glu Lys Thr Ile Ser Lys Thr Lys Gly
                325                 330                 335 aga ccg aag gct cca cag gtg tac acc att cca cct ccc aag gag cag     1056
Arg Pro Lys Ala Pro Gln Val Tyr Thr Ile Pro Pro Pro Lys Glu Gln
        340                 345                 350 atg gcc aag gat aaa gtc agt ctg acc tgc atg ata aca gac ttc ttc     1104
Met Ala Lys Asp Lys Val Ser Leu Thr Cys Met Ile Thr Asp Phe Phe
    355                 360                 365 cct gaa gac att act gtg gag tgg cag tgg aat ggg cag cca gcg gag     1152
Pro Glu Asp Ile Thr Val Glu Trp Gln Trp Asn Gly Gln Pro Ala Glu
370                 375                 380 aac tac aag aac act cag ccc atc atg gac aca gat ggc tct tac ttc     1200
Asn Tyr Lys Asn Thr Gln Pro Ile Met Asp Thr Asp Gly Ser Tyr Phe
385                 390                 395                 400 gtc tac agc aag ctc aat gtg cag aag agc aac tgg gag gca gga aat     1248
Val Tyr Ser Lys Leu Asn Val Gln Lys Ser Asn Trp Glu Ala Gly Asn
                405                 410                 415 act ttc acc tgc tct gtg tta cat gag ggc ctg cac aac cac cat act     1296
Thr Phe Thr Cys Ser Val Leu His Glu Gly Leu His Asn His His Thr
```

```
                    420             425             430
gag aag agc ctc tcc cac tct cct ggg ctg caa agc ttg tcg aga agt    1344
Glu Lys Ser Leu Ser His Ser Pro Gly Leu Gln Ser Leu Ser Arg Ser
        435                 440                 445 act aga gga tca taa                                                1359
Thr Arg Gly Ser
    450

<210> SEQ ID NO 27
<211> LENGTH: 452
<212> TYPE: PRT
<213> ORGANISM: Artificial
<220> FEATURE:
<223> OTHER INFORMATION: Synthetic Construct

<400> SEQUENCE: 27

Met Ser Tyr Tyr His His His His His Asp Tyr Asp Ile Pro Thr
1               5                   10                  15

Thr Glu Asn Leu Tyr Phe Gln Gly Ala Met Asp Pro Met Lys Lys Trp
                20                  25                  30

Ser Ser Lys Pro Arg Lys Gly Met Gly Thr Asn Leu Ser Val Pro Asn
            35                  40                  45

Pro Leu Gly Phe Phe Pro Asp His Gln Leu Asp Pro Val Phe Gly Ala
        50                  55                  60

Asn Ser Asn Asn Pro Asp Trp Asp Phe Asn Pro Ile Lys Asp His Trp
65                  70                  75                  80

Pro Ala Ala Asn Gln Val Gly Val Gly Ala Phe Gly Pro Gly Phe Thr
                85                  90                  95

Pro Pro His Gly Gly Val Leu Gly Trp Ser Pro Gln Ala Gln Gly Met
            100                 105                 110

Leu Thr Pro Val Ser Thr Ile Pro Pro Ala Ser Ala Asn Arg Gln
        115                 120                 125

Ser Gly Arg Gln Pro Thr Pro Ile Ser Pro Pro Leu Arg Asp Ser His
    130                 135                 140

Pro Gln Ala Met Gln Trp Asn Ser Thr Ala Phe His Gln Ala Leu Gln
145                 150                 155                 160

Asp Pro Arg Val Arg Gly Leu Tyr Phe Pro Ala Gly Gly Ser Ser Ser
                165                 170                 175

Gly Thr Val Asn Pro Ala Pro Asn Ile Ala Ser His Ile Ser Ser Ile
            180                 185                 190

Ser Ala Arg Thr Gly Asp Pro Val Thr Asn Ser Arg Pro Gln Gly Gly
        195                 200                 205

Gly Ser Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320
```

```
Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
            355                 360                 365

Pro Glu Asp Ile Thr Val Glu Trp Gln Trp Asn Gly Gln Pro Ala Glu
        370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Leu Gln Ser Leu Ser Arg Ser
            435                 440                 445

Thr Arg Gly Ser
    450

<210> SEQ ID NO 28
<211> LENGTH: 2037
<212> TYPE: DNA
<213> ORGANISM: Artificial
<220> FEATURE:
<223> OTHER INFORMATION: Hepatitis B Virus plus murine
<220> FEATURE:
<221> NAME/KEY: CDS
<222> LOCATION: (1)..(2037)

<400> SEQUENCE: 28 atg tcg tac tac cat cac cat cac cac gat tac gat atc cca acg      48
Met Ser Tyr Tyr His His His His His Asp Tyr Asp Ile Pro Thr
1               5                   10                  15 acc gaa aac ctg tat ttt cag ggc gcc atg gat cct atg gga ggt tgg  96
Thr Glu Asn Leu Tyr Phe Gln Gly Ala Met Asp Pro Met Gly Gly Trp
            20                  25                  30 tca tca aaa cct cgc aaa ggc atg ggg acg aat ctt tct gtt ccc aac 144
Ser Ser Lys Pro Arg Lys Gly Met Gly Thr Asn Leu Ser Val Pro Asn
        35                  40                  45 cct ctg gga ttc ttt ccc gat cat cag ttg gac cct gta ttc gga gcc 192
Pro Leu Gly Phe Phe Pro Asp His Gln Leu Asp Pro Val Phe Gly Ala
    50                  55                  60 aac tca aac aat cca gat tgg gac ttc aac ccc atc aag gac cac tgg 240
Asn Ser Asn Asn Pro Asp Trp Asp Phe Asn Pro Ile Lys Asp His Trp
65                  70                  75                  80 cca gca gcc aac cag gta gga gtg gga gca ttc ggg cca ggg ttc acc 288
Pro Ala Ala Asn Gln Val Gly Val Gly Ala Phe Gly Pro Gly Phe Thr
                85                  90                  95 cct cca cac ggc ggt gtt ttg ggg tgg agc cct cag gct cag ggc atg 336
Pro Pro His Gly Gly Val Leu Gly Trp Ser Pro Gln Ala Gln Gly Met
            100                 105                 110 ttg acc cca gtg tca aca att cct cct cct gcc tcc gcc aat cgg cag 384
Leu Thr Pro Val Ser Thr Ile Pro Pro Pro Ala Ser Ala Asn Arg Gln
        115                 120                 125 tca gga agg cag cct act ccc atc tct cca cct cta aga gac agt cat 432
Ser Gly Arg Gln Pro Thr Pro Ile Ser Pro Pro Leu Arg Asp Ser His
    130                 135                 140 cct cag gcc atg cag tgg aat tcc act gcc ttc cac caa gct ctg caa 480
Pro Gln Ala Met Gln Trp Asn Ser Thr Ala Phe His Gln Ala Leu Gln
145                 150                 155                 160
```

```
                                                      -continued
gac ccc aga gtc agg ggt ctg tat ttt cct gct ggt ggc tcc agt tca       528
Asp Pro Arg Val Arg Gly Leu Tyr Phe Pro Ala Gly Gly Ser Ser Ser
            165                 170                 175 gga aca gta aac cct gct ccg aat att gcc tct cac atc tcg tca atc       576
Gly Thr Val Asn Pro Ala Pro Asn Ile Ala Ser His Ile Ser Ser Ile
        180                 185                 190 tcc gcg agg act ggg gac cct gtg acg aac atg gag aac atc aca tca       624
Ser Ala Arg Thr Gly Asp Pro Val Thr Asn Met Glu Asn Ile Thr Ser
        195                 200                 205 gga ttc cta gga ccc ctg ctc gtg tta cag gcg ggg ttt ttc ttg ttg       672
Gly Phe Leu Gly Pro Leu Leu Val Leu Gln Ala Gly Phe Phe Leu Leu
    210                 215                 220 aca aga atc ctc aca ata ccg cag agt cta gac tcg tgg tgg act tct       720
Thr Arg Ile Leu Thr Ile Pro Gln Ser Leu Asp Ser Trp Trp Thr Ser
225                 230                 235                 240 ctc aat ttt cta ggg gga tca ccc gtg tgt ctt ggc caa aat tcg cag       768
Leu Asn Phe Leu Gly Gly Ser Pro Val Cys Leu Gly Gln Asn Ser Gln
                245                 250                 255 tcc cca acc tcc aat cac tca cca acc tcc tgt cct cca att tgt cct       816
Ser Pro Thr Ser Asn His Ser Pro Thr Ser Cys Pro Pro Ile Cys Pro
            260                 265                 270 ggt tat cgc tgg atg tgt ctg cgg cgt ttt atc ata ttc ctc ttc atc       864
Gly Tyr Arg Trp Met Cys Leu Arg Arg Phe Ile Ile Phe Leu Phe Ile
        275                 280                 285 ctg ctg cta tgc ctc atc ttc tta ttg gtt ctt ctg gat tat caa ggt       912
Leu Leu Leu Cys Leu Ile Phe Leu Leu Val Leu Leu Asp Tyr Gln Gly
        290                 295                 300 atg ttg ccc gtt tgt cct cta att cca gga tca aca acc agt acg           960
Met Leu Pro Val Cys Pro Leu Ile Pro Gly Ser Thr Thr Thr Ser Thr
305                 310                 315                 320 gga cca tgc aaa acc tgc acg act cct gct caa ggc aac tct atg ttt      1008
Gly Pro Cys Lys Thr Cys Thr Thr Pro Ala Gln Gly Asn Ser Met Phe
                325                 330                 335 ccc tca tgt tgc tgt aca aaa cct acg gat gga aat tgc acc tgt att      1056
Pro Ser Cys Cys Cys Thr Lys Pro Thr Asp Gly Asn Cys Thr Cys Ile
            340                 345                 350 ccc atc cca tcg tct tgg gct ttc gca aaa tac cta tgg gag tgg gcc      1104
Pro Ile Pro Ser Ser Trp Ala Phe Ala Lys Tyr Leu Trp Glu Trp Ala
        355                 360                 365 tca gtc cgt ttc tct tgg ctc agt tta cta gtg cca ttt gtt cag tgg      1152
Ser Val Arg Phe Ser Trp Leu Ser Leu Leu Val Pro Phe Val Gln Trp
        370                 375                 380 ttc gta ggg ctt tcc ccc act gtt tgg ctt tca gct ata tgg atg atg      1200
Phe Val Gly Leu Ser Pro Thr Val Trp Leu Ser Ala Ile Trp Met Met
385                 390                 395                 400 tgg tat tgg ggg cca agt ctg tac agc atc gtg agt ccc ttt ata ccg      1248
Trp Tyr Trp Gly Pro Ser Leu Tyr Ser Ile Val Ser Pro Phe Ile Pro
                405                 410                 415 ctg tta cca att ttc ttt tgt ctc tgg gta tac att tcg cgg ccg caa      1296
Leu Leu Pro Ile Phe Phe Cys Leu Trp Val Tyr Ile Ser Arg Pro Gln
            420                 425                 430 ggc ggc gga tcc gtg gac aag aaa att gtg ccc agg gat tgt ggt tgt      1344
Gly Gly Gly Ser Val Asp Lys Lys Ile Val Pro Arg Asp Cys Gly Cys
        435                 440                 445 aag cct tgc ata tgt aca gtc cca gaa gta tca tct gtc ttc atc ttc      1392
Lys Pro Cys Ile Cys Thr Val Pro Glu Val Ser Ser Val Phe Ile Phe
        450                 455                 460 ccc cca aag ccc aag gat gtg ctc acc att act ctg act cct aag gtc      1440
Pro Pro Lys Pro Lys Asp Val Leu Thr Ile Thr Leu Thr Pro Lys Val
465                 470                 475                 480
```

```
acg tgt gtt gtg gta gac atc agc aag gat gat ccc gag gtc cag ttc    1488
Thr Cys Val Val Val Asp Ile Ser Lys Asp Asp Pro Glu Val Gln Phe
            485                 490                 495 agc tgg ttt gta gat gat gtg gag gtg cac aca gct cag acg caa ccc    1536
Ser Trp Phe Val Asp Asp Val Glu Val His Thr Ala Gln Thr Gln Pro
        500                 505                 510 cgg gag gag cag ttc aac agc act ttc cgc tca gtc agt gaa ctt ccc    1584
Arg Glu Glu Gln Phe Asn Ser Thr Phe Arg Ser Val Ser Glu Leu Pro
            515                 520                 525 atc atg cac cag gac tgg ctc aat ggc aag gag ttc aaa tgc agg gtc    1632
Ile Met His Gln Asp Trp Leu Asn Gly Lys Glu Phe Lys Cys Arg Val
        530                 535                 540 aac agt gca gct ttc cct gcc ccc atc gag aaa acc atc tcc aaa acc    1680
Asn Ser Ala Ala Phe Pro Ala Pro Ile Glu Lys Thr Ile Ser Lys Thr
545                 550                 555                 560 aaa ggc aga ccg aag gct cca cag gtg tac acc att cca cct ccc aag    1728
Lys Gly Arg Pro Lys Ala Pro Gln Val Tyr Thr Ile Pro Pro Pro Lys
            565                 570                 575 gag cag atg gcc aag gat aaa gtc agt ctg acc tgc atg ata aca gac    1776
Glu Gln Met Ala Lys Asp Lys Val Ser Leu Thr Cys Met Ile Thr Asp
        580                 585                 590 ttc ttc cct gaa gac att act gtg gag tgg cag tgg aat ggg cag cca    1824
Phe Phe Pro Glu Asp Ile Thr Val Glu Trp Gln Trp Asn Gly Gln Pro
            595                 600                 605 gcg gag aac tac aag aac act cag ccc atc atg gac aca gat ggc tct    1872
Ala Glu Asn Tyr Lys Asn Thr Gln Pro Ile Met Asp Thr Asp Gly Ser
        610                 615                 620 tac ttc gtc tac agc aag ctc aat gtg cag aag agc aac tgg gag gca    1920
Tyr Phe Val Tyr Ser Lys Leu Asn Val Gln Lys Ser Asn Trp Glu Ala
625                 630                 635                 640 gga aat act ttc acc tgc tct gtg tta cat gag ggc ctg cac aac cac    1968
Gly Asn Thr Phe Thr Cys Ser Val Leu His Glu Gly Leu His Asn His
            645                 650                 655 cat act gag aag agc ctc tcc cac tct cct ggg ctg caa agc ttg tcg    2016
His Thr Glu Lys Ser Leu Ser His Ser Pro Gly Leu Gln Ser Leu Ser
        660                 665                 670 aga agt act aga gga tca taa                                        2037
Arg Ser Thr Arg Gly Ser
            675
```

<210> SEQ ID NO 29
<211> LENGTH: 678
<212> TYPE: PRT
<213> ORGANISM: Artificial
<220> FEATURE:
<223> OTHER INFORMATION: Synthetic Construct

<400> SEQUENCE: 29

```
Met Ser Tyr Tyr His His His His His Asp Tyr Asp Ile Pro Thr
1               5                   10                  15

Thr Glu Asn Leu Tyr Phe Gln Gly Ala Met Asp Pro Met Gly Gly Trp
            20                  25                  30

Ser Ser Lys Pro Arg Lys Gly Met Gly Thr Asn Leu Ser Val Pro Asn
        35                  40                  45

Pro Leu Gly Phe Phe Pro Asp His Gln Leu Asp Pro Val Phe Gly Ala
    50                  55                  60

Asn Ser Asn Asn Pro Asp Trp Asp Phe Asn Pro Ile Lys Asp His Trp
65                  70                  75                  80

Pro Ala Ala Asn Gln Val Gly Val Gly Ala Phe Gly Pro Gly Phe Thr
                85                  90                  95
```

```
Pro Pro His Gly Gly Val Leu Gly Trp Ser Pro Gln Ala Gln Gly Met
            100                 105                 110
Leu Thr Pro Val Ser Thr Ile Pro Pro Ala Ser Ala Asn Arg Gln
        115                 120                 125
Ser Gly Arg Gln Pro Thr Pro Ile Ser Pro Pro Leu Arg Asp Ser His
130                 135                 140
Pro Gln Ala Met Gln Trp Asn Ser Thr Ala Phe His Gln Ala Leu Gln
145                 150                 155                 160
Asp Pro Arg Val Arg Gly Leu Tyr Phe Pro Ala Gly Gly Ser Ser Ser
                165                 170                 175
Gly Thr Val Asn Pro Ala Pro Asn Ile Ala Ser His Ile Ser Ser Ile
            180                 185                 190
Ser Ala Arg Thr Gly Asp Pro Val Thr Asn Met Glu Asn Ile Thr Ser
        195                 200                 205
Gly Phe Leu Gly Pro Leu Leu Val Leu Gln Ala Gly Phe Phe Leu Leu
210                 215                 220
Thr Arg Ile Leu Thr Ile Pro Gln Ser Leu Asp Ser Trp Trp Thr Ser
225                 230                 235                 240
Leu Asn Phe Leu Gly Gly Ser Pro Val Cys Leu Gly Gln Asn Ser Gln
                245                 250                 255
Ser Pro Thr Ser Asn His Ser Pro Thr Ser Cys Pro Pro Ile Cys Pro
            260                 265                 270
Gly Tyr Arg Trp Met Cys Leu Arg Arg Phe Ile Ile Phe Leu Phe Ile
        275                 280                 285
Leu Leu Leu Cys Leu Ile Phe Leu Leu Val Leu Leu Asp Tyr Gln Gly
290                 295                 300
Met Leu Pro Val Cys Pro Leu Ile Pro Gly Ser Thr Thr Thr Ser Thr
305                 310                 315                 320
Gly Pro Cys Lys Thr Cys Thr Thr Pro Ala Gln Gly Asn Ser Met Phe
                325                 330                 335
Pro Ser Cys Cys Cys Thr Lys Pro Thr Asp Gly Asn Cys Thr Cys Ile
            340                 345                 350
Pro Ile Pro Ser Ser Trp Ala Phe Ala Lys Tyr Leu Trp Glu Trp Ala
        355                 360                 365
Ser Val Arg Phe Ser Trp Leu Ser Leu Leu Val Pro Phe Val Gln Trp
370                 375                 380
Phe Val Gly Leu Ser Pro Thr Val Trp Leu Ser Ala Ile Trp Met Met
385                 390                 395                 400
Trp Tyr Trp Gly Pro Ser Leu Tyr Ser Ile Val Ser Pro Phe Ile Pro
                405                 410                 415
Leu Leu Pro Ile Phe Phe Cys Leu Trp Val Tyr Ile Ser Arg Pro Gln
            420                 425                 430
Gly Gly Gly Ser Val Asp Lys Lys Ile Val Pro Arg Asp Cys Gly Cys
        435                 440                 445
Lys Pro Cys Ile Cys Thr Val Pro Glu Val Ser Ser Val Phe Ile Phe
450                 455                 460
Pro Pro Lys Pro Lys Asp Val Leu Thr Ile Thr Leu Thr Pro Lys Val
465                 470                 475                 480
Thr Cys Val Val Val Asp Ile Ser Lys Asp Asp Pro Glu Val Gln Phe
                485                 490                 495
Ser Trp Phe Val Asp Asp Val Glu Val His Thr Ala Gln Thr Gln Pro
            500                 505                 510
Arg Glu Glu Gln Phe Asn Ser Thr Phe Arg Ser Val Ser Glu Leu Pro
        515                 520                 525
```

```
Ile Met His Gln Asp Trp Leu Asn Gly Lys Glu Phe Lys Cys Arg Val
    530                 535                 540
Asn Ser Ala Ala Phe Pro Ala Pro Ile Glu Lys Thr Ile Ser Lys Thr
545                 550                 555                 560
Lys Gly Arg Pro Lys Ala Pro Gln Val Tyr Thr Ile Pro Pro Lys
                565                 570                 575
Glu Gln Met Ala Lys Asp Lys Val Ser Leu Thr Cys Met Ile Thr Asp
                580                 585                 590
Phe Phe Pro Glu Asp Ile Thr Val Glu Trp Gln Trp Asn Gly Gln Pro
            595                 600                 605
Ala Glu Asn Tyr Lys Asn Thr Gln Pro Ile Met Asp Thr Asp Gly Ser
        610                 615                 620
Tyr Phe Val Tyr Ser Lys Leu Asn Val Gln Lys Ser Asn Trp Glu Ala
625                 630                 635                 640
Gly Asn Thr Phe Thr Cys Ser Val Leu His Glu Gly Leu His Asn His
                645                 650                 655
His Thr Glu Lys Ser Leu Ser His Ser Pro Gly Leu Gln Ser Leu Ser
                660                 665                 670
Arg Ser Thr Arg Gly Ser
            675

<210> SEQ ID NO 30
<211> LENGTH: 1383
<212> TYPE: DNA
<213> ORGANISM: Artificial
<220> FEATURE:
<223> OTHER INFORMATION: Hepatitis B virus plus murine
<220> FEATURE:
<221> NAME/KEY: CDS
<222> LOCATION: (1)..(1383)

<400> SEQUENCE: 30 atg tcg tac tac cat cac cat cac cat cac gat tac gat atc cca acg        48
Met Ser Tyr Tyr His His His His His His Asp Tyr Asp Ile Pro Thr
1               5                   10                  15 acc gaa aac ctg tat ttt cag ggc gcc atg gac att gac cct tat aaa        96
Thr Glu Asn Leu Tyr Phe Gln Gly Ala Met Asp Ile Asp Pro Tyr Lys
            20                  25                  30 gaa ttt gga gct act gtg gag tta ctc tcg ttt ttg cct tct gac ttc       144
Glu Phe Gly Ala Thr Val Glu Leu Leu Ser Phe Leu Pro Ser Asp Phe
        35                  40                  45 ttt cct tcc gtc aga gat ctc cta gac acc gcc tcg gct ctg tat cgg       192
Phe Pro Ser Val Arg Asp Leu Leu Asp Thr Ala Ser Ala Leu Tyr Arg
    50                  55                  60 gaa gcc tta gag tct cct gag cat tgc tca cct cac cat acc gca ctc       240
Glu Ala Leu Glu Ser Pro Glu His Cys Ser Pro His His Thr Ala Leu
65                  70                  75                  80 agg caa gcc att ctc tgc tgg ggg gaa ttg atg act cta gct acc tgg       288
Arg Gln Ala Ile Leu Cys Trp Gly Glu Leu Met Thr Leu Ala Thr Trp
                85                  90                  95 gtg ggt aat aat ttg gaa gat cca gca tcc agg gat cta gta gtc aat       336
Val Gly Asn Asn Leu Glu Asp Pro Ala Ser Arg Asp Leu Val Val Asn
            100                 105                 110 tat gtt aat act aac atg gga tta aag atc agg caa ctc ttg tgg ttt       384
Tyr Val Asn Thr Asn Met Gly Leu Lys Ile Arg Gln Leu Leu Trp Phe
        115                 120                 125 cat atc tct tgc ctt act ttt gga aga gaa act gta ctt gaa tat ttg       432
His Ile Ser Cys Leu Thr Phe Gly Arg Glu Thr Val Leu Glu Tyr Leu
    130                 135                 140
```

-continued

```
gtc tct ttc gga gtg tgg att cgc act cct cca gcc tat aga cca cca      480
Val Ser Phe Gly Val Trp Ile Arg Thr Pro Pro Ala Tyr Arg Pro Pro
145                 150                 155                 160 aat gcc cct atc tta tca aca ctt ccg gaa act act gtt gtt aga cga      528
Asn Ala Pro Ile Leu Ser Thr Leu Pro Glu Thr Thr Val Val Arg Arg
                165                 170                 175 cgg gac cga ggc agg tcc cct aga aga aga act ccc tcg cct cgc aga      576
Arg Asp Arg Gly Arg Ser Pro Arg Arg Arg Thr Pro Ser Pro Arg Arg
            180                 185                 190 cgc aga tct caa tcg ccg cgt cgc aga aga tct caa tct cgg gaa tct      624
Arg Arg Ser Gln Ser Pro Arg Arg Arg Ser Gln Ser Arg Glu Ser
        195                 200                 205 caa tgt tcg cgg ccg caa ggc gga gga tcc gtg gac aag aaa att gtg      672
Gln Cys Ser Arg Pro Gln Gly Gly Gly Ser Val Asp Lys Lys Ile Val
210                 215                 220 ccc agg gat tgt ggt tgt aag cct tgc ata tgt aca gtc cca gaa gta      720
Pro Arg Asp Cys Gly Cys Lys Pro Cys Ile Cys Thr Val Pro Glu Val
225                 230                 235                 240 tca tct gtc ttc atc ttc ccc cca aag ccc aag gat gtg ctc acc att      768
Ser Ser Val Phe Ile Phe Pro Pro Lys Pro Lys Asp Val Leu Thr Ile
                245                 250                 255 act ctg act cct aag gtc acg tgt gtt gtg gta gac atc agc aag gat      816
Thr Leu Thr Pro Lys Val Thr Cys Val Val Val Asp Ile Ser Lys Asp
            260                 265                 270 gat ccc gag gtc cag ttc agc tgg ttt gta gat gat gtg gag gtg cac      864
Asp Pro Glu Val Gln Phe Ser Trp Phe Val Asp Asp Val Glu Val His
        275                 280                 285 aca gct cag acg caa ccc cgg gag gag cag ttc aac agc act ttc cgc      912
Thr Ala Gln Thr Gln Pro Arg Glu Glu Gln Phe Asn Ser Thr Phe Arg
    290                 295                 300 tca gtc agt gaa ctt ccc atc atg cac cag gac tgg ctc aat ggc aag      960
Ser Val Ser Glu Leu Pro Ile Met His Gln Asp Trp Leu Asn Gly Lys
305                 310                 315                 320 gag ttc aaa tgc agg gtc aac agt gca gct ttc cct gcc ccc atc gag     1008
Glu Phe Lys Cys Arg Val Asn Ser Ala Ala Phe Pro Ala Pro Ile Glu
                325                 330                 335 aaa acc atc tcc aaa acc aaa ggc aga ccg aag gct cca cag gtg tac     1056
Lys Thr Ile Ser Lys Thr Lys Gly Arg Pro Lys Ala Pro Gln Val Tyr
            340                 345                 350 acc att cca cct ccc aag gag cag atg gcc aag gat aaa gtc agt ctg     1104
Thr Ile Pro Pro Pro Lys Glu Gln Met Ala Lys Asp Lys Val Ser Leu
        355                 360                 365 acc tgc atg ata aca gac ttc ttc cct gaa gac att act gtg gag tgg     1152
Thr Cys Met Ile Thr Asp Phe Phe Pro Glu Asp Ile Thr Val Glu Trp
    370                 375                 380 cag tgg aat ggg cag cca gcg gag aac tac aag aac act cag ccc atc     1200
Gln Trp Asn Gly Gln Pro Ala Glu Asn Tyr Lys Asn Thr Gln Pro Ile
385                 390                 395                 400 atg gac aca gat ggc tct tac ttc gtc tac agc aag ctc aat gtg cag     1248
Met Asp Thr Asp Gly Ser Tyr Phe Val Tyr Ser Lys Leu Asn Val Gln
                405                 410                 415 aag agc aac tgg gag gca gga aat act ttc acc tgc tct gtg tta cat     1296
Lys Ser Asn Trp Glu Ala Gly Asn Thr Phe Thr Cys Ser Val Leu His
            420                 425                 430 gag ggc ctg cac aac cac cat act gag aag agc ctc tcc cac tct cct     1344
Glu Gly Leu His Asn His His Thr Glu Lys Ser Leu Ser His Ser Pro
        435                 440                 445 ggg ctg caa agc ttg tcg aga agt act aga gga tca taa                 1383
Gly Leu Gln Ser Leu Ser Arg Ser Thr Arg Gly Ser
    450                 455                 460
```

```
<210> SEQ ID NO 31
<211> LENGTH: 460
<212> TYPE: PRT
<213> ORGANISM: Artificial
<220> FEATURE:
<223> OTHER INFORMATION: Synthetic Construct

<400> SEQUENCE: 31

Met Ser Tyr Tyr His His His His His His Asp Tyr Asp Ile Pro Thr
1               5                   10                  15

Thr Glu Asn Leu Tyr Phe Gln Gly Ala Met Asp Ile Asp Pro Tyr Lys
            20                  25                  30

Glu Phe Gly Ala Thr Val Glu Leu Leu Ser Phe Leu Pro Ser Asp Phe
        35                  40                  45

Phe Pro Ser Val Arg Asp Leu Leu Asp Thr Ala Ser Ala Leu Tyr Arg
    50                  55                  60

Glu Ala Leu Glu Ser Pro Glu His Cys Ser Pro His His Thr Ala Leu
65                  70                  75                  80

Arg Gln Ala Ile Leu Cys Trp Gly Glu Leu Met Thr Leu Ala Thr Trp
                85                  90                  95

Val Gly Asn Asn Leu Glu Asp Pro Ala Ser Arg Asp Leu Val Val Asn
            100                 105                 110

Tyr Val Asn Thr Asn Met Gly Leu Lys Ile Arg Gln Leu Leu Trp Phe
        115                 120                 125

His Ile Ser Cys Leu Thr Phe Gly Arg Glu Thr Val Leu Glu Tyr Leu
    130                 135                 140

Val Ser Phe Gly Val Trp Ile Arg Thr Pro Pro Ala Tyr Arg Pro Pro
145                 150                 155                 160

Asn Ala Pro Ile Leu Ser Thr Leu Pro Glu Thr Thr Val Val Arg Arg
                165                 170                 175

Arg Asp Arg Gly Arg Ser Pro Arg Arg Arg Thr Pro Ser Pro Arg Arg
            180                 185                 190

Arg Arg Ser Gln Ser Pro Arg Arg Arg Ser Gln Ser Arg Glu Ser
        195                 200                 205

Gln Cys Ser Arg Pro Gln Gly Gly Ser Val Asp Lys Lys Ile Val
    210                 215                 220

Pro Arg Asp Cys Gly Cys Lys Pro Cys Ile Cys Thr Val Pro Glu Val
225                 230                 235                 240

Ser Ser Val Phe Ile Phe Pro Pro Lys Pro Lys Asp Val Leu Thr Ile
                245                 250                 255

Thr Leu Thr Pro Lys Val Thr Cys Val Val Val Asp Ile Ser Lys Asp
            260                 265                 270

Asp Pro Glu Val Gln Phe Ser Trp Phe Val Asp Val Glu Val His
        275                 280                 285

Thr Ala Gln Thr Gln Pro Arg Glu Glu Gln Phe Asn Ser Thr Phe Arg
    290                 295                 300

Ser Val Ser Glu Leu Pro Ile Met His Gln Asp Trp Leu Asn Gly Lys
305                 310                 315                 320

Glu Phe Lys Cys Arg Val Asn Ser Ala Ala Phe Pro Ala Pro Ile Glu
                325                 330                 335

Lys Thr Ile Ser Lys Thr Lys Gly Arg Pro Lys Ala Pro Gln Val Tyr
            340                 345                 350

Thr Ile Pro Pro Pro Lys Glu Gln Met Ala Lys Asp Lys Val Ser Leu
        355                 360                 365

Thr Cys Met Ile Thr Asp Phe Phe Pro Glu Asp Ile Thr Val Glu Trp
```

|                                     | 370                 | 375                 | 380                 |     |
|-------------------------------------|---------------------|---------------------|---------------------|-----|

Gln Trp Asn Gly Gln Pro Ala Glu Asn Tyr Lys Asn Thr Gln Pro Ile
385                 390                 395                 400

Met Asp Thr Asp Gly Ser Tyr Phe Val Tyr Ser Lys Leu Asn Val Gln
                405                 410                 415

Lys Ser Asn Trp Glu Ala Gly Asn Thr Phe Thr Cys Ser Val Leu His
            420                 425                 430

Glu Gly Leu His Asn His Thr Glu Lys Ser Leu Ser His Ser Pro
        435                 440                 445

Gly Leu Gln Ser Leu Ser Arg Ser Thr Arg Gly Ser
    450                 455                 460

<210> SEQ ID NO 32
<211> LENGTH: 1326
<212> TYPE: DNA
<213> ORGANISM: Artificial
<220> FEATURE:
<223> OTHER INFORMATION: Duck hepatitis B virus plus murine
<220> FEATURE:
<221> NAME/KEY: CDS
<222> LOCATION: (1)..(1326)

<400> SEQUENCE: 32

```
atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gat ccg gaa ttc atg ggg    96
Thr Glu Asn Leu Tyr Phe Gln Gly Ala Met Asp Pro Glu Phe Met Gly
                20                  25                  30 caa cat cca gca aaa tca atg gac gtc aga cgg ata gaa gga gga gaa   144
Gln His Pro Ala Lys Ser Met Asp Val Arg Arg Ile Glu Gly Gly Glu
            35                  40                  45 ata ctg tta aac caa ctt gcc gga agg atg atc cca aaa ggg act ttg   192
Ile Leu Leu Asn Gln Leu Ala Gly Arg Met Ile Pro Lys Gly Thr Leu
        50                  55                  60 aca tgg tca ggc aag ttt cca aca cta gat cac gtg tta gac cat gtg   240
Thr Trp Ser Gly Lys Phe Pro Thr Leu Asp His Val Leu Asp His Val
65                  70                  75                  80 caa aca atg gag gag ata aac acc ctc cag aat cag gga gct tgg cct   288
Gln Thr Met Glu Glu Ile Asn Thr Leu Gln Asn Gln Gly Ala Trp Pro
                85                  90                  95 gct ggg gcg gga agg aga gta gga tta tca aat ccg act cct caa gag   336
Ala Gly Ala Gly Arg Arg Val Gly Leu Ser Asn Pro Thr Pro Gln Glu
                100                 105                 110 att cct cag ccc cag tgg act ccc gag gaa gac caa aaa gca cgc gaa   384
Ile Pro Gln Pro Gln Trp Thr Pro Glu Glu Asp Gln Lys Ala Arg Glu
            115                 120                 125 gct ttt cgc cgt tat caa gaa gaa aga cca ccg gaa acc acc acc att   432
Ala Phe Arg Arg Tyr Gln Glu Glu Arg Pro Pro Glu Thr Thr Thr Ile
        130                 135                 140 cct ccg tct tcc cct cct cag tgg aag cta caa ccc ggg gac gat cca   480
Pro Pro Ser Ser Pro Pro Gln Trp Lys Leu Gln Pro Gly Asp Asp Pro
145                 150                 155                 160 ctc ctg gga aat cag tct ctc ctc gag act cat ccg cta tac cag tca   528
Leu Leu Gly Asn Gln Ser Leu Leu Glu Thr His Pro Leu Tyr Gln Ser
                165                 170                 175 gaa cca gcg gtg cca gtg ata aaa act ccc ccc ttg aag aag aaa acg   576
Glu Pro Ala Val Pro Val Ile Lys Thr Pro Pro Leu Lys Lys Lys Thr
            180                 185                 190 cgg ccg caa ggc ggc gga tcc gtg gac aag aaa att gtg ccc agg gat   624
Arg Pro Gln Gly Gly Gly Ser Val Asp Lys Lys Ile Val Pro Arg Asp
```

```
                195                 200                 205
tgt ggt tgt aag cct tgc ata tgt aca gtc cca gaa gta tca tct gtc         672
Cys Gly Cys Lys Pro Cys Ile Cys Thr Val Pro Glu Val Ser Ser Val
210                 215                 220 ttc atc ttc ccc cca aag ccc aag gat gtg ctc acc att act ctg act         720
Phe Ile Phe Pro Pro Lys Pro Lys Asp Val Leu Thr Ile Thr Leu Thr
225                 230                 235                 240 cct aag gtc acg tgt gtt gtg gta gac atc agc aag gat gat ccc gag         768
Pro Lys Val Thr Cys Val Val Val Asp Ile Ser Lys Asp Asp Pro Glu
                245                 250                 255 gtc cag ttc agc tgg ttt gta gat gat gtg gag gtg cac aca gct cag         816
Val Gln Phe Ser Trp Phe Val Asp Asp Val Glu Val His Thr Ala Gln
            260                 265                 270 acg caa ccc cgg gag gag cag ttc aac agc act ttc cgc tca gtc agt         864
Thr Gln Pro Arg Glu Glu Gln Phe Asn Ser Thr Phe Arg Ser Val Ser
        275                 280                 285 gaa ctt ccc atc atg cac cag gac tgg ctc aat ggc aag gag ttc aaa         912
Glu Leu Pro Ile Met His Gln Asp Trp Leu Asn Gly Lys Glu Phe Lys
    290                 295                 300 tgc agg gtc aac agt gca gct ttc cct gcc ccc atc gag aaa acc atc         960
Cys Arg Val Asn Ser Ala Ala Phe Pro Ala Pro Ile Glu Lys Thr Ile
305                 310                 315                 320 tcc aaa acc aaa ggc aga ccg aag gct cca cag gtg tac acc att cca        1008
Ser Lys Thr Lys Gly Arg Pro Lys Ala Pro Gln Val Tyr Thr Ile Pro
                325                 330                 335 cct ccc aag gag cag atg gcc aag gat aaa gtc agt ctg acc tgc atg        1056
Pro Pro Lys Glu Gln Met Ala Lys Asp Lys Val Ser Leu Thr Cys Met
            340                 345                 350 ata aca gac ttc ttc cct gaa gac att act gtg gag tgg cag tgg aat        1104
Ile Thr Asp Phe Phe Pro Glu Asp Ile Thr Val Glu Trp Gln Trp Asn
        355                 360                 365 ggg cag cca gcg gag aac tac aag aac act cag ccc atc atg gac aca        1152
Gly Gln Pro Ala Glu Asn Tyr Lys Asn Thr Gln Pro Ile Met Asp Thr
    370                 375                 380 gat ggc tct tac ttc gtc tac agc aag ctc aat gtg cag aag agc aac        1200
Asp Gly Ser Tyr Phe Val Tyr Ser Lys Leu Asn Val Gln Lys Ser Asn
385                 390                 395                 400 tgg gag gca gga aat act ttc acc tgc tct gtg tta cat gag ggc ctg        1248
Trp Glu Ala Gly Asn Thr Phe Thr Cys Ser Val Leu His Glu Gly Leu
                405                 410                 415 cac aac cac cat act gag aag agc ctc tcc cac tct cct ggg ctg caa        1296
His Asn His His Thr Glu Lys Ser Leu Ser His Ser Pro Gly Leu Gln
            420                 425                 430 agc ttg tcg aga agt act aga gga tca taa                                1326
Ser Leu Ser Arg Ser Thr Arg Gly Ser
        435                 440

<210> SEQ ID NO 33
<211> LENGTH: 441
<212> TYPE: PRT
<213> ORGANISM: Artificial
<220> FEATURE:
<223> OTHER INFORMATION: Synthetic Construct

<400> SEQUENCE: 33

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Gly
            20                  25                  30

Gln His Pro Ala Lys Ser Met Asp Val Arg Arg Ile Glu Gly Gly Glu
        35                  40                  45
```

```
Ile Leu Leu Asn Gln Leu Ala Gly Arg Met Ile Pro Lys Gly Thr Leu
 50                  55                  60

Thr Trp Ser Gly Lys Phe Pro Thr Leu Asp His Val Leu Asp His Val
65                  70                  75                  80

Gln Thr Met Glu Glu Ile Asn Thr Leu Gln Asn Gln Gly Ala Trp Pro
                 85                  90                  95

Ala Gly Ala Gly Arg Arg Val Gly Leu Ser Asn Pro Thr Pro Gln Glu
            100                 105                 110

Ile Pro Gln Pro Gln Trp Thr Pro Glu Glu Asp Gln Lys Ala Arg Glu
        115                 120                 125

Ala Phe Arg Arg Tyr Gln Glu Glu Arg Pro Pro Glu Thr Thr Thr Ile
    130                 135                 140

Pro Pro Ser Ser Pro Pro Gln Trp Lys Leu Gln Pro Gly Asp Asp Pro
145                 150                 155                 160

Leu Leu Gly Asn Gln Ser Leu Leu Glu Thr His Pro Leu Tyr Gln Ser
                165                 170                 175

Glu Pro Ala Val Pro Val Ile Lys Thr Pro Pro Leu Lys Lys Lys Thr
            180                 185                 190

Arg Pro Gln Gly Gly Gly Ser Val Asp Lys Lys Ile Val Pro Arg Asp
        195                 200                 205

Cys Gly Cys Lys Pro Cys Ile Cys Thr Val Pro Glu Val Ser Ser Val
210                 215                 220

Phe Ile Phe Pro Pro Lys Pro Lys Asp Val Leu Thr Ile Thr Leu Thr
225                 230                 235                 240

Pro Lys Val Thr Cys Val Val Asp Ile Ser Lys Asp Asp Pro Glu
                245                 250                 255

Val Gln Phe Ser Trp Phe Val Asp Asp Val Glu Val His Thr Ala Gln
            260                 265                 270

Thr Gln Pro Arg Glu Glu Gln Phe Asn Ser Thr Phe Arg Ser Val Ser
        275                 280                 285

Glu Leu Pro Ile Met His Gln Asp Trp Leu Asn Gly Lys Glu Phe Lys
    290                 295                 300

Cys Arg Val Asn Ser Ala Ala Phe Pro Ala Pro Ile Glu Lys Thr Ile
305                 310                 315                 320

Ser Lys Thr Lys Gly Arg Pro Lys Ala Pro Gln Val Tyr Thr Ile Pro
                325                 330                 335

Pro Pro Lys Glu Gln Met Ala Lys Asp Lys Val Ser Leu Thr Cys Met
            340                 345                 350

Ile Thr Asp Phe Phe Pro Glu Asp Ile Thr Val Glu Trp Gln Trp Asn
        355                 360                 365

Gly Gln Pro Ala Glu Asn Tyr Lys Asn Thr Gln Pro Ile Met Asp Thr
    370                 375                 380

Asp Gly Ser Tyr Phe Val Tyr Ser Lys Leu Asn Val Gln Lys Ser Asn
385                 390                 395                 400

Trp Glu Ala Gly Asn Thr Phe Thr Cys Ser Val Leu His Glu Gly Leu
                405                 410                 415

His Asn His His Thr Glu Lys Ser Leu Ser His Ser Pro Gly Leu Gln
            420                 425                 430

Ser Leu Ser Arg Ser Thr Arg Gly Ser
        435                 440

<210> SEQ ID NO 34
<211> LENGTH: 1827
<212> TYPE: DNA
```

<210> ORGANISM: Artificial
<220> FEATURE:
<223> OTHER INFORMATION: Duck hepatitis B virus plus murine
<220> FEATURE:
<221> NAME/KEY: CDS
<222> LOCATION: (1)..(1824)

<400> SEQUENCE: 34

```
atg tcg tac tac cat cac cat cac cat cac gat tac gat atc cca acg      48
Met Ser Tyr Tyr His His His His His His Asp Tyr Asp Ile Pro Thr
 1               5                  10                  15 acc gaa aac ctg tat ttt cag ggc gcc atg gat ccg gaa ttc atg ggg      96
Thr Glu Asn Leu Tyr Phe Gln Gly Ala Met Asp Pro Glu Phe Met Gly
                20                  25                  30 caa cat cca gca aaa tca atg gac gtc aga cgg ata gaa gga gga gaa    144
Gln His Pro Ala Lys Ser Met Asp Val Arg Arg Ile Glu Gly Gly Glu
            35                  40                  45 ata ctg tta aac caa ctt gcc gga agg atg atc cca aaa ggg act ttg    192
Ile Leu Leu Asn Gln Leu Ala Gly Arg Met Ile Pro Lys Gly Thr Leu
        50                  55                  60 aca tgg tca ggc aag ttt cca aca cta gat cac gtg tta gac cat gtg    240
Thr Trp Ser Gly Lys Phe Pro Thr Leu Asp His Val Leu Asp His Val
65                  70                  75                  80 caa aca atg gag gag ata aac acc ctc cag aat cag gga gct tgg cct    288
Gln Thr Met Glu Glu Ile Asn Thr Leu Gln Asn Gln Gly Ala Trp Pro
                85                  90                  95 gct ggg gcg gga agg aga gta gga tta tca aat ccg act cct caa gag    336
Ala Gly Ala Gly Arg Arg Val Gly Leu Ser Asn Pro Thr Pro Gln Glu
                100                 105                 110 att cct cag ccc cag tgg act ccc gag gaa gac caa aaa gca cgc gaa    384
Ile Pro Gln Pro Gln Trp Thr Pro Glu Glu Asp Gln Lys Ala Arg Glu
            115                 120                 125 gct ttt cgc cgt tat caa gaa gaa aga cca ccg gaa acc acc acc att    432
Ala Phe Arg Arg Tyr Gln Glu Glu Arg Pro Pro Glu Thr Thr Thr Ile
130                 135                 140 cct ccg tct tcc cct cct cag tgg aag cta caa ccc ggg gac gat cca    480
Pro Pro Ser Ser Pro Pro Gln Trp Lys Leu Gln Pro Gly Asp Asp Pro
145                 150                 155                 160 ctc ctg gga aat cag tct ctc ctc gag act cat ccg cta tac cag tca    528
Leu Leu Gly Asn Gln Ser Leu Leu Glu Thr His Pro Leu Tyr Gln Ser
                165                 170                 175 gaa cca gcg gtg cca gtg ata aaa act ccc ccc ttg aag aag aaa atg    576
Glu Pro Ala Val Pro Val Ile Lys Thr Pro Pro Leu Lys Lys Lys Met
                180                 185                 190 tct ggt acc ttc ggg gga ata cta gct ggc cta atc gga tta ctg gta    624
Ser Gly Thr Phe Gly Gly Ile Leu Ala Gly Leu Ile Gly Leu Leu Val
            195                 200                 205 agc ttt ttc ttg ttg ata aaa att cta gaa ata ctg agg agg cta gat    672
Ser Phe Phe Leu Leu Ile Lys Ile Leu Glu Ile Leu Arg Arg Leu Asp
210                 215                 220 tgg tgg tgg att tct ctc agt tct cca aag gga aaa atg caa tgc gct    720
Trp Trp Trp Ile Ser Leu Ser Ser Pro Lys Gly Lys Met Gln Cys Ala
225                 230                 235                 240 ttc caa gat act gga gcc caa atc tct cca cat tac gta gga tct tgc    768
Phe Gln Asp Thr Gly Ala Gln Ile Ser Pro His Tyr Val Gly Ser Cys
                245                 250                 255 ccg tgg gga tgc cca gga ttt ctt tgg acc tat ctc agg ctt ttt atc    816
Pro Trp Gly Cys Pro Gly Phe Leu Trp Thr Tyr Leu Arg Leu Phe Ile
                260                 265                 270 atc ttc ctc tta atc ctg cta gta gca gca ggc ttg ctg tat ctg acg    864
Ile Phe Leu Leu Ile Leu Leu Val Ala Ala Gly Leu Leu Tyr Leu Thr
            275                 280                 285
```

```
gac aac ggg tct act att tta gga aag ctc caa tgg gcg tcg gtc tca        912
Asp Asn Gly Ser Thr Ile Leu Gly Lys Leu Gln Trp Ala Ser Val Ser
    290                 295                 300 gcc ctt ttc tcc tcc atc tct tca cta ctg ccc tcg gat ccg aaa tct        960
Ala Leu Phe Ser Ser Ile Ser Ser Leu Leu Pro Ser Asp Pro Lys Ser
305                 310                 315                 320 ctc gtc gct tta acg ttt gga ctt tca ctt ata tgg atg act tcc tcc       1008
Leu Val Ala Leu Thr Phe Gly Leu Ser Leu Ile Trp Met Thr Ser Ser
                325                 330                 335 tct gcc acc caa acg ctc gtc acc tta acg caa tta gcc acg ctg tct       1056
Ser Ala Thr Gln Thr Leu Val Thr Leu Thr Gln Leu Ala Thr Leu Ser
        340                 345                 350 gct ctt ttt tac aag agt tcg cgg ccg caa ggc ggc gga tcc gtg gac       1104
Ala Leu Phe Tyr Lys Ser Ser Arg Pro Gln Gly Gly Gly Ser Val Asp
            355                 360                 365 aaa aaa att gtg ccc agg gat tgt ggt tgt aag cct tgc ata tgt aca       1152
Lys Lys Ile Val Pro Arg Asp Cys Gly Cys Lys Pro Cys Ile Cys Thr
370                 375                 380 gtc cca gaa gta tca tct gtc ttc atc ttc ccc cca aag ccc aag gat       1200
Val Pro Glu Val Ser Ser Val Phe Ile Phe Pro Pro Lys Pro Lys Asp
385                 390                 395                 400 gtg ctc acc att act ctg act cct aag gtc acg tgt gtt gtg gta gac       1248
Val Leu Thr Ile Thr Leu Thr Pro Lys Val Thr Cys Val Val Val Asp
                405                 410                 415 atc agc aag gat gat ccc gag gtc cag ttc agc tgg ttt gta gat gat       1296
Ile Ser Lys Asp Asp Pro Glu Val Gln Phe Ser Trp Phe Val Asp Asp
        420                 425                 430 gtg gag gtg cac aca gct cag acg caa ccc cgg gag gag cag ttc aac       1344
Val Glu Val His Thr Ala Gln Thr Gln Pro Arg Glu Glu Gln Phe Asn
            435                 440                 445 agc act ttc cgc tca gtc agt gaa ctt ccc atc atg cac cag gac tgg       1392
Ser Thr Phe Arg Ser Val Ser Glu Leu Pro Ile Met His Gln Asp Trp
450                 455                 460 ctc aat ggc aag gag ttc aaa tgc agg gtc aac agt gca gct ttc cct       1440
Leu Asn Gly Lys Glu Phe Lys Cys Arg Val Asn Ser Ala Ala Phe Pro
465                 470                 475                 480 gcc ccc atc gag aaa acc atc tcc aaa acc aaa ggc aga ccg aag gct       1488
Ala Pro Ile Glu Lys Thr Ile Ser Lys Thr Lys Gly Arg Pro Lys Ala
                485                 490                 495 cca cag gtg tac acc att cca cct ccc aag gag cag atg gcc aag gat       1536
Pro Gln Val Tyr Thr Ile Pro Pro Pro Lys Glu Gln Met Ala Lys Asp
        500                 505                 510 aaa gtc agt ctg acc tgc atg ata aca gac ttc ttc cct gaa gac att       1584
Lys Val Ser Leu Thr Cys Met Ile Thr Asp Phe Phe Pro Glu Asp Ile
            515                 520                 525 act gtg gag tgg cag tgg aat ggg cag cca gcg gag aac tac aag aac       1632
Thr Val Glu Trp Gln Trp Asn Gly Gln Pro Ala Glu Asn Tyr Lys Asn
530                 535                 540 act cag ccc atc atg gac aca gat ggc tct tac ttc gtc tac agc aag       1680
Thr Gln Pro Ile Met Asp Thr Asp Gly Ser Tyr Phe Val Tyr Ser Lys
545                 550                 555                 560 ctc aat gtg cag aag agc aac tgg gag gca gga aat act ttc acc tgc       1728
Leu Asn Val Gln Lys Ser Asn Trp Glu Ala Gly Asn Thr Phe Thr Cys
                565                 570                 575 tct gtg tta cat gag ggc ctg cac aac cac cat act gag aag agc ctc       1776
Ser Val Leu His Glu Gly Leu His Asn His His Thr Glu Lys Ser Leu
        580                 585                 590 tcc cac tct cct ggg ctg caa agc ttg tcg aga agt act aga gga tca       1824
Ser His Ser Pro Gly Leu Gln Ser Leu Ser Arg Ser Thr Arg Gly Ser
            595                 600                 605
``` taa 1827

<210> SEQ ID NO 35
<211> LENGTH: 608
<212> TYPE: PRT
<213> ORGANISM: Artificial
<220> FEATURE:
<223> OTHER INFORMATION: Synthetic Construct

<400> SEQUENCE: 35

```
Met Ser Tyr Tyr His His His His His His Asp Tyr Asp Ile Pro Thr
 1               5                  10                  15

Thr Glu Asn Leu Tyr Phe Gln Gly Ala Met Asp Pro Glu Phe Met Gly
                20                  25                  30

Gln His Pro Ala Lys Ser Met Asp Val Arg Arg Ile Glu Gly Gly Glu
            35                  40                  45

Ile Leu Leu Asn Gln Leu Ala Gly Arg Met Ile Pro Lys Gly Thr Leu
        50                  55                  60

Thr Trp Ser Gly Lys Phe Pro Thr Leu Asp His Val Leu Asp His Val
 65                  70                  75                  80

Gln Thr Met Glu Glu Ile Asn Thr Leu Gln Asn Gln Gly Ala Trp Pro
                85                  90                  95

Ala Gly Ala Gly Arg Arg Val Gly Leu Ser Asn Pro Thr Pro Gln Glu
            100                 105                 110

Ile Pro Gln Pro Gln Trp Thr Pro Glu Glu Asp Gln Lys Ala Arg Glu
        115                 120                 125

Ala Phe Arg Arg Tyr Gln Glu Glu Arg Pro Pro Glu Thr Thr Thr Ile
    130                 135                 140

Pro Pro Ser Ser Pro Pro Gln Trp Lys Leu Gln Pro Gly Asp Asp Pro
145                 150                 155                 160

Leu Leu Gly Asn Gln Ser Leu Leu Glu Thr His Pro Leu Tyr Gln Ser
                165                 170                 175

Glu Pro Ala Val Pro Val Ile Lys Thr Pro Pro Leu Lys Lys Lys Met
            180                 185                 190

Ser Gly Thr Phe Gly Gly Ile Leu Ala Gly Leu Ile Gly Leu Leu Val
        195                 200                 205

Ser Phe Phe Leu Leu Ile Lys Ile Leu Glu Ile Leu Arg Arg Leu Asp
    210                 215                 220

Trp Trp Trp Ile Ser Leu Ser Ser Pro Lys Gly Lys Met Gln Cys Ala
225                 230                 235                 240

Phe Gln Asp Thr Gly Ala Gln Ile Ser Pro His Tyr Val Gly Ser Cys
                245                 250                 255

Pro Trp Gly Cys Pro Gly Phe Leu Trp Thr Tyr Leu Arg Leu Phe Ile
            260                 265                 270

Ile Phe Leu Leu Ile Leu Leu Val Ala Ala Gly Leu Leu Tyr Leu Thr
        275                 280                 285

Asp Asn Gly Ser Thr Ile Leu Gly Lys Leu Gln Trp Ala Ser Val Ser
    290                 295                 300

Ala Leu Phe Ser Ser Ile Ser Ser Leu Leu Pro Ser Asp Pro Lys Ser
305                 310                 315                 320

Leu Val Ala Leu Thr Phe Gly Leu Ser Leu Ile Trp Met Thr Ser Ser
                325                 330                 335

Ser Ala Thr Gln Thr Leu Val Thr Leu Thr Gln Leu Ala Thr Leu Ser
            340                 345                 350

Ala Leu Phe Tyr Lys Ser Ser Arg Pro Gln Gly Gly Gly Ser Val Asp
```

```
                355                 360                 365
Lys Lys Ile Val Pro Arg Asp Cys Gly Cys Lys Pro Cys Ile Cys Thr
        370                 375                 380

Val Pro Glu Val Ser Ser Val Phe Ile Phe Pro Lys Pro Lys Asp
385                 390                 395                 400

Val Leu Thr Ile Thr Leu Thr Pro Lys Val Thr Cys Val Val Asp
                405                 410                 415

Ile Ser Lys Asp Asp Pro Glu Val Gln Phe Ser Trp Phe Val Asp
        420                 425                 430

Val Glu Val His Thr Ala Gln Thr Gln Pro Arg Glu Glu Gln Phe Asn
                435                 440                 445

Ser Thr Phe Arg Ser Val Ser Glu Leu Pro Ile Met His Gln Asp Trp
        450                 455                 460

Leu Asn Gly Lys Glu Phe Lys Cys Arg Val Asn Ser Ala Ala Phe Pro
465                 470                 475                 480

Ala Pro Ile Glu Lys Thr Ile Ser Lys Thr Lys Gly Arg Pro Lys Ala
                485                 490                 495

Pro Gln Val Tyr Thr Ile Pro Pro Lys Glu Gln Met Ala Lys Asp
                500                 505                 510

Lys Val Ser Leu Thr Cys Met Ile Thr Asp Phe Phe Pro Glu Asp Ile
        515                 520                 525

Thr Val Glu Trp Gln Trp Asn Gly Gln Pro Ala Glu Asn Tyr Lys Asn
530                 535                 540

Thr Gln Pro Ile Met Asp Thr Asp Gly Ser Tyr Phe Val Tyr Ser Lys
545                 550                 555                 560

Leu Asn Val Gln Lys Ser Asn Trp Glu Ala Gly Asn Thr Phe Thr Cys
                565                 570                 575

Ser Val Leu His Glu Gly Leu His Asn His His Thr Glu Lys Ser Leu
        580                 585                 590

Ser His Ser Pro Gly Leu Gln Ser Leu Ser Arg Ser Thr Arg Gly Ser
        595                 600                 605

<210> SEQ ID NO 36
<211> LENGTH: 1614
<212> TYPE: DNA
<213> ORGANISM: Artificial
<220> FEATURE:
<223> OTHER INFORMATION: Duck hepatitis B virus plus murine
<220> FEATURE:
<221> NAME/KEY: CDS
<222> LOCATION: (1)..(1614)

<400> SEQUENCE: 36 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat atc aat gct tct aga      96
Thr Glu Asn Leu Tyr Phe Gln Gly Ala Met Asp Ile Asn Ala Ser Arg
            20                  25                  30 gcc tta gcc aat gtg tat gat cta cca gat gat ttc ttt cca aaa ata     144
Ala Leu Ala Asn Val Tyr Asp Leu Pro Asp Asp Phe Phe Pro Lys Ile
        35                  40                  45 gat gat ctt gtt aga gat gct aaa gac gct tta gag cct tat tgg aaa     192
Asp Asp Leu Val Arg Asp Ala Lys Asp Ala Leu Glu Pro Tyr Trp Lys
    50                  55                  60 tca gat tca ata aag aaa cat gtt ttg att gca act cac ttt gtg gat     240
Ser Asp Ser Ile Lys Lys His Val Leu Ile Ala Thr His Phe Val Asp
65                  70                  75                  80
```

```
ctc att gaa gac ttc tgg cag act aca cag ggc atg cat gaa ata gcc    288
Leu Ile Glu Asp Phe Trp Gln Thr Thr Gln Gly Met His Glu Ile Ala
             85                  90                  95 gaa tca tta aga gct gtt ata cct ccc act act act cct gtt cca ccg    336
Glu Ser Leu Arg Ala Val Ile Pro Pro Thr Thr Thr Pro Val Pro Pro
            100                 105                 110 ggt tat ctt att cag cac gag gaa gct gaa gag ata cct ttg gga gat    384
Gly Tyr Leu Ile Gln His Glu Glu Ala Glu Glu Ile Pro Leu Gly Asp
            115                 120                 125 tta ttt aaa cac caa gaa gaa agg ata gta agt ttc caa ccc gac tat    432
Leu Phe Lys His Gln Glu Glu Arg Ile Val Ser Phe Gln Pro Asp Tyr
130                 135                 140 ccg att acg gct aga att cat gct cat ttg aaa gct tat gca aaa att    480
Pro Ile Thr Ala Arg Ile His Ala His Leu Lys Ala Tyr Ala Lys Ile
145                 150                 155                 160 aac gag gaa tca ctg gat agg gct agg aga ttg ctt tgg tgg cat tac    528
Asn Glu Glu Ser Leu Asp Arg Ala Arg Arg Leu Leu Trp Trp His Tyr
                165                 170                 175 aac tgt tta ctg tgg gga gaa gct caa gtt act aac tat att tct cgt    576
Asn Cys Leu Leu Trp Gly Glu Ala Gln Val Thr Asn Tyr Ile Ser Arg
                180                 185                 190 ttg cgt act tgg ttg tca act cct gag aaa tat aga ggt aga gat gcc    624
Leu Arg Thr Trp Leu Ser Thr Pro Glu Lys Tyr Arg Gly Arg Asp Ala
                195                 200                 205 ccg acc att gaa gca atc act aga cca atc cag gtg gct cag gga ggc    672
Pro Thr Ile Glu Ala Ile Thr Arg Pro Ile Gln Val Ala Gln Gly Gly
            210                 215                 220 aga aaa aca act acg ggt act aga aaa cct cgt gga ctc gaa cct aga    720
Arg Lys Thr Thr Thr Gly Thr Arg Lys Pro Arg Gly Leu Glu Pro Arg
225                 230                 235                 240 aga aga aaa gtt aaa acc aca gtt gtc tat ggg aga aga cgt tca aag    768
Arg Arg Lys Val Lys Thr Thr Val Val Tyr Gly Arg Arg Arg Ser Lys
                245                 250                 255 tcc cgg gaa agg aga gcc cct aca ccc caa cgt gcg ggc tcc cct ctc    816
Ser Arg Glu Arg Arg Ala Pro Thr Pro Gln Arg Ala Gly Ser Pro Leu
                260                 265                 270 cca cgt agt tcg agc agc cac cat aga tct ccc tcg cct agg aaa tcg    864
Pro Arg Ser Ser Ser Ser His His Arg Ser Pro Ser Pro Arg Lys Ser
            275                 280                 285 cgg ccg caa ggc ggc gga tcc gtg gac aag aaa att gtg ccc agg gat    912
Arg Pro Gln Gly Gly Gly Ser Val Asp Lys Lys Ile Val Pro Arg Asp
290                 295                 300 tgt ggt tgt aag cct tgc ata tgt aca gtc cca gaa gta tca tct gtc    960
Cys Gly Cys Lys Pro Cys Ile Cys Thr Val Pro Glu Val Ser Ser Val
305                 310                 315                 320 ttc atc ttc ccc cca aag ccc aag gat gtg ctc acc att act ctg act    1008
Phe Ile Phe Pro Pro Lys Pro Lys Asp Val Leu Thr Ile Thr Leu Thr
                325                 330                 335 cct aag gtc acg tgt gtt gtg gta gac atc agc aag gat gat ccc gag    1056
Pro Lys Val Thr Cys Val Val Val Asp Ile Ser Lys Asp Asp Pro Glu
                340                 345                 350 gtc cag ttc agc tgg ttt gta gat gat gtg gag gtg cac aca gct cag    1104
Val Gln Phe Ser Trp Phe Val Asp Asp Val Glu Val His Thr Ala Gln
            355                 360                 365 acg caa ccc cgg gag gag cag ttc aac agc act ttc cgc tca gtc agt    1152
Thr Gln Pro Arg Glu Glu Gln Phe Asn Ser Thr Phe Arg Ser Val Ser
370                 375                 380 gaa ctt ccc atc atg cac cag gac tgg ctc aat ggc aag gag ttc aaa    1200
Glu Leu Pro Ile Met His Gln Asp Trp Leu Asn Gly Lys Glu Phe Lys
385                 390                 395                 400
```

-continued

```
tgc agg gtc aac agt gca gct ttc cct gcc ccc atc gag aaa acc atc      1248
Cys Arg Val Asn Ser Ala Ala Phe Pro Ala Pro Ile Glu Lys Thr Ile
            405                 410                 415 tcc aaa acc aaa ggc aga ccg aag gct cca cag gtg tac acc att cca      1296
Ser Lys Thr Lys Gly Arg Pro Lys Ala Pro Gln Val Tyr Thr Ile Pro
        420                 425                 430 cct ccc aag gag cag atg gcc aag gat aaa gtc agt ctg acc tgc atg      1344
Pro Pro Lys Glu Gln Met Ala Lys Asp Lys Val Ser Leu Thr Cys Met
    435                 440                 445 ata aca gac ttc ttc cct gaa gac att act gtg gag tgg cag tgg aat      1392
Ile Thr Asp Phe Phe Pro Glu Asp Ile Thr Val Glu Trp Gln Trp Asn
450                 455                 460 ggg cag cca gcg gag aac tac aag aac act cag ccc atc atg gac aca      1440
Gly Gln Pro Ala Glu Asn Tyr Lys Asn Thr Gln Pro Ile Met Asp Thr
465                 470                 475                 480 gat ggc tct tac ttc gtc tac agc aag ctc aat gtg cag aag agc aac      1488
Asp Gly Ser Tyr Phe Val Tyr Ser Lys Leu Asn Val Gln Lys Ser Asn
                485                 490                 495 tgg gag gca gga aat act ttc acc tgc tct gtg tta cat gag ggc ctg      1536
Trp Glu Ala Gly Asn Thr Phe Thr Cys Ser Val Leu His Glu Gly Leu
            500                 505                 510 cac aac cac cat act gag aag agc ctc tcc cac tct cct ggg ctg caa      1584
His Asn His His Thr Glu Lys Ser Leu Ser His Ser Pro Gly Leu Gln
        515                 520                 525 agc ttg tcg aga agt act aga gga tca taa                              1614
Ser Leu Ser Arg Ser Thr Arg Gly Ser
    530                 535

<210> SEQ ID NO 37
<211> LENGTH: 537
<212> TYPE: PRT
<213> ORGANISM: Artificial
<220> FEATURE:
<223> OTHER INFORMATION: Synthetic Construct

<400> SEQUENCE: 37

Met Ser Tyr Tyr His His His His His Asp Tyr Asp Ile Pro Thr
1               5                   10                  15

Thr Glu Asn Leu Tyr Phe Gln Gly Ala Met Asp Ile Asn Ala Ser Arg
            20                  25                  30

Ala Leu Ala Asn Val Tyr Asp Leu Pro Asp Asp Phe Phe Pro Lys Ile
        35                  40                  45

Asp Asp Leu Val Arg Asp Ala Lys Asp Ala Leu Glu Pro Tyr Trp Lys
    50                  55                  60

Ser Asp Ser Ile Lys Lys His Val Leu Ile Ala Thr His Phe Val Asp
65                  70                  75                  80

Leu Ile Glu Asp Phe Trp Gln Thr Thr Gln Gly Met His Glu Ile Ala
                85                  90                  95

Glu Ser Leu Arg Ala Val Ile Pro Pro Thr Thr Thr Pro Val Pro Pro
            100                 105                 110

Gly Tyr Leu Ile Gln His Glu Glu Ala Glu Glu Ile Pro Leu Gly Asp
        115                 120                 125

Leu Phe Lys His Gln Glu Glu Arg Ile Val Ser Phe Gln Pro Asp Tyr
    130                 135                 140

Pro Ile Thr Ala Arg Ile His Ala His Leu Lys Ala Tyr Ala Lys Ile
145                 150                 155                 160

Asn Glu Glu Ser Leu Asp Arg Ala Arg Arg Leu Leu Trp Trp His Tyr
                165                 170                 175

Asn Cys Leu Leu Trp Gly Glu Ala Gln Val Thr Asn Tyr Ile Ser Arg
```

```
                    180                 185                 190
Leu Arg Thr Trp Leu Ser Thr Pro Glu Lys Tyr Arg Gly Arg Asp Ala
        195                 200                 205

Pro Thr Ile Glu Ala Ile Thr Arg Pro Ile Gln Val Ala Gln Gly Gly
210                 215                 220

Arg Lys Thr Thr Thr Gly Thr Arg Lys Pro Arg Gly Leu Glu Pro Arg
225                 230                 235                 240

Arg Arg Lys Val Lys Thr Thr Val Val Tyr Gly Arg Arg Ser Lys
                    245                 250                 255

Ser Arg Glu Arg Arg Ala Pro Thr Pro Gln Arg Ala Gly Ser Pro Leu
        260                 265                 270

Pro Arg Ser Ser Ser His His Arg Ser Pro Ser Pro Arg Lys Ser
                    275                 280                 285

Arg Pro Gln Gly Gly Gly Ser Val Asp Lys Lys Ile Val Pro Arg Asp
        290                 295                 300

Cys Gly Cys Lys Pro Cys Ile Cys Thr Val Pro Glu Val Ser Ser Val
305                 310                 315                 320

Phe Ile Phe Pro Pro Lys Pro Lys Asp Val Leu Thr Ile Thr Leu Thr
                    325                 330                 335

Pro Lys Val Thr Cys Val Val Val Asp Ile Ser Lys Asp Asp Pro Glu
        340                 345                 350

Val Gln Phe Ser Trp Phe Val Asp Asp Val Glu Val His Thr Ala Gln
                    355                 360                 365

Thr Gln Pro Arg Glu Glu Gln Phe Asn Ser Thr Phe Arg Ser Val Ser
        370                 375                 380

Glu Leu Pro Ile Met His Gln Asp Trp Leu Asn Gly Lys Glu Phe Lys
385                 390                 395                 400

Cys Arg Val Asn Ser Ala Ala Phe Pro Ala Pro Ile Glu Lys Thr Ile
                    405                 410                 415

Ser Lys Thr Lys Gly Arg Pro Lys Ala Pro Gln Val Tyr Thr Ile Pro
        420                 425                 430

Pro Pro Lys Glu Gln Met Ala Lys Asp Lys Val Ser Leu Thr Cys Met
        435                 440                 445

Ile Thr Asp Phe Phe Pro Glu Asp Ile Thr Val Glu Trp Gln Trp Asn
450                 455                 460

Gly Gln Pro Ala Glu Asn Tyr Lys Asn Thr Gln Pro Ile Met Asp Thr
465                 470                 475                 480

Asp Gly Ser Tyr Phe Val Tyr Ser Lys Leu Asn Val Gln Lys Ser Asn
                    485                 490                 495

Trp Glu Ala Gly Asn Thr Phe Thr Cys Ser Val Leu His Glu Gly Leu
                500                 505                 510

His Asn His His Thr Glu Lys Ser Leu Ser His Ser Pro Gly Leu Gln
        515                 520                 525

Ser Leu Ser Arg Ser Thr Arg Gly Ser
        530                 535

<210> SEQ ID NO 38
<211> LENGTH: 1422
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1422)

<400> SEQUENCE: 38
```

```
atg tcg tac tac cat cac cat cac cat gat tac gat atc cca acg      48
Met Ser Tyr Tyr His His His His His Asp Tyr Asp Ile Pro Thr
 1               5                  10                  15 acc gaa aac ctg tat ttt cag ggc gcc atg gat ccg gaa ttc atg agc  96
Thr Glu Asn Leu Tyr Phe Gln Gly Ala Met Asp Pro Glu Phe Met Ser
                 20                  25                  30 acg aat cct aaa cct caa aga aaa acc aaa cgt aac acc aac cgt cgc 144
Thr Asn Pro Lys Pro Gln Arg Lys Thr Lys Arg Asn Thr Asn Arg Arg
             35                  40                  45 cca cag gac gtc aag ttc ccg ggt ggc ggt cag atc gtt ggt gga gtt 192
Pro Gln Asp Val Lys Phe Pro Gly Gly Gly Gln Ile Val Gly Gly Val
         50                  55                  60 tac ttg ttg ccg cgc agg ggc cct aga ttg ggt gtg cgc gcg acg agg 240
Tyr Leu Leu Pro Arg Arg Gly Pro Arg Leu Gly Val Arg Ala Thr Arg
65                  70                  75                  80 aag act tcc gag cgg tcg caa cct cga ggt aga cgt cag cct atc ccc 288
Lys Thr Ser Glu Arg Ser Gln Pro Arg Gly Arg Arg Gln Pro Ile Pro
                 85                  90                  95 aag gca cgt cgg ccc gag ggc agg acc tgg gct cag ccc ggg tac cct 336
Lys Ala Arg Arg Pro Glu Gly Arg Thr Trp Ala Gln Pro Gly Tyr Pro
            100                 105                 110 tgg ccc ctc tat ggc aat gag ggt tgc ggg tgg gcg gga tgg ctc ctg 384
Trp Pro Leu Tyr Gly Asn Glu Gly Cys Gly Trp Ala Gly Trp Leu Leu
        115                 120                 125 tct ccc cgt ggc tct cgg cct agc tgg ggc ccc aca gac ccc cgg cgt 432
Ser Pro Arg Gly Ser Arg Pro Ser Trp Gly Pro Thr Asp Pro Arg Arg
130                 135                 140 agg tcg cgc aat ttg ggt aag gtc atc gat acc ctt acg tgc ggc ttc 480
Arg Ser Arg Asn Leu Gly Lys Val Ile Asp Thr Leu Thr Cys Gly Phe
145                 150                 155                 160 gcc gac ctc atg ggg tac ata ccg ctc gtc ggc gcc cct ctt gga ggc 528
Ala Asp Leu Met Gly Tyr Ile Pro Leu Val Gly Ala Pro Leu Gly Gly
                165                 170                 175 gct gcc agg gcc ctg gcg cat ggc gtc cgg gtt ctg gaa gac ggc gtg 576
Ala Ala Arg Ala Leu Ala His Gly Val Arg Val Leu Glu Asp Gly Val
            180                 185                 190 aac tat gca aca ggg aac ctt cct ggt tgc tct ttc tct atc ttc ctt 624
Asn Tyr Ala Thr Gly Asn Leu Pro Gly Cys Ser Phe Ser Ile Phe Leu
        195                 200                 205 ctg gcc ctg ctc tct tgc ctg act gtg ccc gct tca gcc gga cta gtg 672
Leu Ala Leu Leu Ser Cys Leu Thr Val Pro Ala Ser Ala Gly Leu Val
210                 215                 220 cgg ccg caa ggc ggc gga tcc gtg gac aag aaa att gtg ccc agg gat 720
Arg Pro Gln Gly Gly Gly Ser Val Asp Lys Lys Ile Val Pro Arg Asp
225                 230                 235                 240 tgt ggt tgt aag cct tgc ata tgt aca gtc cca gaa gta tca tct gtc 768
Cys Gly Cys Lys Pro Cys Ile Cys Thr Val Pro Glu Val Ser Ser Val
                245                 250                 255 ttc atc ttc ccc cca aag ccc aag gat gtg ctc acc att act ctg act 816
Phe Ile Phe Pro Pro Lys Pro Lys Asp Val Leu Thr Ile Thr Leu Thr
            260                 265                 270 cct aag gtc acg tgt gtt gtg gta gac atc agc aag gat gat ccc gag 864
Pro Lys Val Thr Cys Val Val Val Asp Ile Ser Lys Asp Asp Pro Glu
        275                 280                 285 gtc cag ttc agc tgg ttt gta gat gat gtg gag gtg cac aca gct cag 912
Val Gln Phe Ser Trp Phe Val Asp Asp Val Glu Val His Thr Ala Gln
    290                 295                 300 acg caa ccc cgg gag gag cag ttc aac agc act ttc cgc tca gtc agt 960
Thr Gln Pro Arg Glu Glu Gln Phe Asn Ser Thr Phe Arg Ser Val Ser
305                 310                 315                 320
```

```
gaa ctt ccc atc atg cac cag gac tgg ctc aat ggc aag gag ttc aaa    1008
Glu Leu Pro Ile Met His Gln Asp Trp Leu Asn Gly Lys Glu Phe Lys
                325                 330                 335 tgc agg gtc aac agt gca gct ttc cct gcc ccc atc gag aaa acc atc    1056
Cys Arg Val Asn Ser Ala Ala Phe Pro Ala Pro Ile Glu Lys Thr Ile
            340                 345                 350 tcc aaa acc aaa ggc aga ccg aag gct cca cag gtg tac acc att cca    1104
Ser Lys Thr Lys Gly Arg Pro Lys Ala Pro Gln Val Tyr Thr Ile Pro
        355                 360                 365 cct ccc aag gag cag atg gcc aag gat aaa gtc agt ctg acc tgc atg    1152
Pro Pro Lys Glu Gln Met Ala Lys Asp Lys Val Ser Leu Thr Cys Met
    370                 375                 380 ata aca gac ttc ttc cct gaa gac att act gtg gag tgg cag tgg aat    1200
Ile Thr Asp Phe Phe Pro Glu Asp Ile Thr Val Glu Trp Gln Trp Asn
385                 390                 395                 400 ggg cag cca gcg gag aac tac aag aac act cag ccc atc atg gac aca    1248
Gly Gln Pro Ala Glu Asn Tyr Lys Asn Thr Gln Pro Ile Met Asp Thr
                405                 410                 415 gat ggc tct tac ttc gtc tac agc aag ctc aat gtg cag aag agc aac    1296
Asp Gly Ser Tyr Phe Val Tyr Ser Lys Leu Asn Val Gln Lys Ser Asn
            420                 425                 430 tgg gag gca gga aat act ttc acc tgc tct gtg tta cat gag ggc ctg    1344
Trp Glu Ala Gly Asn Thr Phe Thr Cys Ser Val Leu His Glu Gly Leu
        435                 440                 445 cac aac cac cat act gag aag agc ctc tcc cac tct cct ggg ctg caa    1392
His Asn His His Thr Glu Lys Ser Leu Ser His Ser Pro Gly Leu Gln
    450                 455                 460 agc ttg tcg aga agt act aga gga tca taa                            1422
Ser Leu Ser Arg Ser Thr Arg Gly Ser
465                 470

<210> SEQ ID NO 39
<211> LENGTH: 473
<212> TYPE: PRT
<213> ORGANISM: Artificial
<220> FEATURE:
<223> OTHER INFORMATION: Synthetic Construct

<400> SEQUENCE: 39

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Ser
            20                  25                  30

Thr Asn Pro Lys Pro Gln Arg Lys Thr Lys Arg Asn Thr Asn Arg Arg
        35                  40                  45

Pro Gln Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80

Lys Thr Ser Glu Arg Ser Gln Pro Arg Gly Arg Gln Pro Ile Pro
                85                  90                  95

Lys Ala Arg Arg Pro Glu Gly Arg Thr Trp Ala Gln Pro Gly Tyr Pro
            100                 105                 110

Trp Pro Leu Tyr Gly Asn Glu Gly Cys Gly Trp Ala Gly Trp Leu Leu
        115                 120                 125

Ser Pro Arg Gly Ser Arg Pro Ser Trp Gly Pro Thr Asp Pro Arg Arg
    130                 135                 140

Arg Ser Arg Asn Leu Gly Lys Val Ile Asp Thr Leu Thr Cys Gly Phe
145                 150                 155                 160
```

```
Ala Asp Leu Met Gly Tyr Ile Pro Leu Val Gly Ala Pro Leu Gly Gly
            165                 170                 175

Ala Ala Arg Ala Leu Ala His Gly Val Arg Val Leu Glu Asp Gly Val
        180                 185                 190

Asn Tyr Ala Thr Gly Asn Leu Pro Gly Cys Ser Phe Ser Ile Phe Leu
    195                 200                 205

Leu Ala Leu Leu Ser Cys Leu Thr Val Pro Ala Ser Ala Gly Leu Val
210                 215                 220

Arg Pro Gln Gly Gly Ser Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
                260                 265                 270

Pro Lys Val Thr Cys Val Val Val Asp Ile Ser Lys Asp Asp Pro Glu
            275                 280                 285

Val Gln Phe Ser Trp Phe Val Asp Asp Val Glu Val His Thr Ala Gln
        290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
                340                 345                 350

Ser Lys Thr Lys Gly Arg Pro Lys Ala Pro Gln Val Tyr Thr Ile Pro
            355                 360                 365

Pro Pro Lys Glu Gln Met Ala Lys Asp Lys Val Ser Leu Thr Cys Met
        370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                405                 410                 415

Asp Gly Ser Tyr Phe Val Tyr Ser Lys Leu Asn Val Gln Lys Ser Asn
                420                 425                 430

Trp Glu Ala Gly Asn Thr Phe Thr Cys Ser Val Leu His Glu Gly Leu
            435                 440                 445

His Asn His His Thr Glu Lys Ser Leu Ser His Ser Pro Gly Leu Gln
        450                 455                 460

Ser Leu Ser Arg Ser Thr Arg Gly Ser
465                 470
```

<210> SEQ ID NO 40
<211> LENGTH: 1380
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1380)

<400> SEQUENCE: 40

```
atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc atg agc      96
Thr Glu Asn Leu Tyr Phe Gln Gly Ala Met Asp Pro Glu Phe Met Ser
```

```
               20                  25                  30
acg aat cct aaa cct caa aga aaa acc aaa cgt aac acc aac cgt cgc     144
Thr Asn Pro Lys Pro Gln Arg Lys Thr Lys Arg Asn Thr Asn Arg Arg
         35                  40                  45 cca cag gac gtc aag ttc ccg ggt ggc ggt cag atc gtt ggt gga gtt     192
Pro Gln Asp Val Lys Phe Pro Gly Gly Gly Gln Ile Val Gly Gly Val
 50                  55                  60 tac ttg ttg ccg cgc agg ggc cct aga ttg ggt gtg cgc gcg acg agg     240
Tyr Leu Leu Pro Arg Arg Gly Pro Arg Leu Gly Val Arg Ala Thr Arg
 65                  70                  75                  80 aag act tcc gag cgg tcg caa cct cga ggt aga cgt cag cct atc ccc     288
Lys Thr Ser Glu Arg Ser Gln Pro Arg Gly Arg Arg Gln Pro Ile Pro
             85                  90                  95 aag gca cgt cgg ccc gag ggc agg acc tgg gct cag ccc ggg tac cct     336
Lys Ala Arg Arg Pro Glu Gly Arg Thr Trp Ala Gln Pro Gly Tyr Pro
100                 105                 110 tgg ccc ctc tat ggc aat gag ggt tgc ggg tgg gcg gga tgg ctc ctg     384
Trp Pro Leu Tyr Gly Asn Glu Gly Cys Gly Trp Ala Gly Trp Leu Leu
            115                 120                 125 tct ccc cgt ggc tct cgg cct agc tgg ggc ccc aca gac ccc cgg cgt     432
Ser Pro Arg Gly Ser Arg Pro Ser Trp Gly Pro Thr Asp Pro Arg Arg
130                 135                 140 agg tcg cgc aat ttg ggt aag gtc atc gat acc ctt acg tgc ggc ttc     480
Arg Ser Arg Asn Leu Gly Lys Val Ile Asp Thr Leu Thr Cys Gly Phe
145                 150                 155                 160 gcc gac ctc atg ggg tac ata ccg ctc gtc ggc gcc cct ctt gga ggc     528
Ala Asp Leu Met Gly Tyr Ile Pro Leu Val Gly Ala Pro Leu Gly Gly
                165                 170                 175 gct gcc agg gcc ctg gcg cat ggc gtc cgg gtt ctg gaa gac ggc gtg     576
Ala Ala Arg Ala Leu Ala His Gly Val Arg Val Leu Glu Asp Gly Val
            180                 185                 190 aac tat gca aca ggg aac ctt cct ggt tgc tct ttc tct atc ttc gga     624
Asn Tyr Ala Thr Gly Asn Leu Pro Gly Cys Ser Phe Ser Ile Phe Gly
        195                 200                 205 cta gtg cgg ccg caa ggc ggc gga tcc gtg gac aag aaa att gtg ccc     672
Leu Val Arg Pro Gln Gly Gly Gly Ser Val Asp Lys Lys Ile Val Pro
210                 215                 220 agg gat tgt ggt tgt aag cct tgc ata tgt aca gtc cca gaa gta tca     720
Arg Asp Cys Gly Cys Lys Pro Cys Ile Cys Thr Val Pro Glu Val Ser
225                 230                 235                 240 tct gtc ttc atc ttc ccc cca aag ccc aag gat gtg ctc acc att act     768
Ser Val Phe Ile Phe Pro Pro Lys Pro Lys Asp Val Leu Thr Ile Thr
                245                 250                 255 ctg act cct aag gtc acg tgt gtt gtg gta gac atc agc aag gat gat     816
Leu Thr Pro Lys Val Thr Cys Val Val Val Asp Ile Ser Lys Asp Asp
            260                 265                 270 ccc gag gtc cag ttc agc tgg ttt gta gat gat gtg gag gtg cac aca     864
Pro Glu Val Gln Phe Ser Trp Phe Val Asp Asp Val Glu Val His Thr
        275                 280                 285 gct cag acg caa ccc cgg gag gag cag ttc aac agc act ttc cgc tca     912
Ala Gln Thr Gln Pro Arg Glu Glu Gln Phe Asn Ser Thr Phe Arg Ser
290                 295                 300 gtc agt gaa ctt ccc atc atg cac cag gac tgg ctc aat ggc aag gag     960
Val Ser Glu Leu Pro Ile Met His Gln Asp Trp Leu Asn Gly Lys Glu
305                 310                 315                 320 ttc aaa tgc agg gtc aac agt gca gct ttc cct gcc ccc atc gag aaa    1008
Phe Lys Cys Arg Val Asn Ser Ala Ala Phe Pro Ala Pro Ile Glu Lys
                325                 330                 335 acc atc tcc aaa acc aaa ggc aga ccg aag gct cca cag gtg tac acc    1056
Thr Ile Ser Lys Thr Lys Gly Arg Pro Lys Ala Pro Gln Val Tyr Thr
```

```
att cca cct ccc aag gag cag atg gcc aag gat aaa gtc agt ctg acc      1104
Ile Pro Pro Pro Lys Glu Gln Met Ala Lys Asp Lys Val Ser Leu Thr
        355                 360                 365 tgc atg ata aca gac ttc ttc cct gaa gac att act gtg gag tgg cag      1152
Cys Met Ile Thr Asp Phe Phe Pro Glu Asp Ile Thr Val Glu Trp Gln
370                 375                 380 tgg aat ggg cag cca gcg gag aac tac aag aac act cag ccc atc atg      1200
Trp Asn Gly Gln Pro Ala Glu Asn Tyr Lys Asn Thr Gln Pro Ile Met
385                 390                 395                 400 gac aca gat ggc tct tac ttc gtc tac agc aag ctc aat gtg cag aag      1248
Asp Thr Asp Gly Ser Tyr Phe Val Tyr Ser Lys Leu Asn Val Gln Lys
            405                 410                 415 agc aac tgg gag gca gga aat act ttc acc tgc tct gtg tta cat gag      1296
Ser Asn Trp Glu Ala Gly Asn Thr Phe Thr Cys Ser Val Leu His Glu
        420                 425                 430 ggc ctg cac aac cac cat act gag aag agc ctc tcc cac tct cct ggg      1344
Gly Leu His Asn His His Thr Glu Lys Ser Leu Ser His Ser Pro Gly
    435                 440                 445 ctg caa agc ttg tcg aga agt act aga gga tca taa                      1380
Leu Gln Ser Leu Ser Arg Ser Thr Arg Gly Ser
    450                 455
```

<210> SEQ ID NO 41
<211> LENGTH: 459
<212> TYPE: PRT
<213> ORGANISM: Artificial
<220> FEATURE:
<223> OTHER INFORMATION: Synthetic Construct

<400> SEQUENCE: 41

```
Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Ser
            20                  25                  30

Thr Asn Pro Lys Pro Gln Arg Lys Thr Lys Arg Asn Thr Asn Arg Arg
        35                  40                  45

Pro Gln Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80

Lys Thr Ser Glu Arg Ser Gln Pro Arg Gly Arg Arg Gln Pro Ile Pro
                85                  90                  95

Lys Ala Arg Arg Pro Glu Gly Arg Thr Trp Ala Gln Pro Gly Tyr Pro
            100                 105                 110

Trp Pro Leu Tyr Gly Asn Glu Gly Cys Gly Trp Ala Gly Trp Leu Leu
        115                 120                 125

Ser Pro Arg Gly Ser Arg Pro Ser Trp Gly Pro Thr Asp Pro Arg Arg
    130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Leu Gly Gly
                165                 170                 175

Ala Ala Arg Ala Leu Ala His Gly Val Arg Val Leu Glu Asp Gly Val
            180                 185                 190

Asn Tyr Ala Thr Gly Asn Leu Pro Gly Cys Ser Phe Ser Ile Phe Gly
        195                 200                 205

Leu Val Arg Pro Gln Gly Gly Gly Ser Val Asp Lys Lys Ile Val Pro
```

-continued

```
                    210                 215                 220
Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                    245                 250                 255

Leu Thr Pro Lys Val Thr Cys Val Val Val Asp Ile Ser Lys Asp Asp
                    260                 265                 270

Pro Glu Val Gln Phe Ser Trp Phe Val Asp Asp Val Glu Val His Thr
                    275                 280                 285

Ala Gln Thr Gln Pro Arg Glu Glu Gln Phe Asn Ser Thr Phe Arg Ser
                    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                    325                 330                 335

Thr Ile Ser Lys Thr Lys Gly Arg Pro Lys Ala Pro Gln Val Tyr Thr
                    340                 345                 350

Ile Pro Pro Lys Glu Gln Met Ala Lys Asp Lys Val Ser Leu Thr
                    355                 360                 365

Cys Met Ile Thr Asp Phe Phe Pro Glu Asp Ile Thr Val Glu Trp Gln
370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Val Tyr Ser Lys Leu Asn Val Gln Lys
                    405                 410                 415

Ser Asn Trp Glu Ala Gly Asn Thr Phe Thr Cys Ser Val Leu His Glu
                    420                 425                 430

Gly Leu His Asn His His Thr Glu Lys Ser Leu Ser His Ser Pro Gly
                    435                 440                 445

Leu Gln Ser Leu Ser Arg Ser Thr Arg Gly Ser
                    450                 455
```

<210> SEQ ID NO 42
<211> LENGTH: 2190
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(2190)

<400> SEQUENCE: 42

```
atg tcg tac tac cat cac cat cac cat cac gat tac gat atc cca acg      48
Met Ser Tyr Tyr His His His His His His Asp Tyr Asp Ile Pro Thr
1               5                  10                  15 acc gaa aac ctg tat ttt cag ggc gcc atg gat ccg gaa ttc tcc ggt      96
Thr Glu Asn Leu Tyr Phe Gln Gly Ala Met Asp Pro Glu Phe Ser Gly
                20                  25                  30 tcc tgg cta agg gac atc tgg gac tgg ata tgc gag gtg ctg agc gac     144
Ser Trp Leu Arg Asp Ile Trp Asp Trp Ile Cys Glu Val Leu Ser Asp
            35                  40                  45 ttt aag acc tgg ctg aaa gcc aag ctc atg cca caa ctg cct ggg att     192
Phe Lys Thr Trp Leu Lys Ala Lys Leu Met Pro Gln Leu Pro Gly Ile
        50                  55                  60 ccc ttt gtg tcc tgc cag cgc ggg tat agg ggg gtc tgg cga gga gac     240
Pro Phe Val Ser Cys Gln Arg Gly Tyr Arg Gly Val Trp Arg Gly Asp
65                  70                  75                  80
```

```
                                                    -continued ggc att atg cac act cgc tgc cac tgt gga gct gag atc act gga cat      288
Gly Ile Met His Thr Arg Cys His Cys Gly Ala Glu Ile Thr Gly His
             85                  90                  95 gtc aaa aac ggg acg atg agg atc gtc ggt cct agg acc tgc agg aac      336
Val Lys Asn Gly Thr Met Arg Ile Val Gly Pro Arg Thr Cys Arg Asn
        100                 105                 110 atg tgg agt ggg acg ttc ccc att aac gcc tac acc acg ggc ccc tgt      384
Met Trp Ser Gly Thr Phe Pro Ile Asn Ala Tyr Thr Thr Gly Pro Cys
            115                 120                 125 act ccc ctt cct gcg ccg aac tat aag ttc gcg ctg tgg agg gtg tct      432
Thr Pro Leu Pro Ala Pro Asn Tyr Lys Phe Ala Leu Trp Arg Val Ser
    130                 135                 140 gca gag gaa tac gtg gag ata agg cgg gtg ggg gac ttc cac tac gta      480
Ala Glu Glu Tyr Val Glu Ile Arg Arg Val Gly Asp Phe His Tyr Val
145                 150                 155                 160 tcg ggt atg act act gac aat ctt aaa tgc ccg tgc cag atc cca tcg      528
Ser Gly Met Thr Thr Asp Asn Leu Lys Cys Pro Cys Gln Ile Pro Ser
                165                 170                 175 ccc gaa ttt ttc aca gaa ttg gac ggg gtg cgc cta cac agg ttt gcg      576
Pro Glu Phe Phe Thr Glu Leu Asp Gly Val Arg Leu His Arg Phe Ala
            180                 185                 190 ccc cct tgc aag ccc ttg ctg cgg gag gag gta tca ttc aga gta gga      624
Pro Pro Cys Lys Pro Leu Leu Arg Glu Glu Val Ser Phe Arg Val Gly
        195                 200                 205 ctc cac gag tac ccg gtg ggg tcg caa tta cct tgc gag ccc gaa ccg      672
Leu His Glu Tyr Pro Val Gly Ser Gln Leu Pro Cys Glu Pro Glu Pro
    210                 215                 220 gac gta gcc gtg ttg acg tcc atg ctc act gat ccc tcc cat ata aca      720
Asp Val Ala Val Leu Thr Ser Met Leu Thr Asp Pro Ser His Ile Thr
225                 230                 235                 240 gca gag gcg gcc ggg aga agg ttg gcg aga ggg tca ccc cct tct atg      768
Ala Glu Ala Ala Gly Arg Arg Leu Ala Arg Gly Ser Pro Pro Ser Met
                245                 250                 255 gcc agc tcc tcg gct agc cag ctg tcc gct cca tct ctc aag gca act      816
Ala Ser Ser Ser Ala Ser Gln Leu Ser Ala Pro Ser Leu Lys Ala Thr
            260                 265                 270 tgc acc gcc aac cat gac tcc cct gac gcc gag ctc ata gag gct aac      864
Cys Thr Ala Asn His Asp Ser Pro Asp Ala Glu Leu Ile Glu Ala Asn
        275                 280                 285 ctc ctg tgg agg cag gag atg ggc ggc aac atc acc agg gtt gag tca      912
Leu Leu Trp Arg Gln Glu Met Gly Gly Asn Ile Thr Arg Val Glu Ser
    290                 295                 300 gag aac aaa gtg gtg att ctg gac tcc ttc gat ccg ctt gtg gca gag      960
Glu Asn Lys Val Val Ile Leu Asp Ser Phe Asp Pro Leu Val Ala Glu
305                 310                 315                 320 gag gat gag cgg gag gtc tcc gta cct gca gaa att ctg cgg aag tct     1008
Glu Asp Glu Arg Glu Val Ser Val Pro Ala Glu Ile Leu Arg Lys Ser
                325                 330                 335 cgg aga ttc gcc cgg gcc ctg ccc gtc tgg gcg cgg ccg gac tac aac     1056
Arg Arg Phe Ala Arg Ala Leu Pro Val Trp Ala Arg Pro Asp Tyr Asn
            340                 345                 350 ccc ccg cta gta gag acg tgg aaa aag cct gac tac gaa cca cct gtg     1104
Pro Pro Leu Val Glu Thr Trp Lys Lys Pro Asp Tyr Glu Pro Pro Val
        355                 360                 365 gtc cat ggc tgc ccg cta cca cct cca cgg tcc cct cct gtg cct ccg     1152
Val His Gly Cys Pro Leu Pro Pro Pro Arg Ser Pro Pro Val Pro Pro
    370                 375                 380 cct cgg aaa aag cgt acg gtg gtc ctc acc gaa tca acc cta tct act     1200
Pro Arg Lys Lys Arg Thr Val Val Leu Thr Glu Ser Thr Leu Ser Thr
385                 390                 395                 400
```

```
gcc ttg gcc gag ctt gcc acc aaa agt ttt ggc agc tcc tca act tcc    1248
Ala Leu Ala Glu Leu Ala Thr Lys Ser Phe Gly Ser Ser Ser Thr Ser
            405                 410                 415 ggc att acg ggc gac aat acg aca aca tcc tct gag ccc gcc cct tct    1296
Gly Ile Thr Gly Asp Asn Thr Thr Thr Ser Ser Glu Pro Ala Pro Ser
        420                 425                 430 ggc tgc ccc ccc gac tcc gac gtt gag tcc tat tct tcc atg ccc ccc    1344
Gly Cys Pro Pro Asp Ser Asp Val Glu Ser Tyr Ser Ser Met Pro Pro
        435                 440                 445 ctg gag ggg gag cct ggg gat ccg gat ctc agc gac ggg tca tgg tcg    1392
Leu Glu Gly Glu Pro Gly Asp Pro Asp Leu Ser Asp Gly Ser Trp Ser
    450                 455                 460 acg gtc agt agt ggg gcc gac acg gaa gat gtc gtg tgc gga cta gtg    1440
Thr Val Ser Ser Gly Ala Asp Thr Glu Asp Val Val Cys Gly Leu Val
465                 470                 475                 480 cgg ccg caa ggc ggc gga tcc gtg gac aag aaa att gtg ccc agg gat    1488
Arg Pro Gln Gly Gly Gly Ser Val Asp Lys Lys Ile Val Pro Arg Asp
                485                 490                 495 tgt ggt tgt aag cct tgc ata tgt aca gtc cca gaa gta tca tct gtc    1536
Cys Gly Cys Lys Pro Cys Ile Cys Thr Val Pro Glu Val Ser Ser Val
            500                 505                 510 ttc atc ttc ccc cca aag ccc aag gat gtg ctc acc att act ctg act    1584
Phe Ile Phe Pro Pro Lys Pro Lys Asp Val Leu Thr Ile Thr Leu Thr
        515                 520                 525 cct aag gtc acg tgt gtt gtg gta gac atc agc aag gat gat ccc gag    1632
Pro Lys Val Thr Cys Val Val Val Asp Ile Ser Lys Asp Asp Pro Glu
        530                 535                 540 gtc cag ttc agc tgg ttt gta gat gat gtg gag gtg cac aca gct cag    1680
Val Gln Phe Ser Trp Phe Val Asp Asp Val Glu Val His Thr Ala Gln
545                 550                 555                 560 acg caa ccc cgg gag gag cag ttc aac agc act ttc cgc tca gtc agt    1728
Thr Gln Pro Arg Glu Glu Gln Phe Asn Ser Thr Phe Arg Ser Val Ser
                565                 570                 575 gaa ctt ccc atc atg cac cag gac tgg ctc aat ggc aag gag ttc aaa    1776
Glu Leu Pro Ile Met His Gln Asp Trp Leu Asn Gly Lys Glu Phe Lys
            580                 585                 590 tgc agg gtc aac agt gca gct ttc cct gcc ccc atc gag aaa acc atc    1824
Cys Arg Val Asn Ser Ala Ala Phe Pro Ala Pro Ile Glu Lys Thr Ile
        595                 600                 605 tcc aaa acc aaa ggc aga ccg aag gct cca cag gtg tac acc att cca    1872
Ser Lys Thr Lys Gly Arg Pro Lys Ala Pro Gln Val Tyr Thr Ile Pro
        610                 615                 620 cct ccc aag gag cag atg gcc aag gat aaa gtc agt ctg acc tgc atg    1920
Pro Pro Lys Glu Gln Met Ala Lys Asp Lys Val Ser Leu Thr Cys Met
625                 630                 635                 640 ata aca gac ttc ttc cct gaa gac att act gtg gag tgg cag tgg aat    1968
Ile Thr Asp Phe Phe Pro Glu Asp Ile Thr Val Glu Trp Gln Trp Asn
                645                 650                 655 ggg cag cca gcg gag aac tac aag aac act cag ccc atc atg gac aca    2016
Gly Gln Pro Ala Glu Asn Tyr Lys Asn Thr Gln Pro Ile Met Asp Thr
            660                 665                 670 gat ggc tct tac ttc gtc tac agc aag ctc aat gtg cag aag agc aac    2064
Asp Gly Ser Tyr Phe Val Tyr Ser Lys Leu Asn Val Gln Lys Ser Asn
        675                 680                 685 tgg gag gca gga aat act ttc acc tgc tct gtg tta cat gag ggc ctg    2112
Trp Glu Ala Gly Asn Thr Phe Thr Cys Ser Val Leu His Glu Gly Leu
        690                 695                 700 cac aac cac cat act gag aag agc ctc tcc cac tct cct ggg ctg caa    2160
His Asn His His Thr Glu Lys Ser Leu Ser His Ser Pro Gly Leu Gln
705                 710                 715                 720
```

```
agc ttg tcg aga agt act aga gga tca taa                                    2190
Ser Leu Ser Arg Ser Thr Arg Gly Ser
            725
```

<210> SEQ ID NO 43
<211> LENGTH: 729
<212> TYPE: PRT
<213> ORGANISM: Artificial
<220> FEATURE:
<223> OTHER INFORMATION: Synthetic Construct

<400> SEQUENCE: 43

```
Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Ser Gly
            20                  25                  30

Ser Trp Leu Arg Asp Ile Trp Asp Trp Ile Cys Glu Val Leu Ser Asp
        35                  40                  45

Phe Lys Thr Trp Leu Lys Ala Lys Leu Met Pro Gln Leu Pro Gly Ile
    50                  55                  60

Pro Phe Val Ser Cys Gln Arg Gly Tyr Arg Gly Val Trp Arg Gly Asp
65                  70                  75                  80

Gly Ile Met His Thr Arg Cys His Cys Gly Ala Glu Ile Thr Gly His
                85                  90                  95

Val Lys Asn Gly Thr Met Arg Ile Val Gly Pro Arg Thr Cys Arg Asn
            100                 105                 110

Met Trp Ser Gly Thr Phe Pro Ile Asn Ala Tyr Thr Thr Gly Pro Cys
        115                 120                 125

Thr Pro Leu Pro Ala Pro Asn Tyr Lys Phe Ala Leu Trp Arg Val Ser
    130                 135                 140

Ala Glu Glu Tyr Val Glu Ile Arg Arg Val Gly Asp Phe His Tyr Val
145                 150                 155                 160

Ser Gly Met Thr Thr Asp Asn Leu Lys Cys Pro Cys Gln Ile Pro Ser
                165                 170                 175

Pro Glu Phe Phe Thr Glu Leu Asp Gly Val Arg Leu His Arg Phe Ala
            180                 185                 190

Pro Pro Cys Lys Pro Leu Leu Arg Glu Glu Val Ser Phe Arg Val Gly
        195                 200                 205

Leu His Glu Tyr Pro Val Gly Ser Gln Leu Pro Cys Glu Pro Glu Pro
    210                 215                 220

Asp Val Ala Val Leu Thr Ser Met Leu Thr Asp Pro Ser His Ile Thr
225                 230                 235                 240

Ala Glu Ala Ala Gly Arg Arg Leu Ala Arg Gly Ser Pro Pro Ser Met
                245                 250                 255

Ala Ser Ser Ser Ala Ser Gln Leu Ser Ala Pro Ser Leu Lys Ala Thr
            260                 265                 270

Cys Thr Ala Asn His Asp Ser Pro Asp Ala Glu Leu Ile Glu Ala Asn
        275                 280                 285

Leu Leu Trp Arg Gln Glu Met Gly Gly Asn Ile Thr Arg Val Glu Ser
    290                 295                 300

Glu Asn Lys Val Val Ile Leu Asp Ser Phe Asp Pro Leu Val Ala Glu
305                 310                 315                 320

Glu Asp Glu Arg Glu Val Ser Val Pro Ala Glu Ile Leu Arg Lys Ser
                325                 330                 335

Arg Arg Phe Ala Arg Ala Leu Pro Val Trp Ala Arg Pro Asp Tyr Asn
            340                 345                 350
```

```
Pro Pro Leu Val Glu Thr Trp Lys Lys Pro Asp Tyr Glu Pro Pro Val
            355                 360                 365

Val His Gly Cys Pro Leu Pro Pro Arg Ser Pro Val Pro Pro
370                 375                 380

Pro Arg Lys Lys Arg Thr Val Val Leu Thr Glu Ser Thr Leu Ser Thr
385                 390                 395                 400

Ala Leu Ala Glu Leu Ala Thr Lys Ser Phe Gly Ser Ser Thr Ser
            405                 410                 415

Gly Ile Thr Gly Asp Asn Thr Thr Ser Ser Glu Pro Ala Pro Ser
            420                 425                 430

Gly Cys Pro Pro Asp Ser Asp Val Glu Ser Tyr Ser Ser Met Pro Pro
            435                 440                 445

Leu Glu Gly Glu Pro Gly Asp Pro Asp Leu Ser Asp Gly Ser Trp Ser
450                 455                 460

Thr Val Ser Ser Gly Ala Asp Thr Glu Asp Val Val Cys Gly Leu Val
465                 470                 475                 480

Arg Pro Gln Gly Gly Ser Val Asp Lys Ile Val Pro Arg Asp
            485                 490                 495

Cys Gly Cys Lys Pro Cys Ile Cys Thr Val Pro Glu Val Ser Ser Val
            500                 505                 510

Phe Ile Phe Pro Pro Lys Pro Lys Asp Val Leu Thr Ile Thr Leu Thr
            515                 520                 525

Pro Lys Val Thr Cys Val Val Asp Ile Ser Lys Asp Asp Pro Glu
530                 535                 540

Val Gln Phe Ser Trp Phe Val Asp Asp Val Glu Val His Thr Ala Gln
545                 550                 555                 560

Thr Gln Pro Arg Glu Glu Gln Phe Asn Ser Thr Phe Arg Ser Val Ser
                565                 570                 575

Glu Leu Pro Ile Met His Gln Asp Trp Leu Asn Gly Lys Glu Phe Lys
            580                 585                 590

Cys Arg Val Asn Ser Ala Ala Phe Pro Ala Pro Ile Glu Lys Thr Ile
            595                 600                 605

Ser Lys Thr Lys Gly Arg Pro Lys Ala Pro Gln Val Tyr Thr Ile Pro
610                 615                 620

Pro Pro Lys Glu Gln Met Ala Lys Asp Lys Val Ser Leu Thr Cys Met
625                 630                 635                 640

Ile Thr Asp Phe Phe Pro Glu Asp Ile Thr Val Glu Trp Gln Trp Asn
                645                 650                 655

Gly Gln Pro Ala Glu Asn Tyr Lys Asn Thr Gln Pro Ile Met Asp Thr
            660                 665                 670

Asp Gly Ser Tyr Phe Val Tyr Ser Lys Leu Asn Val Gln Lys Ser Asn
            675                 680                 685

Trp Glu Ala Gly Asn Thr Phe Thr Cys Ser Val Leu His Glu Gly Leu
690                 695                 700

His Asn His His Thr Glu Lys Ser Leu Ser His Ser Pro Gly Leu Gln
705                 710                 715                 720

Ser Leu Ser Arg Ser Thr Arg Gly Ser
                725

<210> SEQ ID NO 44
<211> LENGTH: 1428
<212> TYPE: DNA
<213> ORGANISM: Artificial
<220> FEATURE:
<223> OTHER INFORMATION: Hepatitis C virus plus murine
<220> FEATURE:
```

<221> NAME/KEY: CDS
<222> LOCATION: (1)..(1428)

<400> SEQUENCE: 44

```
atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc tac caa      96
Thr Glu Asn Leu Tyr Phe Gln Gly Ala Met Asp Pro Glu Phe Tyr Gln
            20                  25                  30 gtg cgc aat tcc tcg ggg ctt tac cat gtc acc aat gat tgc cct aac     144
Val Arg Asn Ser Ser Gly Leu Tyr His Val Thr Asn Asp Cys Pro Asn
        35                  40                  45 tcg agt att gtg tac gag gcg gcc gat gcc atc ctg cac act ccg ggg     192
Ser Ser Ile Val Tyr Glu Ala Ala Asp Ala Ile Leu His Thr Pro Gly
    50                  55                  60 tgt gtc cct tgc gtt cgc gag ggt aac gcc tcg agg tgt tgg gtg gcg     240
Cys Val Pro Cys Val Arg Glu Gly Asn Ala Ser Arg Cys Trp Val Ala
65                  70                  75                  80 gtg acc ccc acg gtg gcc acc agg gac ggc aaa ctc ccc aca acg cag     288
Val Thr Pro Thr Val Ala Thr Arg Asp Gly Lys Leu Pro Thr Thr Gln
                85                  90                  95 ctt cga cgt cat atc gat ctg ctt gtc ggg agc gcc acc ctc tgc tcg     336
Leu Arg Arg His Ile Asp Leu Leu Val Gly Ser Ala Thr Leu Cys Ser
            100                 105                 110 gcc ctc tac gtg ggg gac ctg tgc ggg tct gtc ttt ctt gtt ggt caa     384
Ala Leu Tyr Val Gly Asp Leu Cys Gly Ser Val Phe Leu Val Gly Gln
        115                 120                 125 ctg ttt acc ttc tct ccc agg cgc cac tgg acg acg caa gac tgc aat     432
Leu Phe Thr Phe Ser Pro Arg Arg His Trp Thr Thr Gln Asp Cys Asn
    130                 135                 140 tgt tct atc tat ccc ggc cat ata acg ggt cat cgc atg gca tgg gat     480
Cys Ser Ile Tyr Pro Gly His Ile Thr Gly His Arg Met Ala Trp Asp
145                 150                 155                 160 atg atg atg aac tgg tcc cct acg gca gcg ttg gtg gta gct cag ctg     528
Met Met Met Asn Trp Ser Pro Thr Ala Ala Leu Val Val Ala Gln Leu
                165                 170                 175 ctc cgg atc cca caa gcc atc atg gac atg atc gct ggt gct cac tgg     576
Leu Arg Ile Pro Gln Ala Ile Met Asp Met Ile Ala Gly Ala His Trp
            180                 185                 190 gga gtc ctg gcg ggc ata gcg tat ttc tcc atg gtg ggg aac tgg gcg     624
Gly Val Leu Ala Gly Ile Ala Tyr Phe Ser Met Val Gly Asn Trp Ala
        195                 200                 205 aag gtc ctg gta gtg ctg ctg cta ttt gcc ggc gtc gac gcg gaa gga     672
Lys Val Leu Val Val Leu Leu Leu Phe Ala Gly Val Asp Ala Glu Gly
    210                 215                 220 cta gtg cgg ccg caa ggc ggc gga tcc gtg gac aag aaa att gtg ccc     720
Leu Val Arg Pro Gln Gly Gly Gly Ser Val Asp Lys Lys Ile Val Pro
225                 230                 235                 240 agg gat tgt ggt tgt aag cct tgc ata tgt aca gtc cca gaa gta tca     768
Arg Asp Cys Gly Cys Lys Pro Cys Ile Cys Thr Val Pro Glu Val Ser
                245                 250                 255 tct gtc ttc atc ttc ccc cca aag ccc aag gat gtg ctc acc att act     816
Ser Val Phe Ile Phe Pro Pro Lys Pro Lys Asp Val Leu Thr Ile Thr
            260                 265                 270 ctg act cct aag gtc acg tgt gtt gtg gta gac atc agc aag gat gat     864
Leu Thr Pro Lys Val Thr Cys Val Val Val Asp Ile Ser Lys Asp Asp
        275                 280                 285 ccc gag gtc cag ttc agc tgg ttt gta gat gat gtg gag gtg cac aca     912
Pro Glu Val Gln Phe Ser Trp Phe Val Asp Asp Val Glu Val His Thr
    290                 295                 300
```

-continued

```
gct cag acg caa ccc cgg gag gag cag ttc aac agc act ttc cgc tca      960
Ala Gln Thr Gln Pro Arg Glu Glu Gln Phe Asn Ser Thr Phe Arg Ser
305                 310                 315                 320 gtc agt gaa ctt ccc atc atg cac cag gac tgg ctc aat ggc aag gag     1008
Val Ser Glu Leu Pro Ile Met His Gln Asp Trp Leu Asn Gly Lys Glu
                325                 330                 335 ttc aaa tgc agg gtc aac agt gca gct ttc cct gcc ccc atc gag aaa     1056
Phe Lys Cys Arg Val Asn Ser Ala Ala Phe Pro Ala Pro Ile Glu Lys
            340                 345                 350 acc atc tcc aaa acc aaa ggc aga ccg aag gct cca cag gtg tac acc     1104
Thr Ile Ser Lys Thr Lys Gly Arg Pro Lys Ala Pro Gln Val Tyr Thr
        355                 360                 365 att cca cct ccc aag gag cag atg gcc aag gat aaa gtc agt ctg acc     1152
Ile Pro Pro Pro Lys Glu Gln Met Ala Lys Asp Lys Val Ser Leu Thr
370                 375                 380 tgc atg ata aca gac ttc ttc cct gaa gac att act gtg gag tgg cag     1200
Cys Met Ile Thr Asp Phe Phe Pro Glu Asp Ile Thr Val Glu Trp Gln
385                 390                 395                 400 tgg aat ggg cag cca gcg gag aac tac aag aac act cag ccc atc atg     1248
Trp Asn Gly Gln Pro Ala Glu Asn Tyr Lys Asn Thr Gln Pro Ile Met
                405                 410                 415 gac aca gat ggc tct tac ttc gtc tac agc aag ctc aat gtg cag aag     1296
Asp Thr Asp Gly Ser Tyr Phe Val Tyr Ser Lys Leu Asn Val Gln Lys
            420                 425                 430 agc aac tgg gag gca gga aat act ttc acc tgc tct gtg tta cat gag     1344
Ser Asn Trp Glu Ala Gly Asn Thr Phe Thr Cys Ser Val Leu His Glu
        435                 440                 445 ggc ctg cac aac cac cat act gag aag agc ctc tcc cac tct cct ggg     1392
Gly Leu His Asn His His Thr Glu Lys Ser Leu Ser His Ser Pro Gly
    450                 455                 460 ctg caa agc ttg tcg aga agt act aga gga tca taa                     1428
Leu Gln Ser Leu Ser Arg Ser Thr Arg Gly Ser
465                 470                 475
```

<210> SEQ ID NO 45
<211> LENGTH: 475
<212> TYPE: PRT
<213> ORGANISM: Artificial
<220> FEATURE:
<223> OTHER INFORMATION: Synthetic Construct

<400> SEQUENCE: 45

```
Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Tyr Gln
                20                  25                  30

Val Arg Asn Ser Ser Gly Leu Tyr His Val Thr Asn Asp Cys Pro Asn
            35                  40                  45

Ser Ser Ile Val Tyr Glu Ala Ala Asp Ala Ile Leu His Thr Pro Gly
        50                  55                  60

Cys Val Pro Cys Val Arg Glu Gly Asn Ala Ser Arg Cys Trp Val Ala
65                  70                  75                  80

Val Thr Pro Thr Val Ala Thr Arg Asp Gly Lys Leu Pro Thr Thr Gln
                85                  90                  95

Leu Arg Arg His Ile Asp Leu Leu Val Gly Ser Ala Thr Leu Cys Ser
            100                 105                 110

Ala Leu Tyr Val Gly Asp Leu Cys Gly Ser Val Phe Leu Val Gly Gln
        115                 120                 125

Leu Phe Thr Phe Ser Pro Arg Arg His Trp Thr Thr Gln Asp Cys Asn
```

|     |     |     |     | 130 |     |     |     |     | 135 |     |     |     |     | 140 |     |
| --- | --- | --- | --- | --- | --- | --- | --- | --- | --- | --- | --- | --- | --- | --- | --- |

Cys Ser Ile Tyr Pro Gly His Ile Thr Gly His Arg Met Ala Trp Asp
145                 150                 155                 160

Met Met Met Asn Trp Ser Pro Thr Ala Ala Leu Val Val Ala Gln Leu
                165                 170                 175

Leu Arg Ile Pro Gln Ala Ile Met Asp Met Ile Ala Gly Ala His Trp
                180                 185                 190

Gly Val Leu Ala Gly Ile Ala Tyr Phe Ser Met Val Gly Asn Trp Ala
                195                 200                 205

Lys Val Leu Val Val Leu Leu Leu Phe Ala Gly Val Asp Ala Glu Gly
210                 215                 220

Leu Val Arg Pro Gln Gly Gly Ser Val Asp Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
                260                 265                 270

Leu Thr Pro Lys Val Thr Cys Val Val Asp Ile Ser Lys Asp Asp
275                 280                 285

Pro Glu Val Gln Phe Ser Trp Phe Val Asp Asp Val Glu Val His Thr
290                 295                 300

Ala Gln Thr Gln Pro Arg Glu Glu Gln Phe Asn Ser Thr Phe Arg Ser
305                 310                 315                 320

Val Ser Glu Leu Pro Ile Met His Gln Asp Trp Leu Asn Gly Lys Glu
                325                 330                 335

Phe Lys Cys Arg Val Asn Ser Ala Ala Phe Pro Ala Pro Ile Glu Lys
                340                 345                 350

Thr Ile Ser Lys Thr Lys Gly Arg Pro Lys Ala Pro Gln Val Tyr Thr
                355                 360                 365

Ile Pro Pro Pro Lys Glu Gln Met Ala Lys Asp Lys Val Ser Leu Thr
                370                 375                 380

Cys Met Ile Thr Asp Phe Phe Pro Glu Asp Ile Thr Val Glu Trp Gln
385                 390                 395                 400

Trp Asn Gly Gln Pro Ala Glu Asn Tyr Lys Asn Thr Gln Pro Ile Met
                405                 410                 415

Asp Thr Asp Gly Ser Tyr Phe Val Tyr Ser Lys Leu Asn Val Gln Lys
                420                 425                 430

Ser Asn Trp Glu Ala Gly Asn Thr Phe Thr Cys Ser Val Leu His Glu
                435                 440                 445

Gly Leu His Asn His His Thr Glu Lys Ser Leu Ser His Ser Pro Gly
                450                 455                 460

Leu Gln Ser Leu Ser Arg Ser Thr Arg Gly Ser
465                 470                 475

<210> SEQ ID NO 46
<211> LENGTH: 1938
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1938)

<400> SEQUENCE: 46 atg tcg tac tac cat cac cat cac cat cac gat tac gat atc cca acg    48
Met Ser Tyr Tyr His His His His His His Asp Tyr Asp Ile Pro Thr

```
1               5                  10                  15 acc gaa aac ctg tat ttt cag ggc gcc atg gat ccg gaa ttc acc cac        96
Thr Glu Asn Leu Tyr Phe Gln Gly Ala Met Asp Pro Glu Phe Thr His
            20                  25                  30 gtc acc ggg gga aat gcc ggc cgc acc acg gct ggg ctt gtt ggt ctc       144
Val Thr Gly Gly Asn Ala Gly Arg Thr Thr Ala Gly Leu Val Gly Leu
        35                  40                  45 ctt aca cca ggc gcc aag cag aac atc caa ctg atc aac acc aac ggc       192
Leu Thr Pro Gly Ala Lys Gln Asn Ile Gln Leu Ile Asn Thr Asn Gly
    50                  55                  60 agt tgg cac atc aat agc acg gcc ttg aat tgc aat gaa agc ctt aac       240
Ser Trp His Ile Asn Ser Thr Ala Leu Asn Cys Asn Glu Ser Leu Asn
65                  70                  75                  80 acc ggc tgg tta gca ggg ctc ttc tat caa cac aaa ttc aac tct tca       288
Thr Gly Trp Leu Ala Gly Leu Phe Tyr Gln His Lys Phe Asn Ser Ser
                85                  90                  95 ggc tgt cct gag agg ttg gcc agc tgc cga cgc ctt acc gat ttt gcc       336
Gly Cys Pro Glu Arg Leu Ala Ser Cys Arg Arg Leu Thr Asp Phe Ala
            100                 105                 110 cag ggc tgg ggt cct atc agt tat gcc aac gga agc ggc ctc gac gaa       384
Gln Gly Trp Gly Pro Ile Ser Tyr Ala Asn Gly Ser Gly Leu Asp Glu
        115                 120                 125 cgc ccc tac tgc tgg cac tac cct cca aga cct tgt ggc att gtg ccc       432
Arg Pro Tyr Cys Trp His Tyr Pro Pro Arg Pro Cys Gly Ile Val Pro
    130                 135                 140 gca aag agc gtg tgt ggc ccg gta tat tgc ttc act ccc agc ccc gtg       480
Ala Lys Ser Val Cys Gly Pro Val Tyr Cys Phe Thr Pro Ser Pro Val
145                 150                 155                 160 gtg gtg gga acg acc gac agg tcg ggc gcg cct acc tac agc tgg ggt       528
Val Val Gly Thr Thr Asp Arg Ser Gly Ala Pro Thr Tyr Ser Trp Gly
                165                 170                 175 gca aat gat acg gat gtc ttc gtc ctt aac aac acc agg cca ccg ctg       576
Ala Asn Asp Thr Asp Val Phe Val Leu Asn Asn Thr Arg Pro Pro Leu
            180                 185                 190 ggc aat tgg ttc ggt tgt acc tgg atg aac tca act gga ttc acc aaa       624
Gly Asn Trp Phe Gly Cys Thr Trp Met Asn Ser Thr Gly Phe Thr Lys
        195                 200                 205 gtg tgc gga gcg ccc cct tgt gtc atc gga ggg gtg ggc aac aac acc       672
Val Cys Gly Ala Pro Pro Cys Val Ile Gly Gly Val Gly Asn Asn Thr
    210                 215                 220 ttg ctc tgc ccc act gat tgc ttc cgc aaa cat ccg gaa gcc aca tac       720
Leu Leu Cys Pro Thr Asp Cys Phe Arg Lys His Pro Glu Ala Thr Tyr
225                 230                 235                 240 tct cgg tgc ggc tcc ggt ccc tgg att aca ccc agg tgc atg gtc gac       768
Ser Arg Cys Gly Ser Gly Pro Trp Ile Thr Pro Arg Cys Met Val Asp
                245                 250                 255 tac ccg tat agg ctt tgg cac tat cct tgt acc atc aat tac acc ata       816
Tyr Pro Tyr Arg Leu Trp His Tyr Pro Cys Thr Ile Asn Tyr Thr Ile
            260                 265                 270 ttc aaa gtc agg atg tac gtg gga ggg gtc gag cac agg ctg gaa gcg       864
Phe Lys Val Arg Met Tyr Val Gly Gly Val Glu His Arg Leu Glu Ala
        275                 280                 285 gcc tgc aac tgg acg cgg ggc gaa cgc tgt gat ctg gaa gac agg gac       912
Ala Cys Asn Trp Thr Arg Gly Glu Arg Cys Asp Leu Glu Asp Arg Asp
    290                 295                 300 agg tcc gag ctc agc ccg ttg ctg ctg tcc acc aca cag tgg cag gtc       960
Arg Ser Glu Leu Ser Pro Leu Leu Leu Ser Thr Thr Gln Trp Gln Val
305                 310                 315                 320 ctt ccg tgt tct ttc acg acc ctg cca gcc ttg tcc acc ggc ctc atc      1008
Leu Pro Cys Ser Phe Thr Thr Leu Pro Ala Leu Ser Thr Gly Leu Ile
```

```
                    325                 330                 335
cac ctc cac cag aac att gtg gac gtg cag tac ttg tac ggg gta ggg         1056
His Leu His Gln Asn Ile Val Asp Val Gln Tyr Leu Tyr Gly Val Gly
            340                 345                 350 tca agc atc gcg tcc tgg gcc att aag tgg gag tac gtc gtt ctc ctg         1104
Ser Ser Ile Ala Ser Trp Ala Ile Lys Trp Glu Tyr Val Val Leu Leu
            355                 360                 365 ttc ctt ctg ctt gca gac gcg cgc gtc tgc tcc tgc ttg tgg atg atg         1152
Phe Leu Leu Leu Ala Asp Ala Arg Val Cys Ser Cys Leu Trp Met Met
        370                 375                 380 tta ctc ata tcc caa gcg gag gcg gct gga cta gtg cgg ccg caa ggc         1200
Leu Leu Ile Ser Gln Ala Glu Ala Ala Gly Leu Val Arg Pro Gln Gly
385                 390                 395                 400 ggc gga tcc gtg gac aag aaa att gtg ccc agg gat tgt ggt tgt aag         1248
Gly Gly Ser Val Asp Lys Lys Ile Val Pro Arg Asp Cys Gly Cys Lys
            405                 410                 415 cct tgc ata tgt aca gtc cca gaa gta tca tct gtc ttc atc ttc ccc         1296
Pro Cys Ile Cys Thr Val Pro Glu Val Ser Ser Val Phe Ile Phe Pro
            420                 425                 430 cca aag ccc aag gat gtg ctc acc att act ctg act cct aag gtc acg         1344
Pro Lys Pro Lys Asp Val Leu Thr Ile Thr Leu Thr Pro Lys Val Thr
        435                 440                 445 tgt gtt gtg gta gac atc agc aag gat gat ccc gag gtc cag ttc agc         1392
Cys Val Val Val Asp Ile Ser Lys Asp Asp Pro Glu Val Gln Phe Ser
450                 455                 460 tgg ttt gta gat gat gtg gag gtg cac aca gct cag acg caa ccc cgg         1440
Trp Phe Val Asp Asp Val Glu Val His Thr Ala Gln Thr Gln Pro Arg
465                 470                 475                 480 gag gag cag ttc aac agc act ttc cgc tca gtc agt gaa ctt ccc atc         1488
Glu Glu Gln Phe Asn Ser Thr Phe Arg Ser Val Ser Glu Leu Pro Ile
            485                 490                 495 atg cac cag gac tgg ctc aat ggc aag gag ttc aaa tgc agg gtc aac         1536
Met His Gln Asp Trp Leu Asn Gly Lys Glu Phe Lys Cys Arg Val Asn
            500                 505                 510 agt gca gct ttc cct gcc ccc atc gag aaa acc atc tcc aaa acc aaa         1584
Ser Ala Ala Phe Pro Ala Pro Ile Glu Lys Thr Ile Ser Lys Thr Lys
        515                 520                 525 ggc aga ccg aag gct cca cag gtg tac acc att cca cct ccc aag gag         1632
Gly Arg Pro Lys Ala Pro Gln Val Tyr Thr Ile Pro Pro Pro Lys Glu
530                 535                 540 cag atg gcc aag gat aaa gtc agt ctg acc tgc atg ata aca gac ttc         1680
Gln Met Ala Lys Asp Lys Val Ser Leu Thr Cys Met Ile Thr Asp Phe
545                 550                 555                 560 ttc cct gaa gac att act gtg gag tgg cag tgg aat ggg cag cca gcg         1728
Phe Pro Glu Asp Ile Thr Val Glu Trp Gln Trp Asn Gly Gln Pro Ala
            565                 570                 575 gag aac tac aag aac act cag ccc atc atg gac aca gat ggc tct tac         1776
Glu Asn Tyr Lys Asn Thr Gln Pro Ile Met Asp Thr Asp Gly Ser Tyr
            580                 585                 590 ttc gtc tac agc aag ctc aat gtg cag aag agc aac tgg gag gca gga         1824
Phe Val Tyr Ser Lys Leu Asn Val Gln Lys Ser Asn Trp Glu Ala Gly
        595                 600                 605 aat act ttc acc tgc tct gtg tta cat gag ggc ctg cac aac cac cat         1872
Asn Thr Phe Thr Cys Ser Val Leu His Glu Gly Leu His Asn His His
610                 615                 620 act gag aag agc ctc tcc cac tct cct ggg ctg caa agc ttg tcg aga         1920
Thr Glu Lys Ser Leu Ser His Ser Pro Gly Leu Gln Ser Leu Ser Arg
625                 630                 635                 640 agt act aga gga tca taa                                                 1938
Ser Thr Arg Gly Ser
```

-continued

```
                645

<210> SEQ ID NO 47
<211> LENGTH: 645
<212> TYPE: PRT
<213> ORGANISM: Artificial
<220> FEATURE:
<223> OTHER INFORMATION: Synthetic Construct

<400> SEQUENCE: 47

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Thr His
            20                  25                  30

Val Thr Gly Gly Asn Ala Gly Arg Thr Thr Ala Gly Leu Val Gly Leu
        35                  40                  45

Leu Thr Pro Gly Ala Lys Gln Asn Ile Gln Leu Ile Asn Thr Asn Gly
    50                  55                  60

Ser Trp His Ile Asn Ser Thr Ala Leu Asn Cys Asn Glu Ser Leu Asn
65                  70                  75                  80

Thr Gly Trp Leu Ala Gly Leu Phe Tyr Gln His Lys Phe Asn Ser Ser
                85                  90                  95

Gly Cys Pro Glu Arg Leu Ala Ser Cys Arg Arg Leu Thr Asp Phe Ala
            100                 105                 110

Gln Gly Trp Gly Pro Ile Ser Tyr Ala Asn Gly Ser Gly Leu Asp Glu
        115                 120                 125

Arg Pro Tyr Cys Trp His Tyr Pro Pro Arg Pro Cys Gly Ile Val Pro
    130                 135                 140

Ala Lys Ser Val Cys Gly Pro Val Tyr Cys Phe Thr Pro Ser Pro Val
145                 150                 155                 160

Val Val Gly Thr Thr Asp Arg Ser Gly Ala Pro Thr Tyr Ser Trp Gly
                165                 170                 175

Ala Asn Asp Thr Asp Val Phe Val Leu Asn Asn Thr Arg Pro Pro Leu
            180                 185                 190

Gly Asn Trp Phe Gly Cys Thr Trp Met Asn Ser Thr Gly Phe Thr Lys
        195                 200                 205

Val Cys Gly Ala Pro Pro Cys Val Ile Gly Gly Val Gly Asn Asn Thr
    210                 215                 220

Leu Leu Cys Pro Thr Asp Cys Phe Arg Lys His Pro Glu Ala Thr Tyr
225                 230                 235                 240

Ser Arg Cys Gly Ser Gly Pro Trp Ile Thr Pro Arg Cys Met Val Asp
                245                 250                 255

Tyr Pro Tyr Arg Leu Trp His Tyr Pro Cys Thr Ile Asn Tyr Thr Ile
            260                 265                 270

Phe Lys Val Arg Met Tyr Val Gly Gly Val Glu His Arg Leu Glu Ala
        275                 280                 285

Ala Cys Asn Trp Thr Arg Gly Glu Arg Cys Asp Leu Glu Asp Arg Asp
    290                 295                 300

Arg Ser Glu Leu Ser Pro Leu Leu Leu Ser Thr Thr Gln Trp Gln Val
305                 310                 315                 320

Leu Pro Cys Ser Phe Thr Thr Leu Pro Ala Leu Ser Thr Gly Leu Ile
                325                 330                 335

His Leu His Gln Asn Ile Val Asp Val Gln Tyr Leu Tyr Gly Val Gly
            340                 345                 350

Ser Ser Ile Ala Ser Trp Ala Ile Lys Trp Glu Tyr Val Val Leu Leu
        355                 360                 365
```

```
Phe Leu Leu Leu Ala Asp Ala Arg Val Cys Ser Cys Leu Trp Met Met
        370                 375                 380

Leu Leu Ile Ser Gln Ala Glu Ala Ala Gly Leu Val Arg Pro Gln Gly
385                 390                 395                 400

Gly Gly Ser Val Asp Lys Lys Ile Val Pro Arg Asp Cys Gly Cys Lys
                405                 410                 415

Pro Cys Ile Cys Thr Val Pro Glu Val Ser Ser Val Phe Ile Phe Pro
                420                 425                 430

Pro Lys Pro Lys Asp Val Leu Thr Ile Thr Leu Thr Pro Lys Val Thr
                435                 440                 445

Cys Val Val Val Asp Ile Ser Lys Asp Asp Pro Glu Val Gln Phe Ser
    450                 455                 460

Trp Phe Val Asp Asp Val Glu Val His Thr Ala Gln Thr Gln Pro Arg
465                 470                 475                 480

Glu Glu Gln Phe Asn Ser Thr Phe Arg Ser Val Ser Glu Leu Pro Ile
                485                 490                 495

Met His Gln Asp Trp Leu Asn Gly Lys Glu Phe Lys Cys Arg Val Asn
                500                 505                 510

Ser Ala Ala Phe Pro Ala Pro Ile Glu Lys Thr Ile Ser Lys Thr Lys
                515                 520                 525

Gly Arg Pro Lys Ala Pro Gln Val Tyr Thr Ile Pro Pro Pro Lys Glu
                530                 535                 540

Gln Met Ala Lys Asp Lys Val Ser Leu Thr Cys Met Ile Thr Asp Phe
545                 550                 555                 560

Phe Pro Glu Asp Ile Thr Val Glu Trp Gln Trp Asn Gly Gln Pro Ala
                565                 570                 575

Glu Asn Tyr Lys Asn Thr Gln Pro Ile Met Asp Thr Asp Gly Ser Tyr
                580                 585                 590

Phe Val Tyr Ser Lys Leu Asn Val Gln Lys Ser Asn Trp Glu Ala Gly
                595                 600                 605

Asn Thr Phe Thr Cys Ser Val Leu His Glu Gly Leu His Asn His His
                610                 615                 620

Thr Glu Lys Ser Leu Ser His Ser Pro Gly Leu Gln Ser Leu Ser Arg
625                 630                 635                 640

Ser Thr Arg Gly Ser
                645

<210> SEQ ID NO 48
<211> LENGTH: 2517
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(2517)

<400> SEQUENCE: 48 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc tac caa      96
Thr Glu Asn Leu Tyr Phe Gln Gly Ala Met Asp Pro Glu Phe Tyr Gln
            20                  25                  30 gtg cgc aat tcc tcg ggg ctt tac cat gtc acc aat gat tgc cct aac      144
Val Arg Asn Ser Ser Gly Leu Tyr His Val Thr Asn Asp Cys Pro Asn
        35                  40                  45
```

```
tcg agt att gtg tac gag gcg gcc gat gcc atc ctg cac act ccg ggg      192
Ser Ser Ile Val Tyr Glu Ala Ala Asp Ala Ile Leu His Thr Pro Gly
    50              55                  60 tgt gtc cct tgc gtt cgc gag ggt aac gcc tcg agg tgt tgg gtg gcg      240
Cys Val Pro Cys Val Arg Glu Gly Asn Ala Ser Arg Cys Trp Val Ala
65              70                  75                  80 gtg acc ccc acg gtg gcc acc agg gac ggc aaa ctc ccc aca acg cag      288
Val Thr Pro Thr Val Ala Thr Arg Asp Gly Lys Leu Pro Thr Thr Gln
                85                  90                  95 ctt cga cgt cat atc gat ctg ctt gtc ggg agc gcc acc ctc tgc tcg      336
Leu Arg Arg His Ile Asp Leu Leu Val Gly Ser Ala Thr Leu Cys Ser
            100                 105                 110 gcc ctc tac gtg ggg gac ctg tgc ggg tct gtc ttt ctt gtt ggt caa      384
Ala Leu Tyr Val Gly Asp Leu Cys Gly Ser Val Phe Leu Val Gly Gln
        115                 120                 125 ctg ttt acc ttc tct ccc agg cgc cac tgg acg acg caa gac tgc aat      432
Leu Phe Thr Phe Ser Pro Arg Arg His Trp Thr Thr Gln Asp Cys Asn
    130                 135                 140 tgt tct atc tat ccc ggc cat ata acg ggt cat cgc atg gca tgg gat      480
Cys Ser Ile Tyr Pro Gly His Ile Thr Gly His Arg Met Ala Trp Asp
145                 150                 155                 160 atg atg atg aac tgg tcc cct acg gca gcg ttg gtg gta gct cag ctg      528
Met Met Met Asn Trp Ser Pro Thr Ala Ala Leu Val Val Ala Gln Leu
                165                 170                 175 ctc cgg atc cca caa gcc atc atg gac atg atc gct ggt gct cac tgg      576
Leu Arg Ile Pro Gln Ala Ile Met Asp Met Ile Ala Gly Ala His Trp
            180                 185                 190 gga gtc ctg gcg ggc ata gcg tat ttc tcc atg gtg ggg aac tgg gcg      624
Gly Val Leu Ala Gly Ile Ala Tyr Phe Ser Met Val Gly Asn Trp Ala
        195                 200                 205 aag gtc ctg gta gtg ctg ctg cta ttt gcc ggc gtc gac gcg gaa acc      672
Lys Val Leu Val Val Leu Leu Leu Phe Ala Gly Val Asp Ala Glu Thr
    210                 215                 220 cac gtc acc ggg gga aat gcc ggc cgc acc acg gct ggg ctt gtt ggt      720
His Val Thr Gly Gly Asn Ala Gly Arg Thr Thr Ala Gly Leu Val Gly
225                 230                 235                 240 ctc ctt aca cca ggc gcc aag cag aac atc caa ctg atc aac acc aac      768
Leu Leu Thr Pro Gly Ala Lys Gln Asn Ile Gln Leu Ile Asn Thr Asn
                245                 250                 255 ggc agt tgg cac atc aat agc acg gcc ttg aat tgc aat gaa agc ctt      816
Gly Ser Trp His Ile Asn Ser Thr Ala Leu Asn Cys Asn Glu Ser Leu
            260                 265                 270 aac acc ggc tgg tta gca ggg ctc ttc tat caa cac aaa ttc aac tct      864
Asn Thr Gly Trp Leu Ala Gly Leu Phe Tyr Gln His Lys Phe Asn Ser
        275                 280                 285 tca ggc tgt cct gag agg ttg gcc agc tgc cga cgc ctt acc gat ttt      912
Ser Gly Cys Pro Glu Arg Leu Ala Ser Cys Arg Arg Leu Thr Asp Phe
    290                 295                 300 gcc cag ggc tgg ggt cct atc agt tat gcc aac gga agc ggc ctc gac      960
Ala Gln Gly Trp Gly Pro Ile Ser Tyr Ala Asn Gly Ser Gly Leu Asp
305                 310                 315                 320 gaa cgc ccc tac tgc tgg cac tac cct cca aga cct tgt ggc att gtg     1008
Glu Arg Pro Tyr Cys Trp His Tyr Pro Pro Arg Pro Cys Gly Ile Val
                325                 330                 335 ccc gca aag agc gtg tgt ggc ccg gta tat tgc ttc act ccc agc ccc     1056
Pro Ala Lys Ser Val Cys Gly Pro Val Tyr Cys Phe Thr Pro Ser Pro
            340                 345                 350 gtg gtg gtg gga acg acc gac agg tcg ggc gcg cct acc tac agc tgg     1104
Val Val Val Gly Thr Thr Asp Arg Ser Gly Ala Pro Thr Tyr Ser Trp
        355                 360                 365
```

```
ggt gca aat gat acg gat gtc ttc gtc ctt aac aac acc agg cca ccg    1152
Gly Ala Asn Asp Thr Asp Val Phe Val Leu Asn Asn Thr Arg Pro Pro
    370             375             380 ctg ggc aat tgg ttc ggt tgt acc tgg atg aac tca act gga ttc acc    1200
Leu Gly Asn Trp Phe Gly Cys Thr Trp Met Asn Ser Thr Gly Phe Thr
385             390             395             400 aaa gtg tgc gga gcg ccc cct tgt gtc atc gga ggg gtg ggc aac aac    1248
Lys Val Cys Gly Ala Pro Pro Cys Val Ile Gly Gly Val Gly Asn Asn
                405             410             415 acc ttg ctc tgc ccc act gat tgc ttc cgc aaa cat ccg gaa gcc aca    1296
Thr Leu Leu Cys Pro Thr Asp Cys Phe Arg Lys His Pro Glu Ala Thr
            420             425             430 tac tct cgg tgc ggc tcc ggt ccc tgg att aca ccc agg tgc atg gtc    1344
Tyr Ser Arg Cys Gly Ser Gly Pro Trp Ile Thr Pro Arg Cys Met Val
        435             440             445 gac tac ccg tat agg ctt tgg cac tat cct tgt acc atc aat tac acc    1392
Asp Tyr Pro Tyr Arg Leu Trp His Tyr Pro Cys Thr Ile Asn Tyr Thr
    450             455             460 ata ttc aaa gtc agg atg tac gtg gga ggg gtc gag cac agg ctg gaa    1440
Ile Phe Lys Val Arg Met Tyr Val Gly Gly Val Glu His Arg Leu Glu
465             470             475             480 gcg gcc tgc aac tgg acg cgg ggc gaa cgc tgt gat ctg gaa gac agg    1488
Ala Ala Cys Asn Trp Thr Arg Gly Glu Arg Cys Asp Leu Glu Asp Arg
                485             490             495 gac agg tcc gag ctc agc ccg ttg ctg ctc tcc acc aca cag tgg cag    1536
Asp Arg Ser Glu Leu Ser Pro Leu Leu Leu Ser Thr Thr Gln Trp Gln
            500             505             510 gtc ctt ccg tgt tct ttc acg acc ctg cca gcc ttg tcc acc ggc ctc    1584
Val Leu Pro Cys Ser Phe Thr Thr Leu Pro Ala Leu Ser Thr Gly Leu
        515             520             525 atc cac ctc cac cag aac att gtg gac gtg cag tac ttg tac ggg gta    1632
Ile His Leu His Gln Asn Ile Val Asp Val Gln Tyr Leu Tyr Gly Val
    530             535             540 ggg tca agc atc gcg tcc tgg gcc att aag tgg gag tac gtc gtt ctc    1680
Gly Ser Ser Ile Ala Ser Trp Ala Ile Lys Trp Glu Tyr Val Val Leu
545             550             555             560 ctg ttc ctt ctg ctt gca gac gcg cgc gtc tgc tcc tgc ttg tgg atg    1728
Leu Phe Leu Leu Leu Ala Asp Ala Arg Val Cys Ser Cys Leu Trp Met
                565             570             575 atg tta ctc ata tcc caa gcg gag gcg gct gga cta gtg cgg ccg caa    1776
Met Leu Leu Ile Ser Gln Ala Glu Ala Ala Gly Leu Val Arg Pro Gln
            580             585             590 ggc ggc gga tcc gtg gac aag aaa att gtg ccc agg gat tgt ggt tgt    1824
Gly Gly Gly Ser Val Asp Lys Lys Ile Val Pro Arg Asp Cys Gly Cys
        595             600             605 aag cct tgc ata tgt aca gtc cca gaa gta tca tct gtc ttc atc ttc    1872
Lys Pro Cys Ile Cys Thr Val Pro Glu Val Ser Ser Val Phe Ile Phe
    610             615             620 ccc cca aag ccc aag gat gtg ctc acc att act ctg act cct aag gtc    1920
Pro Pro Lys Pro Lys Asp Val Leu Thr Ile Thr Leu Thr Pro Lys Val
625             630             635             640 acg tgt gtt gtg gta gac atc agc aag gat gat ccc gag gtc cag ttc    1968
Thr Cys Val Val Val Asp Ile Ser Lys Asp Asp Pro Glu Val Gln Phe
                645             650             655 agc tgg ttt gta gat gat gtg gag gtg cac aca gct cag acg caa ccc    2016
Ser Trp Phe Val Asp Asp Val Glu Val His Thr Ala Gln Thr Gln Pro
            660             665             670 cgg gag gag cag ttc aac agc act ttc cgc tca gtc agt gaa ctt ccc    2064
Arg Glu Glu Gln Phe Asn Ser Thr Phe Arg Ser Val Ser Glu Leu Pro
        675             680             685
```

-continued

```
atc atg cac cag gac tgg ctc aat ggc aag gag ttc aaa tgc agg gtc    2112
Ile Met His Gln Asp Trp Leu Asn Gly Lys Glu Phe Lys Cys Arg Val
    690             695                 700 aac agt gca gct ttc cct gcc ccc atc gag aaa acc atc tcc aaa acc    2160
Asn Ser Ala Ala Phe Pro Ala Pro Ile Glu Lys Thr Ile Ser Lys Thr
705             710                 715                 720 aaa ggc aga ccg aag gct cca cag gtg tac acc att cca cct ccc aag    2208
Lys Gly Arg Pro Lys Ala Pro Gln Val Tyr Thr Ile Pro Pro Pro Lys
                725                 730                 735 gag cag atg gcc aag gat aaa gtc agt ctg acc tgc atg ata aca gac    2256
Glu Gln Met Ala Lys Asp Lys Val Ser Leu Thr Cys Met Ile Thr Asp
            740                 745                 750 ttc ttc cct gaa gac att act gtg gag tgg cag tgg aat ggg cag cca    2304
Phe Phe Pro Glu Asp Ile Thr Val Glu Trp Gln Trp Asn Gly Gln Pro
        755                 760                 765 gcg gag aac tac aag aac act cag ccc atc atg gac aca gat ggc tct    2352
Ala Glu Asn Tyr Lys Asn Thr Gln Pro Ile Met Asp Thr Asp Gly Ser
    770                 775                 780 tac ttc gtc tac agc aag ctc aat gtg cag aag agc aac tgg gag gca    2400
Tyr Phe Val Tyr Ser Lys Leu Asn Val Gln Lys Ser Asn Trp Glu Ala
785                 790                 795                 800 gga aat act ttc acc tgc tct gtg tta cat gag ggc ctg cac aac cac    2448
Gly Asn Thr Phe Thr Cys Ser Val Leu His Glu Gly Leu His Asn His
                805                 810                 815 cat act gag aag agc ctc tcc cac tct cct ggg ctg caa agc ttg tcg    2496
His Thr Glu Lys Ser Leu Ser His Ser Pro Gly Leu Gln Ser Leu Ser
            820                 825                 830 aga agt act aga gga tca taa                                        2517
Arg Ser Thr Arg Gly Ser
        835
```

<210> SEQ ID NO 49
<211> LENGTH: 838
<212> TYPE: PRT
<213> ORGANISM: Artificial
<220> FEATURE:
<223> OTHER INFORMATION: Synthetic Construct

<400> SEQUENCE: 49

```
Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Tyr Gln
            20                  25                  30

Val Arg Asn Ser Ser Gly Leu Tyr His Val Thr Asn Asp Cys Pro Asn
        35                  40                  45

Ser Ser Ile Val Tyr Glu Ala Ala Asp Ala Ile Leu His Thr Pro Gly
    50                  55                  60

Cys Val Pro Cys Val Arg Glu Gly Asn Ala Ser Arg Cys Trp Val Ala
65                  70                  75                  80

Val Thr Pro Thr Val Ala Thr Arg Asp Gly Lys Leu Pro Thr Thr Gln
                85                  90                  95

Leu Arg Arg His Ile Asp Leu Leu Val Gly Ser Ala Thr Leu Cys Ser
            100                 105                 110

Ala Leu Tyr Val Gly Asp Leu Cys Gly Ser Val Phe Leu Val Gly Gln
        115                 120                 125

Leu Phe Thr Phe Ser Pro Arg Arg His Trp Thr Thr Gln Asp Cys Asn
    130                 135                 140

Cys Ser Ile Tyr Pro Gly His Ile Thr Gly His Arg Met Ala Trp Asp
145                 150                 155                 160
```

```
Met Met Met Asn Trp Ser Pro Thr Ala Ala Leu Val Val Ala Gln Leu
                165                 170                 175

Leu Arg Ile Pro Gln Ala Ile Met Asp Met Ile Ala Gly Ala His Trp
            180                 185                 190

Gly Val Leu Ala Gly Ile Ala Tyr Phe Ser Met Val Gly Asn Trp Ala
        195                 200                 205

Lys Val Leu Val Val Leu Leu Leu Phe Ala Gly Val Asp Ala Glu Thr
    210                 215                 220

His Val Thr Gly Gly Asn Ala Gly Arg Thr Thr Ala Gly Leu Val Gly
225                 230                 235                 240

Leu Leu Thr Pro Gly Ala Lys Gln Asn Ile Gln Leu Ile Asn Thr Asn
            245                 250                 255

Gly Ser Trp His Ile Asn Ser Thr Ala Leu Asn Cys Asn Glu Ser Leu
        260                 265                 270

Asn Thr Gly Trp Leu Ala Gly Leu Phe Tyr Gln His Lys Phe Asn Ser
    275                 280                 285

Ser Gly Cys Pro Glu Arg Leu Ala Ser Cys Arg Arg Leu Thr Asp Phe
290                 295                 300

Ala Gln Gly Trp Gly Pro Ile Ser Tyr Ala Asn Gly Ser Gly Leu Asp
305                 310                 315                 320

Glu Arg Pro Tyr Cys Trp His Tyr Pro Pro Arg Pro Cys Gly Ile Val
            325                 330                 335

Pro Ala Lys Ser Val Cys Gly Pro Val Tyr Cys Phe Thr Pro Ser Pro
        340                 345                 350

Val Val Val Gly Thr Thr Asp Arg Ser Gly Ala Pro Thr Tyr Ser Trp
    355                 360                 365

Gly Ala Asn Asp Thr Asp Val Phe Val Leu Asn Asn Thr Arg Pro Pro
370                 375                 380

Leu Gly Asn Trp Phe Gly Cys Thr Trp Met Asn Ser Thr Gly Phe Thr
385                 390                 395                 400

Lys Val Cys Gly Ala Pro Pro Cys Val Ile Gly Val Gly Val Asn Asn
            405                 410                 415

Thr Leu Leu Cys Pro Thr Asp Cys Phe Arg Lys His Pro Glu Ala Thr
        420                 425                 430

Tyr Ser Arg Cys Gly Ser Gly Pro Trp Ile Thr Pro Arg Cys Met Val
    435                 440                 445

Asp Tyr Pro Tyr Arg Leu Trp His Tyr Pro Cys Thr Ile Asn Tyr Thr
450                 455                 460

Ile Phe Lys Val Arg Met Tyr Val Gly Gly Val Glu His Arg Leu Glu
465                 470                 475                 480

Ala Ala Cys Asn Trp Thr Arg Gly Glu Arg Cys Asp Leu Glu Asp Arg
            485                 490                 495

Asp Arg Ser Glu Leu Ser Pro Leu Leu Leu Ser Thr Thr Gln Trp Gln
        500                 505                 510

Val Leu Pro Cys Ser Phe Thr Thr Leu Pro Ala Leu Ser Thr Gly Leu
    515                 520                 525

Ile His Leu His Gln Asn Ile Val Asp Val Gln Tyr Leu Tyr Gly Val
530                 535                 540

Gly Ser Ser Ile Ala Ser Trp Ala Ile Lys Trp Glu Tyr Val Val Leu
545                 550                 555                 560

Leu Phe Leu Leu Leu Ala Asp Ala Arg Val Cys Ser Cys Leu Trp Met
            565                 570                 575

Met Leu Leu Ile Ser Gln Ala Glu Ala Ala Gly Leu Val Arg Pro Gln
        580                 585                 590
```

```
Gly Gly Gly Ser Val Asp Lys Lys Ile Val Pro Arg Asp Cys Gly Cys
            595                 600                 605

Lys Pro Cys Ile Cys Thr Val Pro Glu Val Ser Ser Val Phe Ile Phe
        610                 615                 620

Pro Pro Lys Pro Lys Asp Val Leu Thr Ile Thr Leu Thr Pro Lys Val
625                 630                 635                 640

Thr Cys Val Val Val Asp Ile Ser Lys Asp Asp Pro Glu Val Gln Phe
                645                 650                 655

Ser Trp Phe Val Asp Asp Val Glu Val His Thr Ala Gln Thr Gln Pro
            660                 665                 670

Arg Glu Glu Gln Phe Asn Ser Thr Phe Arg Ser Val Ser Glu Leu Pro
        675                 680                 685

Ile Met His Gln Asp Trp Leu Asn Gly Lys Glu Phe Lys Cys Arg Val
        690                 695                 700

Asn Ser Ala Ala Phe Pro Ala Pro Ile Glu Lys Thr Ile Ser Lys Thr
705                 710                 715                 720

Lys Gly Arg Pro Lys Ala Pro Gln Val Tyr Thr Ile Pro Pro Pro Lys
                725                 730                 735

Glu Gln Met Ala Lys Asp Lys Val Ser Leu Thr Cys Met Ile Thr Asp
            740                 745                 750

Phe Phe Pro Glu Asp Ile Thr Val Glu Trp Gln Trp Asn Gly Gln Pro
        755                 760                 765

Ala Glu Asn Tyr Lys Asn Thr Gln Pro Ile Met Asp Thr Asp Gly Ser
    770                 775                 780

Tyr Phe Val Tyr Ser Lys Leu Asn Val Gln Lys Ser Asn Trp Glu Ala
785                 790                 795                 800

Gly Asn Thr Phe Thr Cys Ser Val Leu His Glu Gly Leu His Asn His
                805                 810                 815

His Thr Glu Lys Ser Leu Ser His Ser Pro Gly Leu Gln Ser Leu Ser
            820                 825                 830

Arg Ser Thr Arg Gly Ser
            835

<210> SEQ ID NO 50
<211> LENGTH: 9
<212> TYPE: PRT
<213> ORGANISM: Hepatitis B virus

<400> SEQUENCE: 50

Gly Met Leu Thr Pro Val Ser Thr Ile
1               5

<210> SEQ ID NO 51
<211> LENGTH: 9
<212> TYPE: PRT
<213> ORGANISM: Hepatitis B virus

<400> SEQUENCE: 51

Asn Ile Ala Ser His Ile Ser Ser Ile
1               5
```

CHIMERIC ANTIGENS FOR BREAKING HOST TOLERANCE TO FOREIGN ANTIGENS

RELATED APPLICATIONS

This application claims the benefit of U.S. Provisional Application No. 60/493,449, filed Aug. 8, 2003, which is herein incorporated by reference.

I. INTRODUCTION

A. Technical Field

The present invention relates to methods and compositions for eliciting or enhancing an immune response and for breaking host tolerance to foreign antigens.

B. Background

When a healthy host (human or animal) encounters a foreign antigen, such as a protein derived from a bacterium, virus and/or parasite, the host normally initiates an immune response. This immune response can be a humoral response and/or a cellular response. In the humoral response, antibodies are produced by B cells and are secreted into the blood and/or lymph in response to an antigenic stimulus. The antibody then neutralizes the antigen, e.g. a virus, by binding specifically to antigens on its surface, marking it for destruction by phagocytotic cells and/or complement-mediated mechanisms, or by blocking binding or by enhancing clearance of free antigen from circulation. The cellular response is characterized by the selection and expansion of specific helper and cytotoxic T-lymphocytes capable of directly or indirectly eliminating the cells that contain the antigen.

In some individuals, the immune system fails to respond to certain foreign antigens. When an antigen does not stimulate the production of specific antibodies and/or killer T cells, the immune system is unable to prevent the resultant disease. Thus, the infectious agent, e.g. a virus, can establish a chronic infection and the host immune system becomes tolerant to the antigens produced by the infectious agent.

While the mechanism by which the infectious agent evades the host immune machinery is not clearly established, the lack of proper presentation of foreign antigens to the host immune system may be a contributing factor to development of chronic infections. Antigen presenting cells (APCs) process the encountered antigens differently depending on the localization of the antigen. Exogenous antigens are endocytosed and subsequently processed within the endosomes of the antigen presenting cell. The peptide fragments generated from exogenous antigens are presented on the surface of the cell complexed with Major Histocompatibility Complex (MHC) Class II. The presentation of this complex to $CD4^+$ T cells stimulates the $CD4^+$ T helper cells to secrete cytokines that stimulate B cells to produce antibodies against the exogenous antigen (humoral response). Intracellular antigens, on the other hand, are processed and presented as complexes with MHC Class I on the surface of antigen presenting cells. Antigen presentation to $CD8^+$ T cells results in a cytotoxic T cell (CTL) immune response against host cells that carry the antigen.

In subjects with chronic viral or parasitic infections (where the organism is resident inside a host cell at some point during its life cycle), antigens will be produced by and expressed in the host cell and secreted antigens will be present in the circulation. As an example, in the case of a chronic human hepatitis B virus (HBV) carrier, virions and the HBV surface antigens and a surrogate of core antigens (in the form of the e-antigen) can be detected in the blood.

An effective therapy for a chronic infection requires a strong CTL response against antigens associated with the infectious agent. This can be achieved either by producing the antigen within the host cell, or delivering the antigen to the appropriate cellular compartment so that it gets processed and presented so as to elicit a cellular response. Several approaches have been documented in the literature to deliver an antigen intracellularly. Among these, viral vectors (Lorenz et al., *Hum. Gen. Ther.* 10:623-631 (1999)), the use of cDNA-transfected cells (Donnelly et al., *Ann. Rev. Immunol.* 15:617 (1997)) as well as the expression of the antigen through injected cDNA vectors (Lai et al., *Crit. Rev. Immunol.* 18:449-484 (1988); and U.S. Pat. No. 5,589,466), have been documented. Further, DNA vaccines expressing antigens targeted to dendritic cells have been described (You, et al., *Cancer Res* 61:3704-3711 (2001)).

Delivery vehicles capable of carrying the antigens to the cytosolic compartment of the cell for MHC Class I pathway processing have also been used. Hilgers, et al. (*Vaccine* 17: 219-228 (1999)) have described in detail the use of adjuvants to achieve the same goal. Another approach is the use of biodegradable microspheres for cytoplasmic delivery of antigens, exemplified by the generation of a Th1 immune response against ovalbumin peptide (Newman, et al., *J Control Release* 54:49-59 (1998); and Newman, et al., *J Biomed Mater Res* 50:591-597 (2000)). Additionally, antigen presenting cells, e.g., dendritic cells, take up PLGA nanospheres (Newman, et al., *J Biomed Mater Res* 60:480-486 (2002)).

The ability of dendritic cells to capture, process, and present the antigen and to stimulate naïve T cells has made them very important tools for therapeutic vaccine development (Laupeze, et al., *Hum Immunol* 60:591-597 (1999)). Targeting of the antigen to the dendritic cells is a crucial step in antigen presentation and the presence of several receptors on dendritic cells for the Fc region of antibodies have been exploited for this purpose (Regnault, et al., *J Exp Med* 189: 371-380 (1999)). Additional examples of this approach include ovarian cancer Mab-B43.13, Anti-PSA antibody as well as Anti-HBV antibody antigen complexes (Wen, et al., *Int Rev Immunol* 18:251-258 (1999)). Cancer immunotherapy using dendritic cells loaded with tumor associated antigens has been shown to produce tumor-specific immune responses and anti-tumor activity (Fong and Engleman, *Ann Rev Immunol* 96:1865-1972 (2000); and Campton, et al. *J Invest Dermatol* 115:57-61 (2000)). Promising results were obtained in clinical trials in vivo using tumor-antigen-pulsed dendritic cells (Tarte and Klein, *Leukemia* 13:653-663 (1999)). These studies clearly demonstrate the efficacy of using dendritic cells to generate immune responses against cancer antigens.

Antigen presentation can also be affected via mannose receptors, in place of, or in addition to, utilizing the Fc receptor on antigen presenting cells. The macrophage mannose receptor (MMR), also known as CD206, is expressed on antigen presenting cells such as dendritic cells (DC). This molecule is a member of the C-type lectin family of endocytic receptors. Mannosylated antigens can be bound and internalized by CD206. In general, exogenous antigen is thought to be processed and presented primarily through the MHC class II pathway. However, in the case of targeting through CD206, there is evidence that both the MHC class I and class II pathways are involved (Apostolopoulos et al., *Eur. J. Immunol.* 30:1714 (2000); Apostolopoulos and McKenzie, *Curr. Mol. Med.* 1:469 (2001); Ramakrishna et al., *J. Immunol.* 172:2845-2852 (2004)).

Infectious disease and cancer are major public healthcare issues. For example, World Health Organization statistics show that more than 2 billion people have been infected by HBV. Among these, 370 million are chronically infected and, as a result, have a high probability of developing cirrhosis of the liver and hepatocellular carcinoma. Approximately 170 million people worldwide are chronic carriers of HCV, for which there is no effective prophylactic or therapeutic vaccine. The World Health Organization reports that 10 million people are diagnosed with cancer every year. Cancer causes 6 million deaths every year, 12% of deaths worldwide. Thus a need exists for new, therapeutically effective compositions and methods for the eliciting immune responses against infections and cancer, as well as new methods for producing such compositions.

II. SUMMARY OF THE INVENTION

The invention provides chimeric antigens for eliciting an immune response, the chimeric antigens comprising an immune response domain and a target binding domain, wherein the target binding domain comprises an antibody fragment.

Another aspect of the invention provides methods of enhancing antigen presentation in an antigen presenting cell comprising contacting the antigen presenting cell with a composition comprising a chimeric antigen of the invention.

Yet another aspect of the invention provides methods of activating antigen presenting cells comprising contacting the antigen presenting cells with a chimeric antigen of the invention.

An aspect of the invention provides methods of eliciting an immune response comprising administering to a subject, a composition comprising a chimeric antigen of the invention.

Another aspect of the invention provides methods of breaking tolerance comprising administering a chimeric antigen of the invention to a subject. In a preferred embodiment, the subject is chronically infected with a virus or an obligate intracellular parasite.

One aspect of the invention provides methods of treating an immune-treatable condition comprising administering, to a subject in need thereof, a therapeutically effective amount of a chimeric antigen of the invention. In a preferred embodiment, the immune-treatable condition is an infection, especially a chronic infection, or a cancer.

Yet another aspect of the invention provides methods of vaccinating a subject against an infection comprising administering a chimeric antigen of the present invention to the subject. The subject can be prophylactically or therapeutically vaccinated. In a preferred embodiment, the subject develops an immune response to more than one epitope of the chimeric antigen, and more preferably to more than one epitope of the immune response domain Preferably, the infection is a viral infection or an obligate intracellular parasitic infection.

Another aspect of the invention provides a pharmaceutical composition comprising a chimeric antigen of the present invention and a pharmaceutically acceptable excipient.

An aspect of the invention provides articles of manufacture comprising a chimeric antigen of the invention and instructions for administering the chimeric antigen to a subject in need thereof.

Another aspect of the invention provides polynucleotides encoding a chimeric antigen, said polynucleotide comprising a first polynucleotide portion encoding an immune response domain and a second polynucleotide portion encoding a target binding domain, wherein the target binding domain comprises an antibody fragment. The invention also provides microorganisms and cell lines comprising such polynucleotides Yet another aspect of the invention provides methods of producing a chimeric antigen of the invention comprising providing a microorganism or cell line, which comprises a polynucleotide that encodes a chimeric antigen of the invention, and culturing the microorganism or cell line under conditions whereby the chimeric antigen is expressed The details of one or more embodiments of the invention are set forth in the accompanying drawings and the description below. Other features, objects, and advantages of the invention will be apparent from the description and drawings, and from the claims.

III. DESCRIPTION OF DRAWINGS

FIG. 1A provides a schematic diagram illustrating the structure of a chimeric antigen of the present invention as a monomer, wherein the chimeric antigen has two portions, namely an immune response domain and a target binding domain. The schematic also illustrates a preferred embodiment, in which a hinge region is present. FIG. 1B provides a schematic diagram illustrating the structure of a chimeric antigen of invention in its normal state, assembled as a dimer. This schematic illustrates a particularly preferred embodiment, in which the chimeric antigen comprises a 6×His tag and peptide linker in addition to the immune response and target binding domains.

FIG. 2 demonstrates that stimulation of T cells with HBV S1/S2-TBD generates a cytotoxic T cell (CTL) response specifically against an epitope from the HBV S1 protein.

FIG. 3 demonstrates that stimulation of T cells with HBV S1/S2-TBD generates a cytotoxic T cell (CTL) response specifically against an epitope from the HBV S2 protein.

FIG. 4 shows the comparison of uptake of HBV S1/S2-TBD, IgG1, and IgG2 by maturing dendritic cells as a function of concentration.

FIG. 5 shows the correlation of HBV S1/S2-TBD binding to CD32 and CD206 expression on dendritic cells.

IV. DETAILED DESCRIPTION

A. Overview

Disclosed herein are compositions and methods for eliciting immune responses against antigens. In particular, the compounds and methods elicit immune responses against foreign antigens that are otherwise recognized by the host as "self" antigens, thus breaking host tolerance to those antigens. Presenting the host immune system with a chimeric antigen comprising an immune response domain and a target binding domain, wherein the target binding domain comprises an antibody fragment, enhances the immune response against the foreign or tolerated antigen. Antigen presenting cells take up, process, and present the chimeric antigen, eliciting both a humoral and cellular immune response against the desired antigen.

B. Definitions

Prior to describing the invention in further detail, the terms used in this application are defined as follows unless otherwise indicated.

"Antibody" refers to an immunoglobulin molecule produced by B lymphoid cells with a specific amino acid sequence evoked in humans or other animals by an antigen (immunogen). These molecules are characterized by reacting specifically with the antigen, each being defined in terms of the other.

"Antibody response" or "humoral response" refers to a type of immune response in which antibodies are produced by B lymphoid cells and are secreted into the blood and/or lymph in response to an antigenic stimulus. In a properly functioning immune response, the antibody binds specifically to antigens on the surface of cells (e.g., a pathogen), marking the cell for destruction by phagocytotic cells and/or complement-mediated mechanisms. Antibodies also circulate systemically and can bind to free virions. This antibody binding can neutralize the virion and prevent it from infecting a cell as well as marking the virion for elimination from circulation by phagocytosis or filtration in the kidneys.

"Antigen" refers to any substance that, as a result of coming in contact with appropriate cells, induces a state of sensitivity and/or immune responsiveness and that reacts in a demonstrable way with antibodies and/or immune cells of the sensitized subject in vivo or ex vivo.

"Antigen-presenting cell" refers to the accessory cells of antigen inductive events that function primarily by handling and presenting antigen to lymphocytes. The interaction of antigen presenting cells with antigens is an essential step in immune induction because it enables lymphocytes to encounter and recognize antigenic molecules and to become activated. Exemplary antigen presenting cells include macrophages, Langerhans-dendritic cells, Follicular dendritic cells, and B cells.

"B cell" refers to a type of lymphocyte that produces immunoglobulins or antibodies that interact with antigens.

"$C_H1$ region" refers to a region of the heavy chain constant domain on the antigen binding fragment of an antibody.

"Cellular response" refers to a type of immune response mediated by specific helper and killer T cells capable of directly eliminating virally infected or cancerous cells.

As used herein, the term "chimeric antigen" refers to a polypeptide comprising an immune response domain and a target binding domain. The immune response domain and target binding domains may be directly or indirectly linked by covalent or non-covalent means.

"Cytotoxic T-lymphocyte" is a specialized type of lymphocyte capable of destroying foreign cells and host cells infected with the infectious agents that produce viral antigens.

"Epitope" refers to the simplest form of an antigenic determinant, on a complex antigen molecule; this is the specific portion of an antigen that is recognized by an immunoglobulin or T cell receptor.

"Fusion protein" refers to a protein formed by expression of a hybrid gene made by combining two or more gene sequences.

"Hinge region" refers to the portion of an antibody that connects the Fab fragment to the Fc fragment; the hinge region contains disulfide bonds that covalently link the two heavy chains.

The term "homolog" refers to a molecule which exhibits homology to another molecule, by for example, having sequences of chemical residues that are the same or similar at corresponding positions. The phrase "% homologous" or "% homology" refers to the percent of nucleotides or amino acids at the same position of homologous polynucleotides or polypeptides that are identical or similar. For example, if 75 of 80 residues in two proteins are identical, the two proteins are 93.75% homologous. Percent homology can be determined using various software programs known to one of skill in the art.

"Host" refers to a warm-blooded animal, including a human, which suffers from an immune-treatable condition, such as an infection or a cancer. As used herein, "host" also refers to a warm-blooded animal, including a human, to which a chimeric antigen is administered.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances. The terms "hybridize", "hybridizing", "hybridizes" and the like, used in the context of polynucleotides, are meant to refer to conventional hybridization conditions, preferably such as hybridization in 50% formamide/6×SC/0.1% SDS/100 µg/ml mDNA, in which temperatures for hybridization are above 37° C. and temperatures for washing in 0.1×SC/0.1% SDS are above 55° C.

"Immunity" or "immune response" refers to the body's response to an antigen. In particular embodiments, it refers to the ability of the body to resist or protect itself against infectious disease.

"Immune Response Domain (IRD)" refers to the variously configured antigenic portion of the bifunctional chimeric antigen molecule. The immune response domain comprises one or more antigens and/or one or more recombinant antigens.

As used herein, the phrase "immune-treatable condition" refers to a condition or disease that can be prevented, inhibited or relieved by eliciting or modulating an immune response in the subject.

"Lymphocyte" refers to a subset of nucleated cells found in the blood, which mediate specific immune responses.

"Monoclonal antibody" or "mAb" refers to an antibody produced from a clone or genetically homogenous population of fused hybrid cells, i.e., a hybridoma cell. Hybrid cells are cloned to establish cells lines producing a specific monoclonal antibody that is chemically and immunologically homogenous, i.e., that recognizes only one type of antigen.

"Peptide linkage" refers to two or more amino acids covalently joined by a substituted amide linkage between the alpha-amino group of one amino acid and the alpha-carboxyl group of another amino acid.

"Pharmaceutically acceptable" refers to a non-toxic composition that is physiologically compatible with humans or other animals.

A "pharmaceutically acceptable excipient" comprises a material such as an adjuvant, a carrier, pH-adjusting and buffering agents, tonicity adjusting agents, wetting agents, preservatives, and the like, which is non-toxic and physiologically compatible with humans or other animals The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

"Protease cleavage site" refers to a site where proteolytic enzymes hydrolize (break) polypeptide chains.

In the present invention the phrase "stringent hybridization conditions" or "stringent conditions" refers to conditions under which a compound of the invention will hybridize to its target sequence, but to a minimal number of other sequences.

The term "subject" refers to any warm-blooded animal, preferably a human.

"Tag" refers to a marker or marker sequence used to isolate or purify a molecule containing the tag. An exemplary tag includes a 6×His tag.

"T cell" refers to a type of lymphocyte responsible for antigen-specific cellular interactions, and which mediates humoral and cellular immune responses.

"Target Binding Domain (TBD)" refers to a protein comprising an antibody fragment, which is capable of binding to a receptor on an antigen presenting cell, particularly on a dendritic cell, and which is subsequently transported into the antigen presenting cell by receptor-mediated uptake.

The phrase "therapeutically effective amount" refers to an amount of chimeric antigen, or polynucleotide encoding a chimeric antigen, sufficient to elicit an effective B cell, cytotoxic T lymphocyte (CTL) and/or helper T lymphocyte (Th) response to the antigen and to block or to cure or at least partially arrest or slow symptoms and/or complications of a disease or disorder.

The terms "treating" and "treatment" as used herein cover any treatment of a condition treatable by a chimeric antigen in an animal, particularly a human, and include: (i) preventing the condition from occurring in a subject which may be predisposed to the condition but has not yet been diagnosed as having it; (ii) inhibiting the condition, e.g., arresting or slowing its development; or (iii) relieving the condition, e.g., causing regression of the condition or its symptoms "Xenotypic," as used herein, refers to originating from a different species other than the host. For example, a recombinantly expressed antibody cloned from a mouse genome would be xenotypic to a human but not to a mouse, regardless of whether that recombinantly expressed antibody was produced in a bacterial, insect or mouse cell.

C. Novel Chimeric Antigens

The invention provides chimeric antigens for eliciting an immune response comprising an immune response domain and a target binding domain, wherein the target binding domain comprises an antibody fragment. In accordance with the present invention, the chimeric antigen, preferably, is capable of binding to a Fc receptor and/or to a macrophage mannose receptor. The antibody fragment can be xenotypic to the host or not xenotypic to the host.

In preferred embodiments of the invention, the chimeric antigen is capable of inducing humoral and/or cellular immune responses. The cellular immune response can include a Th1 response, a Th2 response, and/or a cytotoxic T lymphocyte (CTL) response. In yet another preferred embodiment, the chimeric antigen elicits a multi-epitopic immune response. The multi-epitopic immune response can include a response to at least one epitope of the immune response domain and/or a response to at least one epitope of the target binding domain. Alternatively, the multi-epitopic response may be limited to a response to more than one epitope of the immune response domain.

Figure 1B:
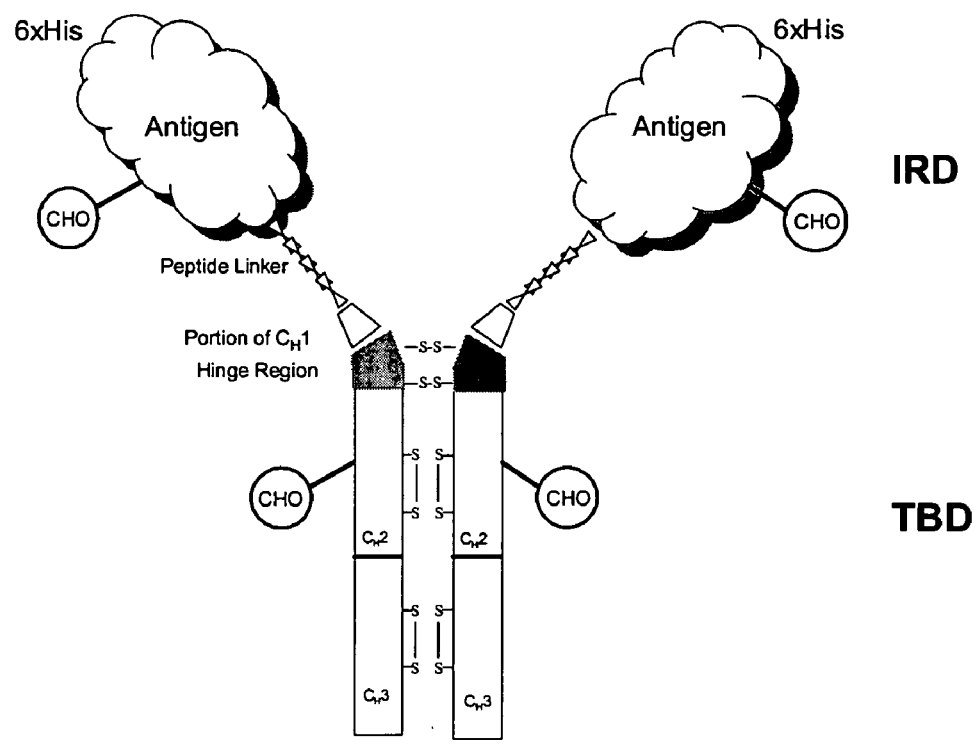

The chimeric antigen of the present invention comprises two portions, namely an immune response domain containing an antigenic sequence (such as a viral antigen), and a target binding domain containing an antibody fragment (FIG. 1). In a preferred embodiment, the immune response domain can be linked to the target binding domain by any method known to those of skill in the art. Linkers for linking the immune response domain to the target binding domain can include, but are not limited to, covalent peptide linkages, chemical conjugation, leucine zippers and biotin/avidin. In a preferred embodiment, the immune response domain and target binding domain are cloned as a single fusion protein. The covalent peptide linkage of the fusion protein may comprise additional peptide sequences, such as SRPQGGGS or VRPQGGGS (SEQ ID NO: 1). In yet another preferred embodiment, various immune response domains are biotinylated and the target binding domain is generated with streptavidin as a fusion protein to facilitate the production of a wide assortment of chimeric antigens. Alternatively, the immune response domain and the target binding domain each can be expressed as a fusion to a leucine zipper moiety, which will cause the two portions of the chimeric antigen to associate upon mixing. Finally, the immune response domain and target binding domains can be expressed separately and then chemically conjugated using methods known to one of skill in the art. Exemplary methods include use of protein cross-linkers, such as dimethyl suberimidate, to covalently attach the two domains.

The immune response domain primarily provides the antigenic portion of the chimeric antigen. The immune response domain comprises at least one antigenic portion of the entity to which an immune response is desired. The chimeric antigen, optionally, can comprise more than one immune response domain. In preferred embodiments, the immune response domain comprises at least one antigenic portion of an infectious agent, such as a virus or an obligate intracellular parasite, or of a cancer antigen. More preferably, the immune response domain comprises at least one antigenic portion of an infectious virus.

Examples of preferred infectious viruses include: Retroviridae (e.g., human immunodeficiency viruses, such as Human Immunodeficiency Virus-1 (HIV-1), also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., Hepatitis C virus, dengue viruses, encephalitis viruses, yellow fever viruses); Coronaviridae (e.g., coronaviruses); Rhabdoviridae (e.g., vesicular stomatitis viruses, rabies viruses); Filoviridae (e.g., Ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (human Hepatitis B virus (HBV), duck Hepatitis B virus (DHBV)); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), Epstein-Barr viruses, herpes viruses); Poxviridae (variola virsues, vaccinia viruses, pox viruses); and Iridoviridae (e.g., African swine fever virus); and unclassified viruses (e.g., the agent of delta hepatitides, the agents of non-A, non-B hepatitis (class 1—internally transmitted); class 2—parenterally transmitted; Norwalk and related viruses, and astroviruses). In some embodiments of the invention, the immune response domain of the chimeric antigen includes at least one antigenic portion of one or more proteins selected from the group consisting of HBV proteins, DHBV proteins, and HCV proteins. Particularly preferred HBV proteins for use in the present invention include, but are not limited to, HBV S1/S2, HBV S1/S2/S, HBV Core, HBV Core ctm (C-terminal modified), HBV e-antigen, and HBV polymerase. Particularly preferred DHBV proteins for use in the present invention include, but are not limited to, DHBV PreS/S, DHBV PreS, DHBV Core, and DHBV polymerase. Particularly preferred HCV proteins for use in the present invention include, but are not limited to, HCV Core (1-191), HCV Core (1-177), HCV E1-E2, HCV E1, HCV E2, HCV NS3, HCV NS5A and NS4A. Other preferred viral antigens for use in the present invention include HIV gp120, HSV alkaline nuclease and human papilloma virus (HPV) capsid proteins L1 and L2, and early region proteins HPV E1, HPV E2, HPV E4, HPV E5, HPV E6, and HPV E7.

Examples of preferred obligate intracellular parasites include: *Tetrahymena* sp. (e.g. *T. pyriformis*), *Plasmodium* sp. (e.g. *P. falciparum*), *Cryptospiridium* sp., *Spraguea* sp. (e.g. *S. lophii*), *Giardia* sp., *Toxoplasma* sp. (e.g. *T. gondii*, *T. cruzi*), *Leishmania* sp., *Rickettsia* sp. (e.g. *R. prowazekii*), *Chlamydia* sp., *Mycobacterium* sp. (e.g. *M. tuberculosis*), *Legionella* sp., *Listeria* sp., (e.g. *L. monocytogenes*), *Coxiella* sp. (e.g. *C. brunette*), *Shigella* sp., *Erlichia* sp., and *Bartonelia* sp. Preferred cancer antiens include: prostate specific antigen (PSA), prostate specific membrane antigen (PSMA), MUC1, CA 125, WT1, Her-2/neu, carcinoembryonic antigen (CEA), MAGE-3, MART-1, gp100, NY-ESSO-1, CA19.9, TAG72, CA 15.3, CA 27.9, gp 120, prostatic acid phosphatase (PAP), Heatshock proteins, alpha-fetoprotein (AFP), Telomerase, and ras.

In yet another embodiment of the invention, the immune response domain of the chimeric antigen includes 6×His tag fused to the one or more antigenic portions.

In accordance with the present invention, the chimeric antigen is a protein capable of binding to an Fc receptor and/or CD206 on an antigen presenting cell, particularly a dendritic cell, and is subsequently transported into the antigen presenting cell by receptor-mediated uptake. In accordance with the present invention, the presence of an antibody fragment augments the uptake of the chimeric antigen through the Fc receptor on antigen-presenting cells, specifically dendritic cells. By virtue of this specific binding and internalization, the viral antigen is processed and presented as foreign. Thus, an immune response can be effectively elicited to a previously tolerated antigen. The target binding domain comprises an antibody fragment that can be xenotypic to the host or not xenotypic to the host. In a preferred embodiment of the invention, the antibody fragment comprises a murine Fc fragment. In a more preferred embodiment of the invention, the target binding domain comprises a Fc fragment, a hinge region, and a portion of the $C_H1$ region, and the chimeric antigen comprises a peptide linker suitable for linking the target binding domain to the immune response domain. In another preferred embodiment, the target binding domain comprises an immunoglobulin heavy chain fragment, and optionally, further comprises a hinge region. In a particularly preferred embodiment, the heavy chain fragment comprises amino acids, VDKKI (SEQ ID NO: 2) of the $C_H1$ domain and/or part or all of the $C_H2$ and $C_H3$ domains.

As discussed above, antigens that are bound and internalized by CD206 can be presented by both MHC Class I and Class II, thus eliciting both a cellular and humoral immune response. Accordingly, in a preferred embodiment, the chimeric antigen is glycosylated. The immune response domain and/or the target binding domain can be glycosylated. In a particularly preferred embodiment, the chimeric antigen is mannose glycosylated by either high mannose glycosylation or by pauci mannose glycosylation (Jarvis, *Virology* 310:1-7 (2003)).

D. Novel Methods of Utilizing Chimeric Antigens

The invention includes methods of eliciting an immune response comprising administering, to a subject, a composition comprising a chimeric antigen of the invention.

In order to provide efficient presentation of the antigens, the inventors have developed a novel chimeric antigen comprising an immune response domain and a target binding domain, wherein the target binding domain comprises an antibody fragment. While not being limited to a particular theory of the invention, this molecule, by virtue of the antibody fragment binds to specific receptors on the antigen presenting cells, and the viral antigen is processed and presented complexed with Major Histocompatibility Complex (MHC) Class I and Class II. Such processing and antigen presentation by MHC Class I elicits an increased response by cytotoxic T-lymphocytes, resulting in the elimination of any infectious agent associated with the antigen of the immune response domain. In addition, antigen presentation by MHC Class II molecules, elicits a humoral response that also aids in clearance of the antigen from the infected cell and/or from circulation.

The invention also includes methods of breaking tolerance comprising administering a chimeric antigen of the invention to a subject. In the presentation of antigens to elicit a cellular and/or humoral immune response by the use of chimeric antigens, the antigens, which were treated as "self" during a chronic infection, are recognized as "foreign." Accordingly, the host's immune system will mount a CTL response to eliminate infected cells. At the same time, antibodies elicited in response to the chimeric antigen will bind to the infectious agent and remove it from the circulation or block binding of the infectious agent to host cells. Accordingly, the present invention is designed to produce chimeric antigens that can induce a broad immune response in subjects who have chronic infections that are otherwise tolerated by the host immune system. In a preferred embodiment, the chimeric antigen breaks tolerance to an antigen in a subject who is chronically infected with an infectious agent, such as a virus or parasite, or who has a cancer. More preferably, the infectious agent is resident inside a host cell at some point during its life cycle.

In a preferred embodiment, the immunogenicity of the pre-selected antigen unrecognized or tolerated by the host immune system is increased due to the presence of the antibody fragment as well as by the presence of glycosylation introduced in an eukaryotic, e.g. insect, cell expression system. Such a chimeric antigen, due to the presence of the antibody component and glycosylation, will bind to specific receptors present on various immune cell types including dendritic cells, macrophages, B cells and granulocytes.

Yet another aspect of the invention provides methods of activating antigen presenting cells comprising contacting the antigen presenting cells with a chimeric antigen of the invention. The invention also provides methods of enhancing antigen presentation in an antigen presenting cell comprising contacting the antigen presenting cell with a composition comprising a chimeric antigen of the invention. The chimeric antigen can be contacted with the antigen presenting cells, preferably dendritic cells, in vivo or ex vivo. In a preferred embodiment, contacting the chimeric antigen with antigen presenting cells activates the antigen presenting cells and enhances antigen presentation of more than one epitope. This multi-epitopic response can include presentation of one or more epitopes of the immune response domain and/or presentation of one or more epitopes of the target binding domain.

The invention also provides methods of treating an immune-treatable condition comprising administering, to a subject in need thereof, a therapeutically effective amount of a chimeric antigen of the invention. In a preferred embodiment, the immune-treatable condition is an infection or a cancer. The infection can be a viral infection, a parasitic infection or a bacterial infection. Preferably, the infection will have a stage during which the infectious agent is found within a host cell. More preferably, the immune-treatable condition is a chronic viral infection. Most preferably, the immune-treatable condition is a chronic hepatitis B viral (HBV) infection or a chronic hepatitis C viral (HCV) infection. For the treatment of HBV, the immune response domain preferably comprises at least one antigenic portion of a protein selected from the group consisting of a HBV Core protein, a HBV S protein, a HBV S1 protein, a HBV S2 protein, and combinations thereof. For the treatment of HCV, the immune response domain preferably comprises at least one antigenic portion of a protein selected from the group consisting of a HCV Core (1-191) protein, a HCV Core (1-177) protein, a HCV E1 protein, a HCV E2 protein, a HCV E1-E2 protein, a HCV NS3A protein, a HCV NS5A protein, and combinations thereof.

In a preferred embodiment, administration of the chimeric antigen elicits a greater immune response than administration of the immune response domain alone. The amplitude of the immune response can be measured, for example, (i) by the amount of antigen-specific antibody present in the subject; (ii) by the amount of interferon-γ secreted by T cells in response to being exposed to antigen presenting cell loaded with the chimeric antigen or immune response domain alone; or (iii) by the amount of antigen specific $CD8^+$ T cells elicited in response to being exposed to antigen presenting cell loaded with the chimeric antigen or immune response domain alone.

The chimeric antigen can be evaluated for its efficacy in generating an immune response by presenting the chimeric antigen to dendritic cells ex vivo or in vivo. The dendritic cells process and present the chimeric antigen to T-lymphocytes, which are evaluated for proliferation of T cells and for the production of interferon-γ as markers of T cell response. Specifically, in the ex vivo situation, naive dendritic cells are isolated from peripheral blood. Activation of the T cells by the dendritic cells is evaluated by measuring markers, e.g. interferon-γ levels, by a known procedure. See, e.g., Berlyn, et al., *Clin. Immunol* 101(3):276-283 (2001). An increase in the percentage of T cells that secrete interferon-γ by at least 50% predicts efficacy in vivo. In the case of the in vivo situation, the chimeric antigen is directly introduced parenterally in the host where available dendritic and other antigen-processing cells have the capacity to interact with antigens and to process them accordingly.

Additionally, the invention includes methods of vaccinating a subject against an infection comprising administering a chimeric antigen of the present invention to the subject. The subject can be prophylactically or therapeutically vaccinated. Preferably, the infection is a viral infection. The bifunctional nature of the molecule helps to target the antigen to antigen-presenting cells, e.g. dendritic cells, making it a unique approach in the therapy of chronic infectious diseases by specifically targeting the antigen presenting cells with the most effective stoichiometry of antigen to antibody. This is useful to the development of therapeutic vaccines to cure chronic viral infections such as Hepatitis B, Hepatitis C, Human Immunodeficiency Virus, Human Papilloma Virus and Herpes Simplex Virus, obligate intracellular parasites and may also be applicable to all autologous antigens in diseases such as cancer and autoimmune disorders. The administration of these fusion proteins can elicit a broad immune response from the host, including both cellular and humoral responses. Thus, they can be used as therapeutic vaccines to treat subjects that are immune tolerant to an existing infection, in addition to being useful as prophylactic vaccines to immunize subjects at risk for developing a particular infection.

E. Methods of Making Chimeric Antigens

One aspect of the invention provides methods for producing a chimeric antigen comprising (a) providing a microorganism or cell line, preferably a eukaryotic, more preferably, a non-mammalian microorganism or cell line that comprises a polynucleotide encoding a chimeric antigen; and (b) culturing said microorganism or cell line under conditions whereby the chimeric antigen is expressed. Preferably, the microorganism or cell line is a yeast, a plant cell line or an insect cell line. More preferably, the cell line is an insect cell line selected from the group consisting of Sf9, Sf21, Drosophila S2, and High Five™.

One embodiment of the present invention uses established recombinant DNA technology for producing the fusion proteins of selected antigen(s) and the target binding domain that are necessary in the practice of the invention. Fusion protein constructs are generated at the DNA level incorporating specific restriction enzyme sites, which are exploited in incorporating the desired DNA fragment into expression vectors, and used to express the desired fusion proteins in a heterologous expression system. As used herein, the term "vector" denotes plasmids that are capable of carrying the DNA, which encode the desired protein(s). Preferred plasmid vectors for use in the present invention include, but are not limited to, pFastBac HTa and the corresponding recombinant "bacmids" generated in DH10Bac™ *E. coli* (Invitrogen).

A gene encoding a target binding domain can be obtained from any antibody producing cell, for example a hybridoma producing a monoclonal antibody, via polymerase chain reaction (PCR). To facilitate later cloning steps, it is preferable to design the oligonucleotide primers to add unique restriction enzyme recognition sites. Similarly, the antigenic portions of the immune response domain can be obtained from any cell or virus RNA or DNA containing a gene encoding an antigenic portion of the desired target. Preferably, PCR is used to obtain DNA encoding the antigenic portions of the immune response domain and the PCR primers are designed to add unique restriction enzyme recognition sites to facilitate cloning. However, any recombinant DNA method may be used to obtain the DNA encoding the antigenic portions of the immune response domain. The polynucleotides encoding the target binding domain and immune response domain can then be combined in a single construct using standard cloning techniques. Alternatively, the separate domains can be cloned with DNA encoding linkers, such as leucine zippers, streptavidin or biotinylation signals.

Preferably, a baculovirus system is used to express the chimeric antigen of the invention not only because large amounts of heterologous proteins are produced, but also because post-translational modifications, such as phosphorylation and glycosylation, of eukaryotic proteins occur within the infected insect cell. Since cloning directly in insect cells can be difficult, it is preferable to generate the polynucleotide encoding the chimeric antigen in a bacterial system and to transfer the final construct into a baculovirus/insect cell expression system. Transfer systems, e.g., the Bac-To-Bac™ system (Invitrogen), are known to those of skill in the art. The Bac-to-Bac™ system utilizes site-specific transposition with the bacterial transposon Tn7 to transfer the gene of interest into a E. coli-insect cell shuttle vector (bacmid). The resulting recombinant bacmids are transfected into insect cells to generate baculoviruses that express recombinant proteins.

In order to produce baculoviruses, the bacmid is transfected into insect cells, such as Sf9 cells. Following transfection, the cells are incubated for a period of time sufficient to expand the baculoviral population. The medium containing baculovirus is collected and stored at 4° C. in the dark. The transfection can be verified by checking for production of baculoviral DNA by subjecting the viral culture to PCR utilizing primers specific for the desired DNA insert. The expression of the heterologous protein in the cells can be verified by any method known in the art, e.g. SDS polyacrylamide gel electrophoresis (SDS-PAGE) or Western blotting.

Recombinant bacmids of standardized multiplicity of infection (MOI) are used to infect insect cells. Cells are seeded at a density of approximately $3 \times 10^5$ cells/mL and incubated in suspension culture at 27.5° C. with shaking until the cell density reached approximately $2-3 \times 10^6$ cells/mL. Standardized amounts of the respective recombinant baculovirus are then added to the cells. The incubation temperature is 27.5° C. and the appropriate infection period is standardized for individual protein expression. The cells are harvested by centrifugation and used for the purification of the recombinant proteins. Unused portions of cells can be snap frozen in liquid nitrogen and stored at −70° C.

Chimeric antigens, preferably, are purified under denaturing conditions. Cells expressing chimeric antigens are lysed in a denaturing buffer, e.g., a buffer containing 6 M guanidinium-HCl. Lysis can be increased by mechanical means, such as sonication. The lysate is centrifuged to remove unbroken cells and cell debris. The supernatant is then loaded on to a Ni-NTA Super Flow (Qiagen) bead column pre-equilibrated with lysis buffer. Following loading, the column is washed with a buffered denaturing solution, preferably containing 6 M guanidinium-HCl at approximately pH 8. At this point the denaturant can be exchanged to, e.g., 8 M urea in a buffered solution. The lysis, loading and wash buffers preferably contain a low concentration, e.g., 1-40 mM imidazole. After buffer exchange, the column should be washed with buffer until the $OD_{280}$ drops to, for example, <0.1. The bound protein can be eluted with a buffer containing 8 M urea, and 250 mM imidazole, pH 8 (Elution Buffer). The fractions containing the protein are pooled and dialyzed at 4° C. against multiple changes of low (e.g., 100 mM) salt denaturing dialysis buffer, preferably containing 8 M urea. The dialyzed protein is then loaded onto an ion exchange column, such as DEAE (diethylaminoethyl). In a preferred embodiment, dithiothreitol (DTT) or other reducing agent is added to the protein prior to loading onto the ion exchange column. The chimeric antigen will pass through a DEAE column. Therefore, the DEAE flowthrough is collected and dialyzed in a stepwise manner against buffers containing decreasing concentrations of denaturant. In an exemplary method, the protein is then dialyzed against buffered 4 M urea for at least 12 hours, then against buffered 2 M urea for at least 12 hours, then against buffered 1 M urea for at least 12 hours, then against buffered 0.5 M urea for at least 12 hours and finally dialyzed against buffer containing no denaturant for at least 12 hours, preferably followed by two additional periods of 12 hours dialysis against fresh buffer containing no denaturant. Purified, refolded proteins can be concentrated and characterized using standard biochemical techniques including, e.g., SDS gel electrophoresis, isoelectric focusing, or western blot analysis using antibodies against different domains of the expressed protein.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook et al., *Molecular Cloning: A Laboratory Manual*, 2nd Ed., New York: Cold Spring Harbor Press, 1989; and Ausubel et al., *Current Protocols in Molecular Biology*, Wiley Interscience Publishers, (©1995, as Supplemented Apr. 2004, Supplement 66).

F. Novel Polynucleotides

Another aspect of the invention provides polynucleotides encoding a chimeric antigen comprising a first polynucleotide portion encoding an immune response domain and a second polynucleotide portion encoding a target binding domain. The first and second polynucleotide portions may be located on the same or different nucleotide chains.

The invention provides polynucleotides corresponding or complementary to genes encoding chimeric antigens, mRNAs, and/or coding sequences, preferably in isolated form, including polynucleotides encoding chimeric antigen variant proteins; DNA, RNA, DNA/RNA hybrids, and related molecules, polynucleotides or oligonucleotides complementary or having at least a 90% homology to the genes encoding a chimeric antigen or mRNA sequences or parts thereof, and polynucleotides or oligonucleotides that hybridize to the genes encoding a chimeric antigen, mRNAs, or to chimeric antigen-encoding polynucleotides.

Additionally, the invention includes analogs of the genes encoding a chimeric antigen specifically disclosed herein. Analogs include, e.g., mutants, that retain the ability to elicit an immune response, and preferably have a homology of at least 80%, more preferably 90%, and most preferably 95% to any of polynucleotides encoding a chimeric antigen, as specifically described by SEQ ID NOs: 26, 28, 30, 32, 34, 36, 38, 40, 42, 44, 46, and 44. Typically, such analogs differ by only 1 to 15 codon changes. Examples include polypeptides with minor amino acid variations from the natural amino acid sequence of a viral antigen or of an antibody fragment, in particular, conservative amino acid replacements. Conservative replacements are those that take place within a family of amino acids that are related in their side chains. Genetically-encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar-glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on biological activity. Polypeptide molecules having substantially the same amino acid sequence as any of the polypeptides disclosed in any one of SEQ ID NOs: 27, 29, 31, 33, 35, 37, 39, 41, 43, 45, 47 and 49 but possessing minor amino acid substitutions that do not substantially affect the ability of the chimeric antigens to elicit an immune response, are within the definition of a chimeric antigen having the sequence as set forth in SEQ ID NOs: 27, 29, 31, 33, 35, 37, 39, 41, 43, 45, 47 and 49, respectively. Derivatives include aggregative conjugates with other chimeric antigen molecules and covalent conjugates with unrelated chemical moieties. Covalent derivatives are prepared by linkage of functionalities to groups that are found in chimeric antigen amino acid chains or at the N- or C-terminal residues by means known in the art.

Amino acid abbreviations are provided in Table 1.

TABLE 1

Amino Acid Abbreviations

| Alanine | Ala | A |
|---|---|---|
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Conservative amino acid substitutions can be made in a protein without altering either the conformation or the function of the protein. Proteins of the invention can comprise 1 to 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g. *Biochemistry* 4$^{th}$ *Ed.*, Lubert Stryer ed. (W. H. Freeman and Co.), pages 18-23; Henikoff and Henikoff, *Proc Nat'l Acad Sci USA* 89:10915-10919 (1992); Lei et al., *J Biol Chem* 270(20):11882-6 (1995)).

The inventions also provides polynucleotides that hybridize, preferably under stringent conditions, to a polynucleotide encoding a chimeric antigen, as specifically described by SEQ ID NOs: 26, 28, 30, 32, 34, 36, 38, 40, 42, 44, 46, and 44. Stringency of hybridization reactions is readily determinable by one of ordinary skill in the art and generally is an empirical calculation dependent upon probe length, washing temperature, and salt concentration. In general longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see, e.g., Ausubel et al., supra, at pages 2.9.1-2.10.8 and 4.9.1-4.9.13.

"Stringent conditions" or "high stringency conditions", as defined herein, are identified by, but not limited to, those that (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" are described by, but not limited to, those in Sambrook et al., supra, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Embodiments of a chimeric antigen-encoding polynucleotide include: a polynucleotide encoding a chimeric antigen having a sequence selected from any of SEQ ID NOs: 27, 29, 31, 33, 35, 37, 39, 41, 43, 45 47 and 49, or a nucleotide sequence of chimeric antigen selected from any of SEQ ID NOs: 26, 28, 30, 32, 34, 36, 38, 40, 42, 44, 46 and 48, wherein T, optionally, can be U; For example, embodiments of chimeric antigen nucleotides comprise, without limitation:

(a) a polynucleotide comprising or consisting of a sequence as described by SEQ ID NOs.: nucleotides 1 to 1326 of SEQ ID NO: 26, nucleotides 1 to 2004 of SEQ ID NO: 28, nucleotides 1 to 1350 of SEQ ID NO: 30, nucleotides 1 to 1293 of SEQ ID NO: 32, nucleotides 1 to 1794 of SEQ ID NO: 34, nucleotides 1 to 1581 of SEQ ID NO: 36, nucleotides 1 to 1389 of SEQ ID NO: 38, nucleotides 1 to 1347 of SEQ ID NO: 40, nucleotides 1 to 2157 of SEQ ID NO: 42, nucleotides 1 to 1395 of SEQ ID NO: 44, nucleotides 1 to 1905 of SEQ ID NO: 46, or nucleotides 1 to 2484 of SEQ ID NO: 48, wherein T can also be U;

(b) a polynucleotide whose sequence is at least 80% homologous to a sequence as described by SEQ ID NOs: 26, 28, 30, 32, 34, 36, 38, 40, 42, 44, 46 or 48;

(c) a polynucleotide that encodes a chimeric antigen whose sequence encoded by a DNA contained in one of the plasmids designated pFastBacHTa HBV S1/S2-TBD, pFastBacHTa HBV core-TBD, pFastBacHTa HCV core(1-177)-TBD, pFastBacHTa HCV NS5A-TBD, and pFastBacHTa HCV E2-TBD deposited with the International Depository Authority of Canada (Bureau of Microbiology at Health Canada) as Accession Nos. 080504-03, 080504-04, 080504-05, 080504-02 and 080504-01 respectively;

(d) a polynucleotide that encodes a chimeric antigen whose sequence is amino acids 1 to 442 of SEQ ID NO: 27, amino acids 1 to 668 of SEQ ID NO: 29, amino acids 1 to 450 of SEQ ID NO: 31, amino acids 1 to 431 of SEQ ID NO: 33, amino acids 1 to 598 of SEQ ID NO: 35, amino acids 1 to 527 of SEQ ID NO: 37, amino acids 1 to 463 of SEQ ID NO: 39, amino acids 1 to 449 of SEQ ID NO: 41, amino acids 1 to 719 of SEQ ID NO: 43, amino acids 1 to 465 of SEQ ID NO: 45, amino acids 1 to 635 of SEQ ID NO: 47, or amino acids 1 to 828 of SEQ ID NO: 49;

(e) a polynucleotide that encodes a chimeric antigen-related protein that is at least 90% identical to an entire amino acid sequence described by amino acids 1 to 442 of SEQ ID NO: 27, amino acids 1 to 668 of SEQ ID NO: 29, amino acids 1 to 450 of SEQ ID NO: 31, amino acids 1 to 431 of SEQ ID NO: 33, amino acids 1 to 598 of SEQ ID NO: 35, amino acids 1 to 527 of SEQ ID NO: 37, amino acids 1 to 463 of SEQ ID NO: 39, amino acids 1 to 449 of SEQ ID NO: 41, amino acids 1 to 719 of SEQ ID NO: 43, amino acids 1 to 465 of SEQ ID NO: 45, amino acids 1 to 635 of SEQ ID NO: 47, or amino acids 1 to 828 of SEQ ID NO: 49;

(f) a polynucleotide that is fully complementary to a polynucleotide of any one of (a)-(d); and (g) a polynucleotide that selectively hybridizes under stringent conditions to a polynucleotide of (a)-(f).

The invention also provides recombinant DNA or RNA molecules containing a chimeric antigen polynucleotide, an analog or homologue thereof, including but not limited to phages, plasmids, phagemids, cosmids, YACs (yeast artificial chromosomes), BACs (bacterial artificial chromosomes), as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a chimeric antigen polynucleotide, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as a Sf9, Sf21, Drosophila S2 or High Five™ cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of chimeric antigen or a fragment, analog or homolog thereof can be used to generate chimeric antigen thereof using any number of host-vector systems routinely used and widely known in the art.

A wide range of host-vector systems suitable for the expression of chimeric antigens thereof are available, see for example, Sambrook et al., 1989, supra; Ausubel, supra, at pages 1.0.1-1.16.16, 9.01-9.17.3, and 13.4.1-13.6.5). Preferred vectors for insect cell expression include but are not limited to pFastBac HTa (Invitrogen). Using such expression vectors, chimeric antigens can be expressed in several insect cell lines, including for example Sf9, Sf21, Drosophila S2 and High Five. Alternatively, preferred yeast expression systems include *Saccharomyces cerevisiae, Schizosaccharomyces pombe, Pichia pastoris,* and *Pichia august.* The host-vector systems of the invention are useful for the production of a chimeric antigen.

A chimeric antigen or an analog or homolog thereof can be produced by cells transfected with a construct encoding a chimeric antigen. For example, Sf9 cells can be transfected with an expression plasmid encoding a chimeric antigen or analog or homolog thereof, the chimeric antigen is expressed in the Sf9 cells, and the chimeric antigen is isolated using standard purification methods. Various other expression systems well known in the art can also be employed. Expression constructs encoding a leader peptide joined in frame to the chimeric antigen coding sequence can be used for the generation of a secreted form of chimeric antigen.

As discussed herein, redundancy in the genetic code permits variation in chimeric antigen gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Condon preferences for a specific species are calculated, for example, by utilizing codon usage tables available on the INTERNET.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.,* 9:5073-5080 (1989). Skilled artisans understand that the general rule that eukaryotic ribosomes initiate translation exclusively at the 5' proximal AUG codon is abrogated only under rare conditions (see, e.g., Kozak *Proc Nat'l Acad Sci USA* 92(7): 2662-2666 (1995) and Kozak *Nucl Acids Res* 15(20): 8125-8148 (1987)).

G. Pharmaceutical Compositions of the Invention

One aspect of the invention relates to pharmaceutical compositions comprising a pharmaceutically acceptable excipient and a chimeric antigen comprising an immune response domain and a target binding domain, wherein the target binding domain comprises an antibody fragment. In therapeutic applications, the pharmaceutical compositions can be administered to a subject in an amount sufficient to elicit an effective B cell, cytotoxic T lymphocyte (CTL) and/or helper T lymphocyte (Th) response to the antigen and to block infection or to cure or at least partially arrest or slow symptoms and/or complications or a disease or disorder. Amounts effective for this use will depend on, e.g., the particular composition administered, the manner of administration, the stage and severity of the disease being treated, the weight and general state of health of the subject, and the judgment of the prescribing physician.

The dosage for an initial therapeutic immunization (with chimeric antigen) generally occurs in a unit dosage range where the lower value is about 1, 5, 50, 500, or 1,000 ng and the higher value is about 10,000; 20,000; 30,000; or 50,000 µg. Dosage values for a human typically range from about 500 ng to about 50,000 µg per 70 kilogram subject. Boosting dosages of between about 1.0 ng to about 50,000 µg of chimeric antigen pursuant to a boosting regimen over weeks to months may be administered depending upon the subject's response and condition. Administration should continue until at least clinical symptoms or laboratory tests indicate that the condition has been prevented, arrested, slowed or eliminated and for a period thereafter. The dosages, routes of administration, and dose schedules are adjusted in accordance with methodologies known in the art.

A human unit dose form of a chimeric antigen is typically included in a pharmaceutical composition that comprises a human unit dose of an acceptable carrier, in one embodiment an aqueous carrier, and is administered in a volume/quantity that is known by those of skill in the art to be useful for administration of such polypeptides to humans (see, e.g., *Remington: The Science and Practice of Pharmacy*, 20$^{th}$ Edition, A. Gennaro, Editor, Lippincott Williams & Wilkins, Baltimore, Md., 2000). As appreciated by those of skill in the art, various factors can influence the ideal dose in a particular case. Such factors include, for example, half life of the chimeric antigen, the binding affinity of the chimeric antigen, the immunogenicity of the composition, the desired steady-state concentration level, route of administration, frequency of treatment, and the influence of other agents used in combination with the treatment method of the invention, as well as the health status of a particular subject.

In certain embodiments, the compositions of the present invention are employed in serious disease states, that is, life-threatening or potentially life-threatening situations. In such cases, as a result of the relative nontoxic nature of the chimeric antigen in preferred compositions of the invention, it is possible and may be felt desirable by the treating physician to administer substantial excesses of these chimeric antigens relative to these stated dosage amounts.

The concentration of chimeric antigen of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The pharmaceutical compositions can be delivered via any route known in the art, such as parenterally, intrathecally, intravascularly, intravenously, intramuscularly, transdermally, intradermally, subcutaneously, intranasally, topically, orally, rectally, vaginally, pulmonarily or intraperitoneally. Preferably, the composition is delivered by parenteral routes, such as subcutaneous or intradermal administration.

The pharmaceutical compositions can be prepared by mixing the desired chimeric antigens with an appropriate vehicle suitable for the intended route of administration. In making the pharmaceutical compositions of this invention, the chimeric antigen is usually mixed with an excipient, diluted by an excipient or enclosed within a carrier that can be in the form of a capsule, sachet, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the chimeric antigen, soft and hard gelatin capsules, suppositories, sterile injectable solutions, and sterile packaged powders.

Some examples of suitable excipients include, but are not limited to, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the chimeric antigen after administration to the subject by employing procedures known in the art. See, e.g., Remington, supra, at pages 903-92 and pages 1015-1050.

For preparing solid compositions such as tablets, the chimeric antigen is mixed with a pharmaceutical excipient to form a solid preformulation composition containing a homogeneous mixture of a chimeric antigen of the present invention. When referring to these preformulation compositions as homogeneous, it is meant that the chimeric antigen is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

In preparing a composition for parenteral administration strict attention must be paid to tonicity adjustment to reduce irritation. A reconstitutable composition is a sterile solid packaged in a dry form. A reconstitutable composition is preferred because it is more stable when stored as a dry solid rather than in a solution ready for immediate administration. The dry solid is usually packaged in a sterile container with a butyl rubber closure to ensure the solid is kept at an optimal moisture range. A reconstitutable dry solid is formed by dry fill, spray drying, or freeze-drying methods. Descriptions of these methods may be found, e.g., in Remington, supra, at pages 681-685 and 802-803.

Compositions for parenteral injection are generally dilute, and the component present in the higher proportion is the vehicle. The vehicle normally has no therapeutic activity and is nontoxic, but presents the chimeric antigen to the body tissues in a form appropriate for absorption. Absorption normally will occur most rapidly and completely when the chimeric antigen is presented as an aqueous solution. However, modification of the vehicle with water-miscible liquids or substitution with water-immiscible liquids can affect the rate of absorption. Preferably, the vehicle of greatest value for this composition is isotonic saline. In preparing the compositions that are suitable for injection, one can use aqueous vehicles, water-miscible vehicles, and nonaqueous vehicles Additional substances may be included in the injectable compositions of this invention to improve or safeguard the quality of the composition. Thus, an added substance may affect solubility, provide for subject comfort, enhance the chemical stability, or protect the preparation against the growth of microorganisms. Thus, the composition may include an appropriate solubilizer, substances to act as anti-oxidants, and substances that act as a preservative to prevent the growth of microorganisms. These substances will be present in an amount that is appropriate for their function, but will not adversely affect the action of the composition. Examples of appropriate antimicrobial agents include thimerosal, benzethonium chloride, benzalkonium chloride, phenol, methyl p-hydroxybenzoate, and propyl p-hyrodxybenzoate. Appropriate antioxidants may be found in Remington, supra, at p. 1015-1017.

In certain embodiments, liposomes, nanocapsules, microparticles, lipid particles, vesicles, and the like, are used for the administration of the chimeric antigens of the present invention. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

Compositions administered via liposomes may also serve: 1) to target the chimeric antigen to a particular tissue, such as lymphoid tissue; 2) to target selectively to antigen presenting cells; or, 3) to increase the half-life of the peptide composition. Liposomes include emulsions, foams, micelles, insoluble monolayers, liquid crystals, phospholipid dispersions, lamellar layers and the like. In these preparations, the chimeric antigen to be delivered is incorporated as part of a liposome, alone or in conjunction with a molecule that binds to a receptor prevalent among lymphoid cells, such as monoclonal antibodies that bind to the CD45 antigen, or with other therapeutic or immunogenic compositions. Thus, liposomes either filled or decorated with a desired chimeric antigen of the invention can be directed to the site of lymphoid cells, where the liposomes then deliver the chimeric antigens. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467-508 (1980), and U.S. Pat. Nos. 4,235,871, 4,501,728, 4,837,028, and 5,019,369. A liposome suspension containing a chimeric antigen may be administered intravenously, locally, topically, etc. in a dose which varies according to, inter alia, the manner of administration, the chimeric antigen being delivered, and the stage of the disease being treated.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions can be administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Another formulation employed in the methods of the present invention employs transdermal delivery devices ("patches"). Such transdermal patches may be used to provide continuous or discontinuous infusion of the chimeric antigen of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Additionally, it may be advantageous to include at least one antiviral therapeutic or chemotherapeutic in addition to the chimeric antigen and pharmaceutical excipient. Antiviral therapeutics include, but are not limited to, peptidomimetics (such as amprenavir, indinavir, lopinavir, nelfinavir, ritonavir, and saquinavir), polynucleotides (such as ampligen and fomivirsen), purine/pyrimidinones (such as abacavir, acyclovir, adefovir, cidofovir, cytarabine, didanosine, dideoxyadenosine, dipivoxil, edoxudine, emtricitabine, entecovir, famciclovir, ganciclovir, idoxuridine, inosine pranobex, lamivudine, MADU, penciclovir, sorivudine, stavudine, tenofovir, trifluridine, valacyclovir, valganciclovir, vidarabine, zalcitabine, and zidovudine), sialic acid analogs (such as oseltamivir and zanamivir), acemannan, acetylleucine monoethanolamine, amantadine, amidinomycin, ateviridine, capravirine, delavirdine, n-docosanol, efavirenz, foscamet sodium, interferon-α, interferon-β, interferon-γ, kethoxal, lysozyme, methisazone, moroxydine, nevirapine, pentafuside, pleconaril, podophyllotoxin, ribavirin, rimantidine, stallimycin, statolon, termacamra, and traomantadine. Other appropriate antiviral agents are discussed in Remington: supra, at Chapter 87: Anti-Infectives, pp. 1507-1561, particularly pp. 1555-1560. Preferred antiviral therapeutics for inclusion in the pharmaceutical compositions of the present invention include adefovir, dipivoxil, entecovir, lamivudine and ribavirin.

In some embodiments it may be desirable to include in the pharmaceutical compositions of the invention at least one component which primes B-lymphocytes or T lymphocytes. Lipids have been identified as agents capable of priming CTL in vivo. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561 (1989)). Chimeric antigens of the invention can be coupled to $P_3CSS$, for example, and the lipopeptide administered to an individual to specifically prime an immune response to the target antigen.

While the compositions of the present invention should not require the use of adjuvants, adjuvant can be used. Various adjuvants may be used to increase the immunological response, depending on the host species, and including but not limited to Freund's (complete and incomplete), mineral gels such as aluminum hydroxide, surface active substances such as lysolecithin, detergents, pluronic polyols, polyanions, peptides, oil emulsions, keyhole limpet hemocyanins, dinitrophenol, immunostimulatory polynucleotide sequences, and potentially useful human adjuvants such as BCG (bacille Calmette-Guerin) and *Corynebacterium parvum*. Additional adjuvants are also well known in the art.

H. Article of Manufacture

Another aspect of this invention provides an article of manufacture that comprises a container holding a composition, comprising a chimeric antigen, that is suitable for injection or reconstitution for injection in combination with printed labeling instructions providing a discussion of how to administer the composition parenterally, e.g. subcutaneously, intramuscularly, intradermally, nasally or intravascularly. The composition will be contained in any suitable container that will not significantly interact with the composition and will be labeled with the appropriate labeling that indicates it will be for parenteral use. Associated with the container will be the labeling instructions consistent with the method of treatment as described hereinbefore. The container that holds the composition of this invention may be a container having a liquid composition suitable for injection that has an appropriate needle for injection and a syringe so that the patient, doctor, nurse, or other practitioner can administer the chimeric antigen. Alternatively, the composition may be a dry or concentrated composition containing a soluble version of the chimeric antigen, to be combined or diluted with an aqueous or nonaqueous vehicle to dissolve or suspend the composition. Alternatively, the container may have a suspension in a liquid or may be an insoluble version of the salt for combination with a vehicle in which the insoluble version will be suspended. Appropriate containers are discussed in Remington, supra, pages 788-789, 805, 850-851 and 1005-1014.

The kit of the invention will typically comprise the container described above and one or more other containers comprising materials desirable from a commercial and user standpoint, including buffers, diluents, filters, needles, syringes, and package inserts with instructions for use. A label can be present on the container to indicate that the composition is used for a specific therapy or non-therapeutic application, and can also indicate directions for either in vivo or ex vivo use, such as those described above. Directions and or other information can also be included on an insert which is included with the kit.

V. EXAMPLES

The following non-limiting examples provide further illustration of the invention.

A. Example 1

Construction of TBD Expression Vector

Mouse IgG1 DNA sequences encoding amino acids of a portion of $C_H1$-Hinge-$C_H2$-$C_H3$ region was generated from mRNA isolated from the hybridoma (2C12), which produces mAb against HBV surface antigen (sAg). Total mRNA was isolated using Trizol® reagent (Gibco BRL cat. No. 15596-026) and the cDNA of the target binding domain (TBD; mouse immunoglobulins fragment) was generated by RT-PCR using Superscript First-strand Synthesis (Invitrogen Cat. No. 11904-018). The PCR primers contained linker sequences encoding the linker peptide-SRPQGGGS-(SEQ ID NO: 1) at the 5' terminus, a unique Not I site at the 5' and a unique Hind III restriction site at the 3' end. The resulting cDNA contains (5' Not I)-linker sequence-$C_H1$(VDKKI) (SEQ ID NO: 2).-Hinge Region-$C_H2$-$C_H3$-(3' Hind III). Following digestion with the respective enzymes, the fragment is ligated with pFastBac HTa expression vector plasmid (Invitrogen) using the same restriction enzyme sites. The 5' primer used for PCR amplification was (Sense) 5' TGTCATTCT-GCGGCCGCAAGGCGGCGGATCCGTGGA-CAAGAAAATTGTGCCC AGG (SEQ ID NO: 3) and the 3' primer was (antisense) 5' ACGAATCAAGCTTTGCAGC-CCAGGAGAGTGGGAGAG (SEQ ID NO: 4), which contained the Not I and Hind III sites, respectively. The following is the protocol used for directional cloning. The generated fragment was digested with the respective enzymes, purified on agarose gel and cloned into the vector plasmid. The DNA sequence and the correctness of the ORF were verified by standard sequencing methods.

Following the cloning of the DNA encoding the target binding domain into the pFastBac HTa donor plasmid, the recombinant proteins was expressed using the Bac-to-Bac™ baculovirus expression system (Invitrogen). The cloned gene was transferred into a baculovirus shuttle vector via site-specific transposition in a strain of *E. coli*, DH10Bac. The DH10Bac cells contain the shuttle vector, which confers kanamycin resistance and a helper plasmid, which encodes the transposase and confers resistance to tetracycline. A 100 µl aliquot of competent DH10Bac cells was thawed on ice, the pFastBac HTa based plasmids were added and the mixture incubated on ice for 30 minutes. The mixture was heat shocked for 45 seconds at 42° C. and then chilled on ice for 2 minutes. The mixture was then added to 900 µL of LB media and incubated for 4 hours at 37° C. The transformed cells were serially diluted with LB to $10^{-1}$ and $10^{-2}$ and 100 µl of each dilution was plated on LB agar plates supplemented with 50 µg/ml kanamycin, 7 µg/ml gentamicin, 10 µg/ml tetracycline, 100 µg/ml X-gal, and 40 µg/ml IPTG and incubated for at least 36 hours at 37° C. The gentamicin resistance was conferred by the pFastBac HTa and the X-gal and IPTG (isopropylthio-β-D-galactoside) were used to differentiate between white colonies (recombinant plasmids) and blue colonies (non-recombinant). The white colonies were picked and inoculated into 2 ml of LB supplemented with 50 µg/ml kanamycin, 7 µg/ml gentamicin and 10 µg/ml tetracycline and incubated overnight at 37° C., with shaking. A sterile loop was used to sample a small amount of the overnight culture and the sample was streaked onto a fresh LB agar plate supplemented with 50 µg/ml kanamycin, 7 µg/ml gentamicin, 10 µg/ml tetracycline, 100 µg/ml X-gal, and 40 µg/ml IPTG and incubated for at least 36 hours at 37° C. to confirm a white phenotype. Recombinant bacmids were isolated by standard protocols (Sambrook, supra), the DNA sample was dissolved in 40 µl of TE (10 mM Tris-HCL pH 8, 1 mM EDTA) and used for transfections.

In order to produce baculoviruses, the bacmid was transfected into Sf9 insect cells. Sf9 cells ($9 \times 10^5$) were seeded into each well of a 6-well cell culture dish (35 mm wells) in 2 ml of ESF 921 (Expression Systems) and allowed to attach for at least 1 hour at 27° C. Transfections were carried out using Cellfection® Reagent (Invitrogen, Cat. No. 10362-010) as per the protocols provided by the supplier of the Sf9 cells. Following transfection, the cells were incubated at 27° C. for 72 hours. The medium containing baculovirus was collected and stored at 4° C. in the dark.

The efficiency of the transfection was verified by checking for production of baculoviral DNA. The isolated baculovirus DNA was subjected to PCR to screen for the inserted gene encoding the TBD. The primers used were (sense) 5' TATTC-CGGATTATTCATACCG (SEQ ID NO: 5) and 3' (antisense) 5' CTCTACAAATGTGGTATGGC (SEQ ID NO: 6). Amplified products were run on an agarose gel (0.8%). The expression of the heterologous protein in the cells was verified by SDS polyacrylamide gel electrophoresis (SDS-PAGE) and Western blots using the 6×His tag monoclonal antibody (Clonetech) as the probe.

Once production of baculovirus and the expression of protein were confirmed, the virus production was amplified to produce a concentrated stock of the baculovirus that carry the gene encoding the target binding domain. It is standard practice in the art to amplify the baculovirus at least two times, and in all protocols described herein this standard practice was adhered to. After the second round of amplification, the concentration of the generated baculovirus was quantified using a plaque assay according to the protocols described by the manufacturer of the kit (Invitrogen). The most appropriate concentration of the virus to infect High Five cells and the optimum time point for the production of the desired protein was established as well. Generally, for the expression of the TBD an MOI of 1 and a time period of 48 hours was used.

B. Example 2

Construction of Chimeric Antigen Expression Vectors

The DNA encoding the desired viral antigen was generated from the template using PCR methodology using the 5' sense and 3' anti-sense primers indicated in Table 2. The 5' end of the resulting amplified fragment contained the unique restriction site "5' enzy," and the 3' end contained the unique restriction site "3' enzy," each of which was used for ligations.

TABLE 2

Construction of Chimeric Antigen Vectors

| Viral antigen | Sense primer | Anti-sense primer | Template | 5' enzy | 3' enzy |
|---|---|---|---|---|---|
| HBV S1/S2 | SEQ ID NO: 7 | SEQ ID NO: 8 | pRSETB HBV S1/S2 | Bam HI | Not I |
| HBV S1/S2/S | SEQ ID NO: 9 | SEQ ID NO: 10 | pAlt HBV 991 | Nco I | Not I |
| HBV Core | SEQ ID NO: 11 | SEQ ID NO: 12 | pAlt HBV 991 | Nco I | Not I |
| DHBV PreS/S | SEQ ID NO: 5 | SEQ ID NO: 13 | pFastBac Hta PreS/S | Eco RI | Not I |
| DHBV PreS | SEQ ID NO: 5 | SEQ ID NO: 14 | pFastBac HTa PreS/S | Eco RI | Not I |
| DHBV Core | SEQ ID NO: 15 | SEQ ID NO: 16 | pRSETB DHBV Core | Nco I | Not I |
| HCV Core (1-191) | SEQ ID NO: 17 | SEQ ID NO: 18 | pCV-H77c | Eco RI | Spe I |
| HCV Core (1-177) | SEQ ID NO: 17 | SEQ ID NO: 19 | pCV-H77c | Eco RI | Spe I |
| HCV NS5A | SEQ ID NO: 20 | SEQ ID NO: 21 | pCV-H77c | Eco RI | Spe I |
| HCV E1 | SEQ ID NO: 22 | SEQ ID NO: 23 | pCV-H77c | Eco RI | Spe I |
| HCV E2 | SEQ ID NO: 24 | SEQ ID NO: 25 | pCV-H77c | Eco RI | Spe I |
| HCV E1/E2 | SEQ ID NO: 22 | SEQ ID NO: 25 | pCV-H77c | Eco RI | Spe I |

Amplified DNA was digested with appropriate 5' and 3' restriction enzymes and ligated with a pFastBac HTa expression vector to generate the expression plasmid for the viral antigen alone. The same fragment of DNA was also ligated with the plasmid pFastBac HTa-TBD, described in Example 1, following digestion with the respective enzymes to produce the expression plasmid for the viral antigen fused to the target binding domain. The resulting plasmid was used to produce recombinant baculovirus, as described in Example 1, for subsequent use in expression of the chimeric antigen. The DNA and amino acid sequences of the chimeric antigens are provided in Table 3.

TABLE 3

Chimeric Antigen Sequences

| Construct | DNA sequence | Expressed Protein |
|---|---|---|
| HBV S1/S2-TBD | SEQ ID NO: 26 | SEQ ID NO: 27 |
| HBV S1/S2/S-TBD | SEQ ID NO: 28 | SEQ ID NO: 29 |
| HBV Core-TBD | SEQ ID NO: 30 | SEQ ID NO: 31 |
| DHBV PreS-TBD | SEQ ID NO: 32 | SEQ ID NO: 33 |
| DHBV PreS/S-TBD | SEQ ID NO: 34 | SEQ ID NO: 35 |
| DHBV Core-TBD | SEQ ID NO: 36 | SEQ ID NO: 37 |
| HCV Core(1-191)-TBD | SEQ ID NO: 38 | SEQ ID NO: 39 |
| HCV Core(1-177)-TBD | SEQ ID NO: 40 | SEQ ID NO: 41 |
| HCV NS5A-TBD | SEQ ID NO: 42 | SEQ ID NO: 43 |
| HCV E1-TBD | SEQ ID NO: 44 | SEQ ID NO: 45 |
| HCV E2-TBD | SEQ ID NO: 46 | SEQ ID NO: 47 |
| HCV E1/E2-TBD | SEQ ID NO: 48 | SEQ ID NO: 49 |

C. Example 3

Expression and Purification of TBD, Viral Antigens and Chimeric Antigens

Recombinant bacmids of standardized multiplicity of infection (MOI) were used to infect High Five™ insect cells. For suspension cultures, cells were seeded at a density of $3\times10^5$ cells/mL and incubated at 27.5° C. with shaking at 138 rpm until the cell density reached $2\text{-}3\times10^6$ cells/mL. Standardized amounts of the respective recombinant baculovirus was added to the cells. The incubation temperature was 27.5° C. and the appropriate infection period was standardized for individual protein expression. The cells were harvested by centrifugation at 2,500 rpm for 10 minutes at 4° C. and used for the purification of the recombinant proteins. Unused portions of cells were snap frozen in liquid nitrogen and stored at −70° C.

Recombinant proteins were purified under denaturing conditions. The cells were lysed in a buffer containing 6 M Guanidinium-HCl in 100 mM $NaH_2PO_4$, 10 mM Tris, 300 mM NaCl, 10 mM Imidazole, pH 8.0 (lysis buffer). The suspension was sonicated on ice with 5 pulses of 1 minute per pulse at a power setting of 60 watts, and was mixed at room temperature for 1 hour. The lysate was centrifuged at 10,000×g for 10 min to remove unbroken cells and cell debris. The supernatant was loaded on to a Ni-NTA agarose (Qiagen) bead column (1×5 cm/100 mL cell lysate), pre-equilibrated with lysis buffer. Following loading, the column was washed with 20 column volumes of 6 M guanidinium-HCl in 100 mM $NaH_2PO_4$, 10 mM Tris, 300 mM NaCl, 40 mM Imidazole, pH 8.0 (wash buffer 1), followed by washes with 20 column volumes of 8 M urea in 100 mM $NaH_2PO_4$, 10 mM Tris, 300 mM NaCl, 40 mM imidazole, pH 8.0 (wash buffer 2). The bound protein was eluted with a buffer containing 8 M urea, 100 mM $NaH_2PO_4$, 10 mM Tris, 300 mM NaCl, 250 mM imidazole, pH 8 (Elution Buffer). The fractions containing the protein were pooled and dialyzed at 4° C. against multiple changes of dialysis buffer (10 mM $NaH_2PO_4$, 300 mM NaCl). Purified proteins were characterized using standard biochemical techniques including SDS gel electrophoresis, isoelectric focusing, and western blot analysis using antibodies against different domains of the expressed protein.

D. Example 4

Breaking Tolerance to a "Self" Protein Using a Chimeric Antigen Fusion Protein In order to evaluate the immune response to chimeric antigen fusion proteins, mice were immunized with purified HBV S1/S2, TBD or S1/S2-TBD proteins and the antibodies produced against the individual proteins were quantified. Proliferation of splenic T cells harvested from immunized mice was evaluated following challenge with the respective proteins.

BALB/c mice at 15 weeks of age were used for the immunizations. Mice were injected subcutaneously with S1/S2-TBD (4.15 μg), S1/S2 (4.15 μg) or TBD (4.15 μg) four times at two week intervals. Blood samples were collected before the start of immunizations and a week following each of the immunizations. Serum was prepared from clotted blood samples and used for the estimation of antibody levels produced by the host animal against the respective antigens injected.

1. ELISA for Detection of Antibodies Against HBV S1/S2, TBD or S1/S2-TBD

A 96-well plate was coated with antigens HBV S1/S2, TBD or S1/S2-TBD at a concentration of 1.0 μg/mL overnight at 4° C. The plate was washed with PBS containing 2% BSA. Diluted serum from the respective animal was added to each of the wells at various dilutions (1:10-1:500) and incubated at 37° C. for 1 hr. The plate was washed with PBS containing 0.05% Tween 20 (wash buffer). Goat anti-mouse IgG Fab-horse radish peroxidase (HRP) (1:5000) dilution was added to the wells and incubated at 37° C. for 1 hr. The plate was washed with wash buffer and color was developed using 2-2' azino-di-(3-ethyl benzylthiazoline-6-sulfonate) (KPL, Guildford, UK). The optical density of resulting color in the samples was measured using an ELISA plate reader (Molecular Devices, USA) at a wavelength of 405 nm. Negative control for the experiment was pre-immune serum from the same animal, which was subtracted from all the experimental values. The results for mice immunized with HBV S1/S2-TBD are presented in Table 4. The chimeric antigen elicits a strong antibody response against the chimeric antigen (S1/S2-TBD).

TABLE 4

Humoral response to S1/S2-TBD

| | | Level of antibody binding to: | | |
|---|---|---|---|---|
| | | HBV S1/S2-TBD | HBV S1/S2 | TBD |
| Mice immunized with | HBV S1/S2-TBD | 0.192 | 0.059 | 0.048 |
| | HBV S1/S2 | 0.073 | 0.015 | 0.025 |
| | TBD | 0.076 | 0.017 | 0.036 |

The antibody response here is of a multivalent (or multi-epitopic) nature. The results presented in Table 4 show that antibodies produced by mice immunized with HBV S1/S2-TBD bind to the chimeric antigen and to the S1/S2 protein target coated on the plate. Therefore, antibodies are produced against the S1/S2 component of the chimeric antigen. Likewise, antibodies produced by mice immunized with HBV S1/S2-TBD bind to the target binding domain protein (Table 4). Chimeric antigen that contains protein of mouse origin can generate a humoral immune response in a mouse, evidence that the chimeric antigen can convert a "self" antigen into "foreign." Accordingly, it is possible to break tolerance to a protein otherwise treated as a "self" protein.

2. T Cell Proliferation Assay

Animals were sacrificed a week after the fourth immunization, the spleen was removed, and a single cell suspension was produced. Cells were seeded in triplicate at a cell density of $4 \times 10^5$ cells/well in a 96-well plate. They were loaded with the respective antigens, HBV S1/S2, TBD or S1/S2-TBD, at concentrations of 0.1 μg/mL, 1.0 μg/mL and 10 μg/mL. Negative control cells received media alone and the positive control for T cell proliferation was Phytohemagglutinin (PHA) at 1.0-5.0 μg/mL. The cell cultures were incubated for 4 days at 37° C. under an atmosphere of 7% $CO_2$. Each of the wells of cells was pulsed with 1.0 mCi of $^3[H]$-thymidine and incubated for an additional 18 hours. The cells were harvested using TOMTEC MACH 3 cell harvester (Hamden, Conn., USA) and the radioactivity bound to the glass fibre filter (Wallac Oy, Turku, Finland) was quantified using a Wallac Trilux 1450 Microbeta liquid scintillation and luminescence counter (Wallac, USA). The results are shown in Table 5.

TABLE 5

Cellular response to HBV S1/S2-TBD

| | Mean counts per minute (CPM) | | |
|---|---|---|---|
| | 0.1 μg/mL | 1 μg/mL | 10 μg/mL |
| HBV S1/S2-TBD | 36.7 ± 17.0 | 32.7 ± 5.0 | 21.3 ± 7.0 |
| HBV S1/S2 | 10.7 ± 2.1 | 26.7 ± 9.6 | 25.7 ± 10.3 |
| TBD | 32.7 ± 19.1 | 17.0 ± 2.6 | 35.7 ± 27.2 |
| Cells alone | 21.3 ± 12.5 | | |
| 1.0 mg/ml PHA | 39.3 ± 18.6 | | |

T cell proliferation was seen when challenged with HBV S1/S2-TBD, S1/S2 or TBD. Immunization with the chimeric antigen induced a multivalent T cell response, i e., a response against different parts of the same protein. Chimeric antigen that contain protein of mouse origin can generate a cellular immune response in a mouse, evidence that the chimeric antigen can convert a "self" antigen into "foreign." Therefore, it is possible to break tolerance to a protein otherwise treated as a "self" protein.

E. Example 5

Antigen Presentation Assays

The ability of HBV S1/S2-TBD to elicit an immune response was measured using an ex vivo antigen presentation assay. The generation of an effective T cell response following multiple stimulations of naïve T cells with antigen-loaded antigen presenting cells (APCs) such as dendritic cells (DCs) was assessed by quantitating the increase in the number of antigen-specific T cells as well as the ability of the T cells to produce the Th1 cytokine IFN-γ.

1. Selection of Monocytes by Adhesion

Peripheral blood mononuclear cells (PBMCs) were thawed by the addition of AIM-V (ratio of 9 ml of AIM-V added to 1 ml of frozen cells). The cells were then centrifuged at 200× g for 5 min, the supernatant removed, and the cells resuspended in AIM-V/1% matched serum and added to either a 100 mm culture dish or a T-25 culture flask. The PBMCs were incubated for 1 hr at 37° C. in a humidified incubator under 7% $CO_2$. To remove non-adherent cells, the culture was triturated several times, the supernatant discarded, and the cells washed once with AIM-V medium. Monocytes were harvested with a cell scraper and centrifuged at 300× g for 5 min. The cell pellet was re-suspended in AIM-V/2.5% matched serum at $2×10^6$ cells/ml and seeded into a 24-well dish. The cytokines IL-4 and GM-CSF (1000 IU/ml each) were added to drive the differentiation of monocytes into immature DCs.

2. Fast or Slow Antigen Presentation Assay

For the Fast Antigen Presentation Assay (APA), antigen was added to immature DCs within 4 to 24 hr of isolation. After a further 24 hr, antigen loaded immature monocytes were induced to mature by culturing with $PGE_2$ (1 μM), IL-1β (10 ng/ml), and TNF-α (10 ng/ml) for 24 hr. The mature DCs were then co-cultured (first stimulation) with autologous T cells. The T cells were generated from the same PBMCs as the DCs by means of negative selection using a magnetic T cell isolation kit (Dynal) according to the manufacturer's directions.

T cells were then re-stimulated 7 days later with antigen loaded mature DCs in the presence of IL-2 (20 IU/ml), IL-7 (10 ng/ml), and IL-15 (5 ng/ml). Following a 7 day incubation, T cells were re-stimulated a third time with antigen loaded mature DCs. The third stimulation lasted for 6 hr whereupon the T cells were harvested and immunostained for CD3, CD8 and IFN-γ expression, and analyzed by flow cytometry.

For the Slow APA, monocytes were allowed to differentiate into immature DCs in the presence of GM-CSF and IL-4 for 5 to 6 days before addition of antigen. Two hours after antigen addition, immature DCs were matured with TNF-α (10 ng/ml) and IFN-α (50 IU/ml). Seven days post isolation, the mature DCs were co-cultured (first stimulation) with autologous T cells (described above).

T cells were then re-stimulated 7 days later with antigen loaded mature DCs in the presence of IL-2, IL-7, and IL-15. Following a 7 day incubation, cells were re-stimulated a third time with antigen loaded mature DCs. After an 18 hr incubation the T cells were harvested and immunostained for CD3, CD8 and IFN-γ expression, and analyzed by flow cytometry.

2. PBMC Antigen Presentation Assay

In this assay, the initial culture consists of total PBMCs (ie. lymphocytes and monocytes) that are incubated with antigen and IL-2 with the assumption that the system resembles the in vivo immune response since all the cell types are present to participate (Maini, M. K et. al J. Exp. Med. 191:1269-1280, 2000). PBMCs are thawed, washed and immediately incubated with antigen. Following 4 days of culture to allow for antigen uptake and presentation, IL-2 (20 IU/ml) was added and left for an additional 8 days (i.e. day 12 of the experiment). Two days prior to the second stimulation (i.e. day 10 of the experiment), DCs are isolated by adhesion as described above, and immediately incubated with GM-CSF, IL-4 and antigen for 24 hr. As with the Fast APA, the immature DCs are allowed to differentiate for 24 hr following the addition of $PGE_2$, IL-1β, and TNF-α. The loaded mature DCs are then added to the PBMC culture (second stimulation, day 12 of the experiment) in the presence of IL-2, IL-7, and IL-15. The third stimulation occurred on day 21 of the experiment with antigen loaded mature DCs prepared 2 days prior as described. Following a 6 hr incubation, the T cells were harvested and immunostained for CD3, CD8 and IFN-γ expression, and analyzed by flow cytometry.

For all antigen presentation assays discussed above, a portion of the T cells at the end of the assay were incubated for an additional 3-5 days and examined for specific T cells by tetramer analysis (see below).

4. HBV S1/S2 Elicits a T Cell Response Against HBV S1 and S2 Peptides

The PBMC APA was used to generate T cells which were then assessed for their antigen specificity. Thus, PBMCs from healthy HLA-A2 individuals were cultured in AIM-V containing 2.5% matched sera in 96-well plates at $5×10^5$ cells/ml. Antigen (ie. 10 μg/ml S1/S2-TBD) was added and the cells were cultured for 4 days at 37° C. IL-2 was then added at 20 IU/ml and the cells were cultured for an additional 8 days, with media changes (AIM-V/2.5% matched serum and 20 IU/ml IL-2) every 2-3 days. The majority of the cells remaining at the end of the 12 day culture were T cells, and these T cells were restimulated with autologous antigen-loaded mature DCs in the presence of IL-2 (20 IU/ml), IL-7 (10 ng/ml), and IL-15 (5 ng/ml).

The antigen-loaded mature DCs for the second and third stimulation of the T cells in the APA were generated over a 48 hr period using the procedure described below. The monocytes were isolated from total PBMC by adherence on plastic tissue culture dishes. The cells, about 85% of which were monocytes as determined by FACS analysis (CD11c+, CD14+, CD19−, and CD3−), were cultured in a 96-well plate at $1×10^5$ cells/well containing 100 μl of AIM-V/2.5% matched sera with the cytokines IL-4 and GM-CSF at 1000 IU/ml, and 4 hr later antigen such as S1/S2-TBD was added. Following a 20 hr incubation, the generated immature DCs were differentiated to mature DCs by culturing for a further 24 hr in the presence of $PGE_2$ ($1×10^{-6}$ M), IL-1β (10 ng/ml), and TNF-α (10 ng/ml).

T cells were cultured for 7 days following the second stimulation, with media changes (AIM V with 2.5% matched serum and 20 IU/ml IL-2) every 1-2 days. The T cells (day 19 of culture) were then stimulated a third time with antigen-loaded mature DC (generated over a 2 day procedure as outlined above) in the presence of IL-2, IL-7, and IL-15 (as above) and either assessed for IFN-γ production after a 6 hr culture or cultured for 5 days (with media changes every 1-2 days with AIM-V/2.5% matched serum and 20 IU/ml IL-2) and then assessed for T cell specificity to HBV preS antigen using HBV preS tetramers (day 24 of culture).

Figure 2:
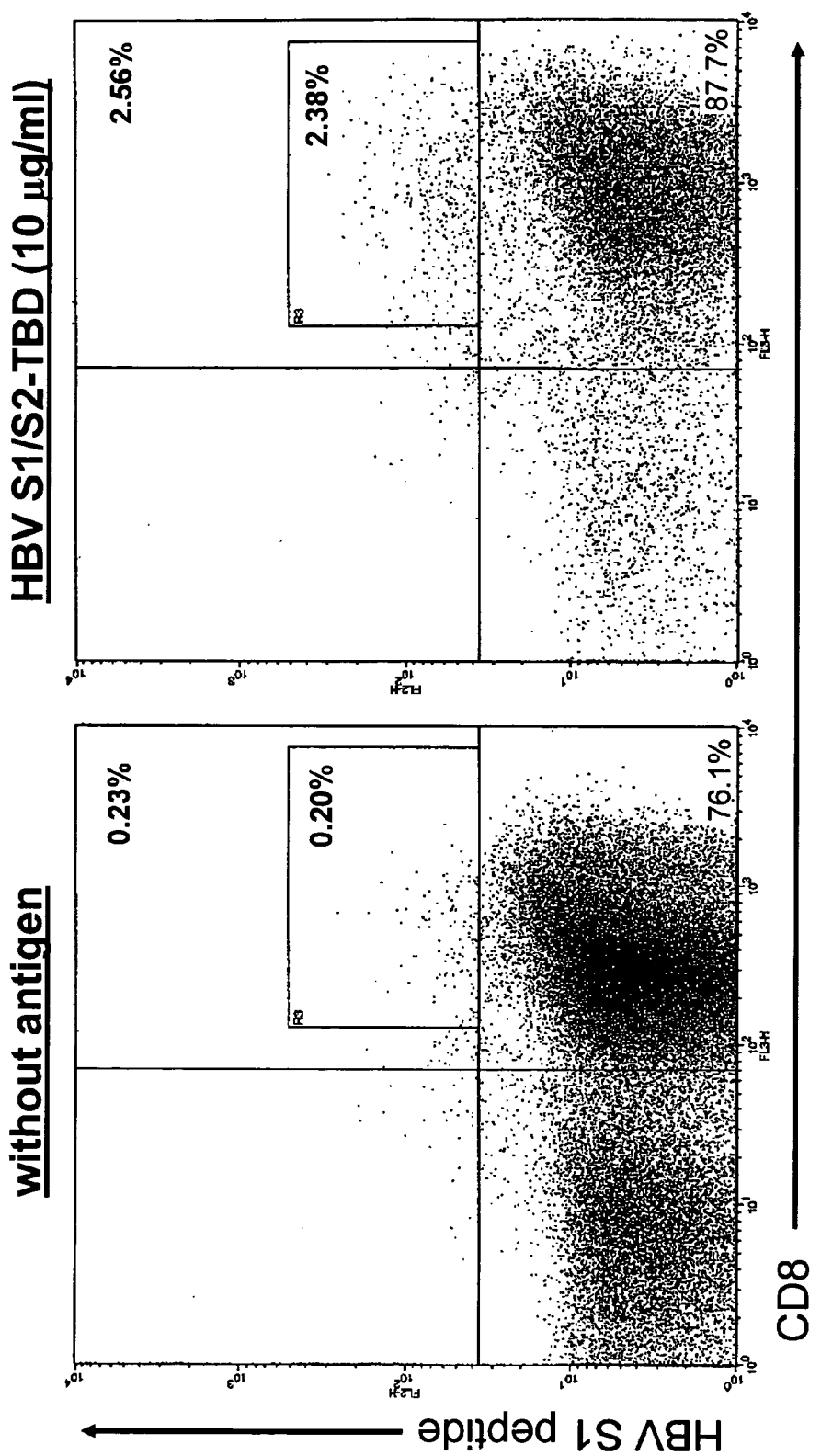
Figure 3:
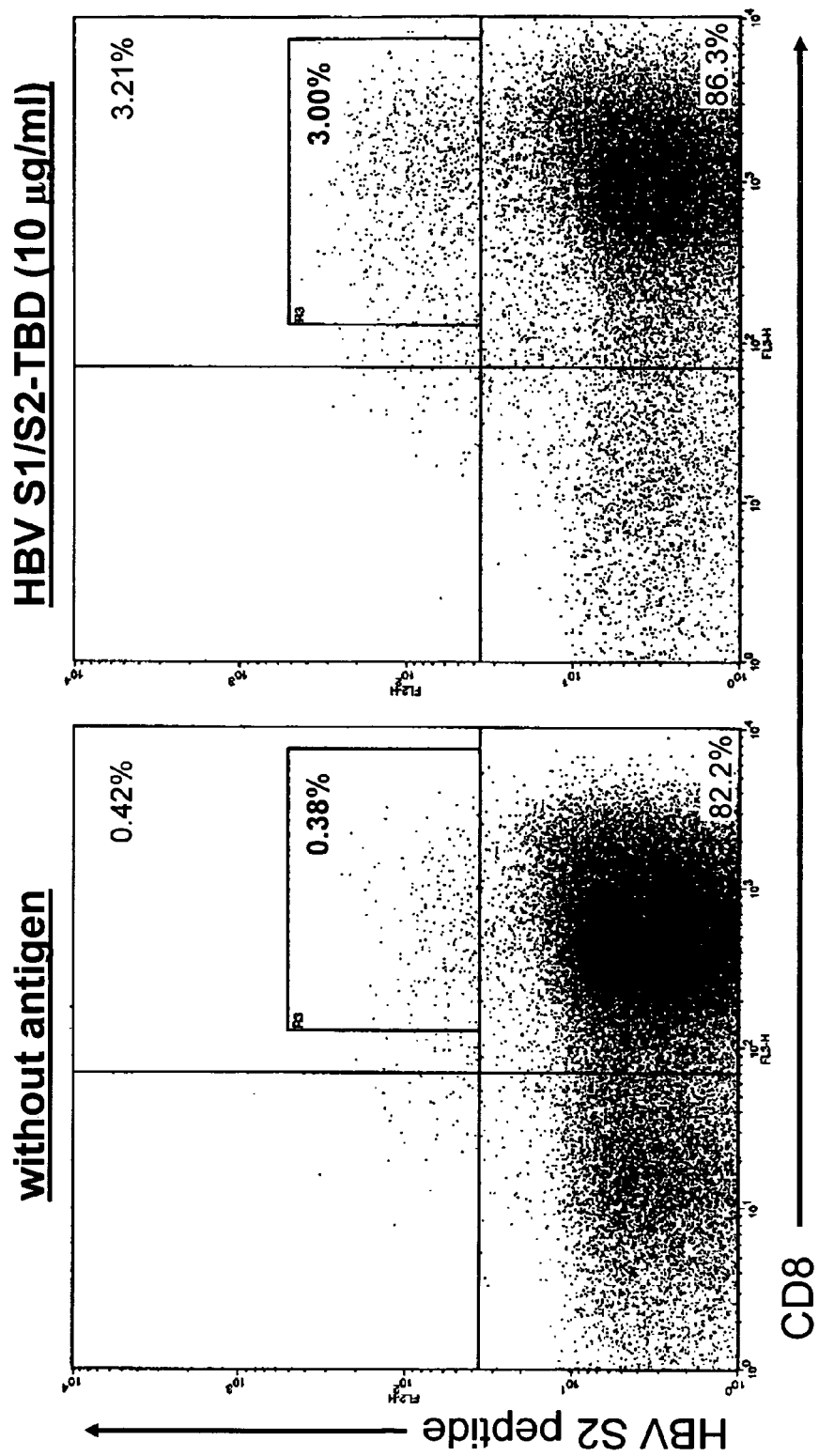

Tetramer analysis was performed with custom synthesized iTag MHC class I tetramers (Beckman Coulter) according to the manufacturer's protocol. Thus cells were harvested, washed, and transferred to a 96-well v-bottom plate at ~$2×10^5$ cells/well in 20 μL. The cells were labeled at 20° C. for 30 min with mAb specific to CD3 (anti-CD3-FITC) and CD8 (anti-CD8-Cy-Chrome) together with either 2 μl PE-conjugated HLA-A*0201 preS1 tetramer (GMLTPVSTI, SEQ ID NO: 50) or a preS2 tetramer (NIASHISI, SEQ ID NO: 51). The cells were then washed, fixed with 2% paraformaldyde in PBS and transferred into 5 ml FACS tubes. The cells were acquired on a FACSCalibur (BD Biosciences) with 80,000-100,000 events per sample. Analysis was performed using CellQuest software (BD Biosciences) with a gate on the viable (based on the FSC/SSC profile) CD3+ population and the percentage of CD8+ cells labeling with tetramer was determined. When PBMCs were cultured with HBV S1/S2-TBD at 10 μg/ml and restimulated twice with HBV S1/S2-TBD-loaded mature DC, a marked percentage of the cells labeled positive with S1 tetramer (FIG. 2) and S2 tetramer (FIG. 3). This is in contrast to T cells cultured with antigen-unloaded mature DC, where the number of tetramer positive cells was not significant. Thus, S1/S2-TBD-loaded mature DC were able to induce the generation of a significant number of T cells with specificity to determinants of HBV S1 and HBV S2 antigens.

F. Example 6

Breaking Tolerance to DHBV and DHBV Antigens Using Chimeric Antigen Fusion Protein DHBV has served as a powerful animal model in the development of antiviral therapy for HBV. Pekin ducks, congenitally infected with DHBV have been used to study the mechanism of replication of the virus and for the screening of antiviral compounds. Two kinds of duck models were used in the present invention. First is the congenitally DHBV-infected ducks. This resembles the vertical transmission of the HBV infection in man. The second model is the persistent infection model where newly hatched ducklings are infected with DHBV and these carry the infection. This second model resembles the horizontal transmission of the HBV infection in man.

1. Congenitally DHBV-infected Ducks

Congenitally DHBV-infected ducks, at four weeks of age, were divided into two groups. A sample of blood (1.0 mL) was collected for reference of pre-immunization antibody levels and blood samples were collected every week before the vaccinations. The experimental group received DHBV Core-TBD chimeric antigen fusion protein 19.95 mg/dose injected subcutaneously every week on the same day until week 5. During week 6, the dose was doubled and injected once every four weeks until vaccinations were discontinued at week 26. The placebo group received the equivalent volume of the buffer (20 mM Sodium Phosphate pH 8.0, 300 mM NaCl).

A 96-well plate was coated with antigens, DHBV Core, TBD or DHBV Core-TBD, at a concentration of 1.0 µg/mL overnight at 4° C. The plate was washed with phosphate buffered saline (PBS) containing 2% BSA. Diluted serum from the respective animal was added to each of the wells at various dilutions (1:10-1:500) and incubated at 37° C. for 1 hr. The plate was washed with PBS containing 0.05% Tween 20 (wash buffer). Goat anti-duck IgG-HRP (1:5000) dilution was added to the wells and incubated at 37° C. for 1 hr. The plate was washed with wash buffer and color was developed using 2-2'-azino-di-(3-ethylbenzylthiazoline-6-sulfonate) (KPL, Guildford, UK). The optical density of resulting color in the samples was measured using an ELISA plate reader (Molecular Devices, USA). Antibody titers were calculated relative to the pre-immune serum from the same animal.

Anti-core antibody levels in the serum from congenitally DHBV-infected ducks in the control and experimental groups of ducks, at weeks 0, 3 and 6, are shown in Table 6. Although the ducks have a chronic DHBV infection, the antibody levels are low, due to the chronic nature of the infection and the immune system not recognizing the antigen as a foreign molecule. On immunization with DHBV Core-TBD chimeric antigen, the host immune system recognized the viral antigen and mounted a humoral response against the core antigen that is already present in the host, thus breaking the host tolerance to a viral antigen.

TABLE 6

Humoral response to DHBV Core-TBD

| | | Antibody binding ($OD_{405}$) | |
|---|---|---|---|
| | | anti-DHBV Core | anti-TBD |
| Vaccinated ducks | Week 0 | 0.058 ± 0.005 | 0.005 ± 0.003 |
| | Week 3 | 0.131 ± 0.029 | 0.092 ± 0.059 |
| | Week 6 | 0.166 ± 0.021 | 0.147 ± 0.038 |
| Control Group | Week 0 | 0.062 ± 0.016 | 0.003 ± 0.002 |
| | Week 3 | 0.074 ± 0.015 | 0.010 ± 0.005 |
| | Week 6 | 0.087 ± 0.012 | 0.035 ± 0.017 |

Similarly, the duck immune system recognized the TBD component of the chimeric antigen as a foreign antigen and generated an immune response against this part of the fusion protein as well. Plates were coated with TBD and the serum from individual ducks evaluated for the antibody levels by ELISA. The results from this study are presented in Table 6.

2. Post-Hatch DHBV-Infected Ducks

Normal ducklings were infected with DHBV-containing duck serum a day after the ducklings were hatched. This is standard practice in the field of DHBV research. The presence of persistent viremia was verified using established techniques at week four before the start of the immunizations. DHBV-infected ducks were divided into two groups. A sample of blood (1.0 mL) was collected from each duck for reference of pre-immunization antibody levels and blood samples were collected every week before the vaccinations. The experimental group received DHBV Core-TBD chimeric antigen fusion protein 19.95 µg/dose injected subcutaneously every week on the same day until week 5. During week 6, the dose was doubled and injected once every four weeks until vaccinations were discontinued at week 30. Blood samples were collected from the placebo group, which received the equivalent volume of the buffer (20 mM Sodium Phosphate pH 8.0, 300 mM NaCl).

Antibody levels in sera collected from ducks at weeks 0, 3 and 6 are presented. Anti-core antibody levels in the serum from post-hatch DHBV-infected ducks in the control and experimental groups of ducks are shown in Table 7. Since DHBV has established a persistent infection, the antibody levels are low, as the immune system does not recognize the viral antigen as a foreign molecule. On immunization with DHBV Core-TBD chimeric antigen, the host immune system recognized the viral antigen and mounted a humoral response against the core antigen that is already present in the host, thus breaking the host tolerance to a viral antigen. The antibody levels against TBD also increased (Table 7). Therefore there is a multivalent (or multi-epitopic) immune response against different parts of the same chimeric antigen.

TABLE 7

Humoral response to DHBV Core-TBD

| | | Antibody binding to: | |
|---|---|---|---|
| | | DHBV Core | TBD |
| Vaccinated ducks | Week 0 | 0.066 ± 0.011 | 0.003 ± 0.002 |
| | Week 3 | 0.145 ± 0.014 | 0.072 ± 0.043 |
| | Week 6 | 0.170 ± 0.009 | 0.163 ± 0.052 |
| Control Group | Week 0 | 0.083 ± 0.016 | 0.008 ± 0.010 |
| | Week 3 | 0.112 ± 0.042 | 0.011 ± 0.007 |
| | Week 6 | 0.138 ± 0.041 | 0.026 ± 0.013 |

G. Example 7

Chemically Cross-Linked HBV sAg-Fc (Murine)

Solutions of 100 µg sAg (US Biologicals; Cat# H 1910-27) and 100 µg Mouse Polyclonal IgG Fc fragment (Harlan Sera-Lab Ltd., Cat# PP-19-01) were dialyzed against 100 mM HEPES pH 8.7 overnight at 4° C. The protein solutions were mixed together, dimethyl suberimidate (DMS; Pierce Cat # 20700) was added immediately to a final concentration of 10 mM, and the mixture was incubated at room temperature for 1 hr. The reaction was stopped by the addition of 0.1 M Tris HCl pH 7.8. The reaction mixture was loaded on a Sephadex G 75 column (0.7×12 cm), and fractions were eluted using phosphate buffered saline. 0.5 ml fractions were collected and the fractions containing sAg/Fc at a molar ratio of 1:1, as estimated by ELISA using the respective antibodies were pooled.

The pooled fractions were used for antigen presentation assays. (Berlyn, et al., Clin. Immunol. 101: 276-283, (2001)). Immature dendritic cells were cultured for four days with GM-CSF/IL4, incubated with the sAg-Fc conjugate and matured in the presence of TNFα and interferon-α. Autologous CD3+ T cells were added to the mature dendritic cells. Following three rounds of exposure to the mature dendritic cells, T cell stimulation was quantitated by measuring the production of intracellular interferon-γ, using flow cytometry. The levels of intracellular interferon-γ produced in T cells in the presence of conjugate were substantially higher than in the presence of the sAg or the Fc fragment alone (Table 8).

TABLE 8

T cell response to HbsAg-Fc DMS conjugate

| | % IFN-γ positive T cells |
|---|---|
| No antigen | 0.19 |
| Mouse Fc (2.5 µg/mL) | 0.46 |
| HBsAg (2.5 µg/mL) | 0.04 |
| HBsAg (2.5 µg/mL) + mAb(2C12) (2.5 µg/mL) | 0.12 |
| HBsAg-Fc DMS conjugate (5.0 µg/mL) | 0.74 |

H. Example 8

Antigen Presentation Assays

Antigen presentation assays were performed using human PBMC-derived dendritic cells according to established protocols (Berlyn, et al., supra (2001)). A protocol summary for the T cell stimulation assay is presented in schematic form.

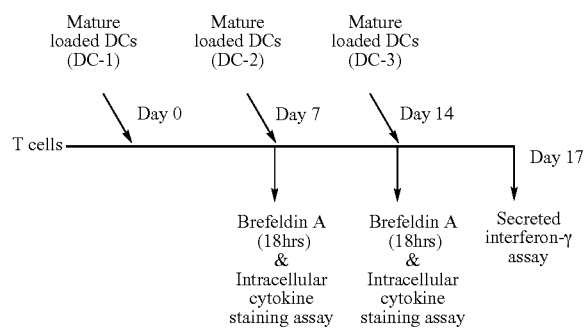

1. Preparation of Mature, Loaded Dendritic Cells

Monocytes were generated from leukapheresis samples from healthy donors and were depleted of lymphocytes and granulocytes by incubation with anti-CD2, CD7, CD16, CD19, and CD56 antibodies. This was followed by incubation with magnetic bead conjugated anti-mouse IgG and separation on a magnet (Dynal). Negatively selected cells were greater than 95% pure monocytes as characterized by flow cytometry using a broad CD marker panel (CD14+, CD11c+, CD19−, CD3−, CD4−, CD64+, CD32+, CD86+, CD16−). Next, monocytes were incubated with IL-4 and GM-CSF (R&D Systems) for 4 days in AIM V plus 2.5% matched human serum to generate immature dendritic cells. Again, an aliquot of the cells was stained with the broad CD marker panel to ensure purity and identity of the cells. The cells then were loaded with HBV S1/S2-TBD (5.0 µg/ml), HBV S1/S2 (2.5 µg/ml), or TBD (2.5 µg/ml) for 2-4 hours at 37° C., and matured with interferon-α and TNF-α for 3 days. Dendritic cells were checked again using flow cytometry for an array of CD markers to ensure that cells had undergone proper maturation. The resulting mature, loaded dendritic cells were used for the T cell stimulation assay.

2. T Cell Stimulation Assay: Cytokine Analysis

T cells were generated from the same sample of PMBCs as the dendritic cells by means of negative selection using a magnetic T cell isolation kit (Dynal) according to the manufacturer's directions. Mature, loaded dendritic cells (DC-1) were washed thoroughly and added to the T cells (Day 0). The T cells and dendritic cells were incubated for 7 days. On Day 7, the T cells were re-stimulated with mature, loaded dendritic cells (DC-2). An aliquot of the cells was taken 2 hours later. The aliquot of cells was incubated with Brefeldin A (Golgiplug ™, R&D Systems) for 18 hours and then assayed for intracellular cytokine staining as described below.

The remaining cells were incubated for another 7 days. On Day 14, the remaining cells were stimulated with a third batch of mature, loaded dendritic cells (DC-3). An aliquot of the cells was taken 2 hours later. The aliquot of cells was incubated with Brefeldin A (Golgiplug ™, R&D Systems) for 18 hours and then assayed for intracellular cytokine staining as described below.

For intracellular cytokine staining, cells were stained with anti-CD3-FITC and anti-CD8-Cy-Chrome for 30 minutes, washed, fixed, permeabilized, and then stained with anti-interferon-γ-PE for 30 minutes on ice. The cells were washed and analyzed by flow cytometry (FACScan, BD Biosciences). The results are shown in Table 9.

TABLE 9

| CD3+/IFN-γ+ T cells | |
|---|---|
| | Day 21 |
| HBV S1/S2-TBD | 6.2 ± 4.6 |
| HBV S1/S2 | 1.9 ± 1.7 |
| TBD | 1.6 ± 0.9 |
| No antigen | 0.58 ± 0.21 |

After removal of the aliquot at Day 14, the remaining T cells were incubated for an additional three days and the supernatant then was used for measuring the level of secreted interferon-γ by ELISA (Opt E1A ELISA kit, BD Biosciences). T cell stimulation was evaluated by measuring intracellular and secreted interferon-γ levels. The results are presented in Table 10. The chimeric antigen S1/S2-TBD induced the production of higher interferon-γ levels compared to either the immune response domain or the TBD domain of the molecule when tested alone, at equivalent concentrations. It should be pointed out that 5 µg dose of S1/S2-TBD contains roughly 2.5 µg each of the components.

TABLE 10

Intracellular and Secreted Interferon-γ Levels

|  | % IFN-γ positive T cells | Secreted IFN-γ (pg/ml) |
|---|---|---|
| HBV S1/S2-TBD | 3.5 | 60 |
| HBV S1/S2 | 2.1 | 18.9 |
| TBD | 2.5 | 11.9 |
| No antigen | 0.77 | 4.4 |
| T cells alone | 0.21 | 1.6 |

Various concentrations of S1/S2-TBD were tested for the T cell response. The effect of S1/S2-TBD was greater than the tetanus toxoid treatment at similar concentrations. At concentrations lower than 5 μg/mL, the chimeric antigen elicited a concentration dependent increase in the production and secretion of interferon-γ. Interferon-γ production and secretion by CD3+ T cells increased in a concentration dependent manner following S1/S2-TBD antigen presentation by dendritic cells, as shown in Table 11. The positive response at low concentrations would be beneficial with respect to the dose necessary for vaccination and the cost of manufacturing of a vaccine.

TABLE 11

Concentration Dependence of Response to Chimeric Antigen

|  | % IFN-γ positive T cells | Secreted IFN-γ (pg/ml) |
|---|---|---|
| HBV S1/S2-TBD (1.25 μg/ml) | 1.5 | 18 |
| HBV S1/S2-TBD (2.5 μg/ml) | 4.3 | 40 |
| HBV S1/S2-TBD (5 μg/ml) | 3.5 | 60 |
| HBV S1/S2-TBD (10 μg/ml) | 4.3 | 20 |
| Tetanus toxoid | 3.3 | 33 |
| No antigen | 0.77 | 4.4 |
| T cells alone | 0.21 | 1.6 |

I. Example 9

Binding and Uptake of Chimeric Antigens

1. Preparation of Mature, Loaded Dendritic Cells

Peripheral blood mononuclear cells (PBMC) were obtained from Ficoll/Histopaque (Sigma) treatment of a leukapheresis cell preparation (Berlyn, et al., supra (2001)). Monocytes were separated from the PBMC population by negative selection using a monocyte isolation kit (Dynal) following the manufacturer's directions. The monocytes were greater than 95% pure as assessed by antibody analysis and flow cytometry (CD14+, CD11c+, CD19−, CD3−, CD4−, CD64+, CD32+, CD86+, CD16−). Monocytes were washed twice with AIM-V (Invitrogen) media containing L-glutamine, streptomycin sulfate (50 μg/mL) and gentamicin sulfate (10 μg/mL) with 1% donor matched sera (isolated as described in Berlyn, et al., supra (2001)). Next, the monocytes were cultured in AIM-V media containing 2.5% donor matched sera and the cytokines GM-CSF and IL-4 to differentiate the cells toward the dendritic cell (DC) lineage. The cells were incubated in 12-well tissue culture plates at 37° C. under a 7% $CO_2$ atmosphere.

The monocyte-derived dendritic cells were harvested on days 1 through 4. The cells were subsequently washed once with AIM-V media with 0.1% BSA (Sigma), and twice with Dulbecco's phosphate buffered saline (Invitrogen) with 0.1% (w/v) BSA (PBSB). The monocyte-derived dendritic cells were used in 4° C. labeling or binding assays or in 37° C. binding/uptake assays.

2. Binding of Chimeric Antigens to Maturing Dendritic Cells

The extent of binding of S1/S2-TBD relative to murine IgG1 and IgG2a to maturing dendritic cells was compared. Dendritic cells were isolated at various days of ex vivo culture (from day 0 to day 4) and treated with S1/S2-TBD (10 μg/mL) or with murine IgG1 (2C12, the parent mAb from which TBD was produced) or IgG2a (G155-178, 90 μg/mL) for 1 hour at 4° C. The cells were treated with F(ab')$_2$ goat anti-mouse Alexa-488 (10 μg/mL) in PBSB for 20 minutes. The cells were washed twice with PBSB and resuspended in PBSB with 2% paraformaldehyde (PF) and acquired by a Becton Dickinson (BD) FACScan fitted with CellQuest acquisition and analysis software (BD). A gate was made on the viable cell population as determined by the FSC and SC scatter profile and >10,000 events were acquired. To determine the percentage of positive cells, a gate was set based on negative control treated cells (isotype control labeled or cells labeled with F(ab')$_2$ goat anti-mouse Alexa-488 alone). The percent of specific positive cells was calculated as:

$$\frac{\% \text{ positive cells test sample} - \% \text{ positive cells control}}{100 - \% \text{ positive cells of control}} \times 100$$

The relative mean fluorescent intensity (MFI) was determined as the MFI of the test sample minus the MFI of the control sample.

The binding of S1/S2-TBD relative to IgG1 and IgG2a on DC after 1 to 4 days of culture is shown in Table 12.

TABLE 12

Binding of Chimeric Antigen or Antibody to Maturing Dendritic Cells

|  | % Specific positive dendritic cells | | | |
|---|---|---|---|---|
|  | Day 1 | Day 2 | Day 3 | Day 4 |
| HBV S1/S2-TBD | 91.9 | 98.5 | 88.3 | 97.9 |
| IgG1 | 21.2 | 19.5 | 29.3 | 49.1 |
| IgG2a | 28.0 | 17.4 | 14.3 | 13.5 |

S1/S2-TBD binding was clearly much greater than the binding of either IgG1 or IgG2a with more S1/S2-TBD binding evident on day 1 than on day 4. These experiments demonstrated that S1/S2-TBD was bound with high efficiency to the maturing dendritic cells.

3. Uptake of Chimeric Antigens to Maturing Dendritic Cells

To determine the extent of uptake of chimeric antigens (e.g. HBV S1/S2-TBD) compared with IgG1 and IgG2a, cells were incubated with various concentrations of the antigen, IgG1 (2C12, the parent mAb from which TBD was produced) or IgG2a (G155-178) for 1 hour at 37° C. in AIM V media with 0.1% BSA. Cells were washed twice in PBSB and fixed with PBS with 2% PF overnight at 4° C. Subsequently, the cells were washed twice in PBSB and permeabilized with PBS containing 0.1% (w/v) saponin (Sigma) for 40 minutes at 20° C.

The cells were washed twice with PBSB and incubated with $F(ab')_2$ goat anti-mouse Alexa-488 (10 μg/mL) in PBSB with 0.1% (w/v) saponin for 20 minutes at 4° C. After washing twice in PBSB, the cells were resuspended in PBSB. A variant of this assay involved treating the cells as above with chimeric antigen, IgG1, or IgG2a for 10 minutes followed by the addition of $F(ab')_2$ goat anti-mouse Alexa-488 (10 μg/mL) for 50 minutes. Subsequently the cells were washed and resuspended in PBS with 2% PF.

Cells were acquired by a Becton Dickinson (BD) FACScan fitted with Cellquest acquisition and analysis software (BD).

A gate was made on the viable cell population as determined by the FSC and SC scatter profile and >10,000 events were acquired. To determine the percentage of positive cells, a gate was set based on negative control treated cells (isotype control labeled or cells labeled with F(ab')$_2$ goat anti-mouse Alexa-488 alone). The percent of specific positive cells was calculated as:

$$\frac{\% \text{ positive cells test sample} - \% \text{ positive cells control}}{100 - \% \text{ positive cells of control}} \times 100$$

The relative mean fluorescent intensity (MFI) was determined as the MFI of the test sample minus the MFI of the control sample.

Figure 4:
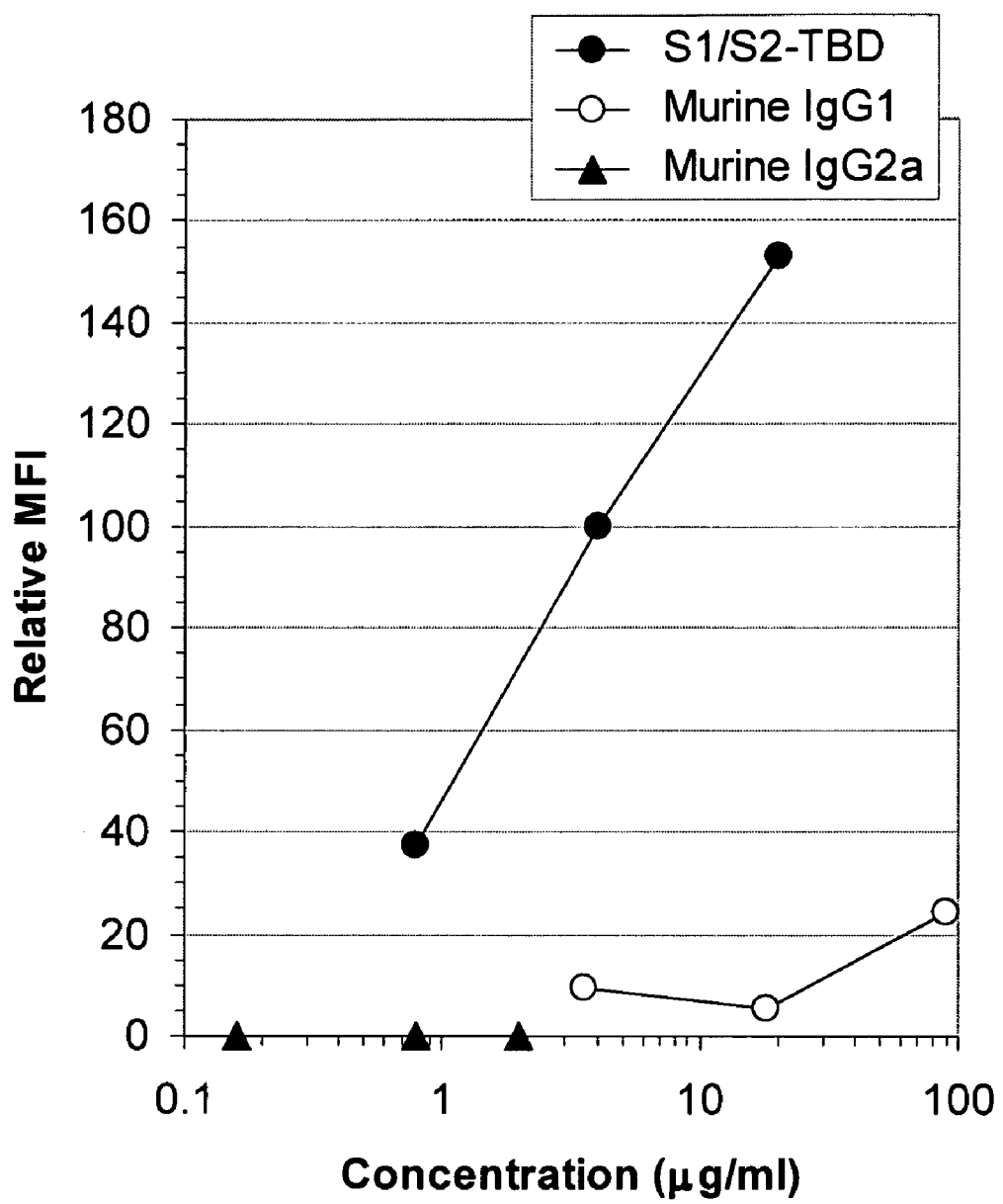

The uptake of S1/S2-TBD in comparison to murine IgG1 and IgG2a was estimated as a function of concentration on day 4 of dendritic cells maturation. The uptake was quantified at 37° C. for 1 hour and the results are shown in FIG. 4. There was a linear increase in the uptake of S1/S2-TBD with concentration. IgG1 was taken up at a much lower level and there was very little uptake of IgG2a. Therefore, the chimeric antigen S1/S2-TBD is taken up by the dendritic cells more efficiently than immunoglobulins.

J. Example 10

Expression of Fc-γ Receptors and CD206 on Maturing DC

There are several receptors on the antigen presenting cells that bind and take up antigens. The abundance of these receptors on maturing dendritic cells was evaluated using fluorescent labeled receptor-specific antibodies. FACS analysis was used to estimate percentage of specific receptor positive cells in the total population of dendritic cells. The degree of receptor expression was assessed by determination of the relative mean fluorescent intensity and as a function of relative fluorescent intensity (Table 13).

TABLE 13

Expression of Antigen Binding Receptors on Maturing Dendritic Cells

|  | % specific positive cells | | | | | Relative MFI | | | | |
| --- | --- | --- | --- | --- | --- | --- | --- | --- | --- | --- |
|  | Day 0 | Day 1 | Day 2 | Day 3 | Day 4 | Day 0 | Day 1 | Day 2 | Day 3 | Day 4 |
| CD16 | 20.8 | 26.3 | 6.2 | 0.8 | 5.9 | 4.3 | 10.8 | 2.7 | 0.0 | 1.6 |
| CD32 | 99.3 | 97.4 | 78.9 | 41.8 | 37.8 | 163.4 | 187.1 | 70.5 | 18.0 | 14.0 |
| CD64 | 84.0 | 71.9 | 18.2 | 9.6 | 5.3 | 28.0 | 12.8 | 3.7 | 2.7 | 1.0 |
| CD206 | 45.8 | 82.5 | 98.3 | 99.1 | 99.3 | 8.5 | 373.1 | 1180.6 | 1317.3 | 1680.4 |

The expression of CD64 (Fcγ receptor I) decreased with time in culture and at day 4 was almost negligible. In contrast, CD32 (Fcγ receptor II), and to a lesser extent CD16(Fcγ receptor III), continued to be expressed after 4 days of DC culture. On day 0 of culture, there was essentially no CD206 (mannose macrophage receptor) expression. But expression was induced upon culture with IL-4 and GM-CSF, and by day 4 CD206 was expressed at very high levels. Thus at day 4, when antigen was loaded in the antigen presentation assays, the dendritic cells possessed at least two potential receptors for the binding of chimeric antigens: CD32 and CD206. In addition, they had the full complement of the co-stimulatory molecules (data not shown). The expression of HLA-DR (Class II) and HLA-ABC (Class I) also increased with time in culture. Co-stimulatory molecules CD86 (B7.2) and CD80 (B7.1) were expressed throughout the period of the assay. These results indicate that the monocyte-derived dendritic cells were differentiating towards mature dendritic cells and were capable of antigen processing and presentation to T cells.

K. Example 11

Correlation of CD32/CD206 Expression and S1/S2-TBD Binding to Maturing DCs

There is a direct correlation between the expression of CD32/CD206 receptors and S1/S2-TBD binding to maturing dendritic cells. Since it was known that murine IgG1 binds to human CD32, it was expected that S1/S2-TBD, which contains the murine Fc component of IgG1, would also bind CD32. Furthermore, S1/S2-TBD by virtue of its high mannose glycosylation, would also be expected to bind to dendritic cells through the CD206 receptor.

Figure 5:
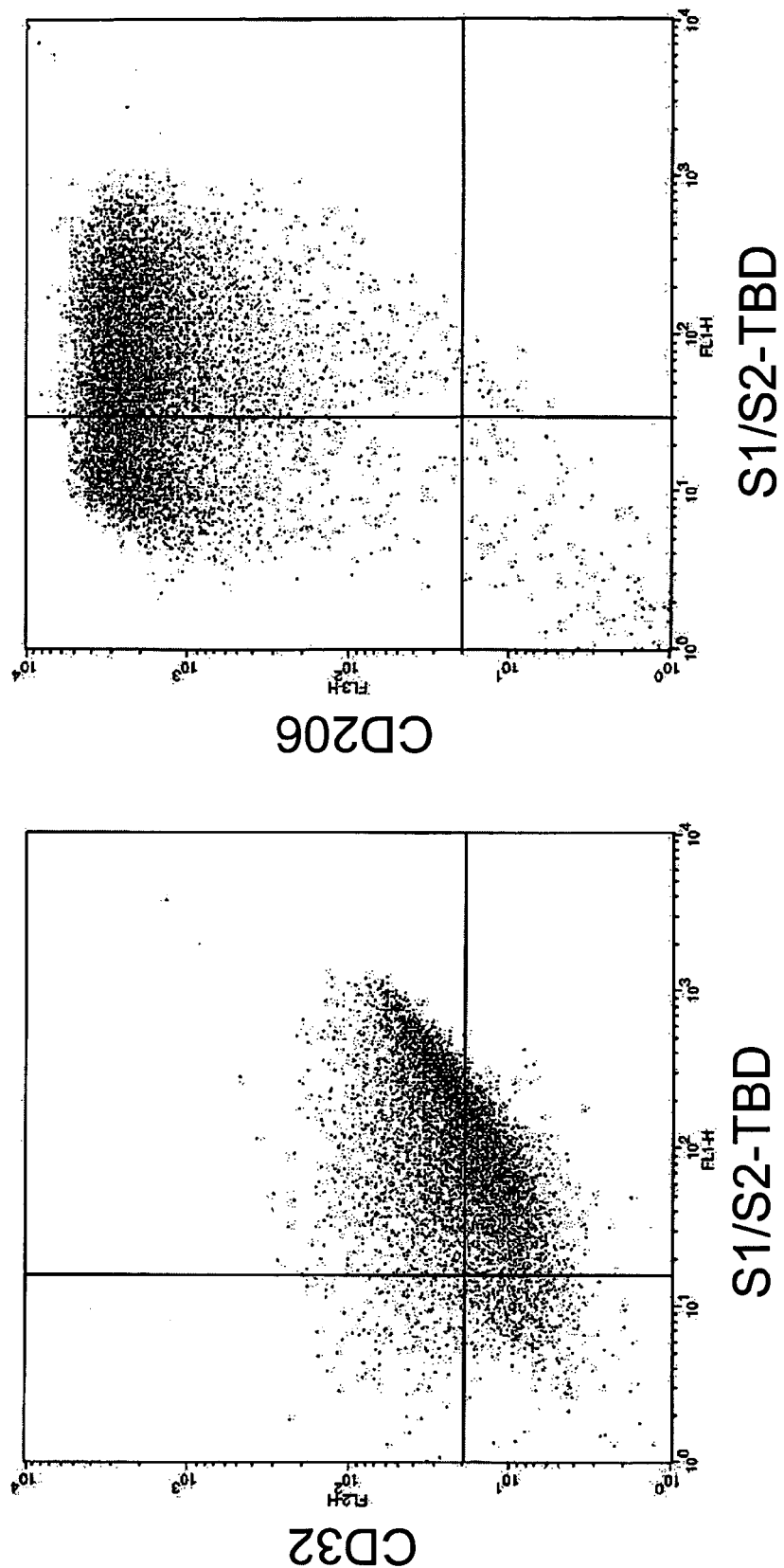

The dot plots in FIG. 5 show S1/S2-TBD binding (10 μg/mL) and CD32 expression as well as S1/S2-TBD binding and CD206 expression. There was a direct correlation between the extent of S1/S2-TBD binding and the degree of CD32 expression, which was relatively heterogeneous, ie., there was a broad degree of expression. These results demonstrate that S1/S2-TBD binds to CD32, and that the greater the expression of CD32, the greater was the degree of binding of the chimeric antigen S1/S2-TBD. The dot plot of S1/S2-TBD binding and CD206 expression shows that the vast majority of cells expressing CD206 also bound S1/S2-TBD A small percentage of the cell population was CD206 negative and was consequently negative for S1/S2-TBD binding. Therefore both CD32 and CD206 receptors correlate with the binding of S1/S2-TBD.

L. Example 12

Binding and Uptake of S1/S2-TBD is Primarily Via CD32 with CD206 Involved to a Lesser Extent The uptake of S1/S2-TBD in comparison to murine IgG1 and IgG2a was estimated as a function of concentration on day 4 of DC maturation. The uptake was quantified at 37° C. for 1 hour in the presence media, mannan (2 mg/ml, Sigma), and/or mouse Fcγ (2 mg/ml, Jackson ImmunoResearch Laboratories). Mannan is a competitive inhibitor of CD206 binding and therefore of uptake of antigens via CD206 on dendritic cells. Fcγ is a competitive inhibitor of CD32 binding and therefore CD32-meditated antigen uptake. The results are shown in Table 14.

TABLE 14

Inhibition of Chimeric Antigen Binding by Fc or Mannan

|  | Relative MFI | | | |
| --- | --- | --- | --- | --- |
|  | Mannan | Mouse Fcγ | Mannan & Fcγ | Media |
| 0.5 μg/ml HBV S1/S2-TBD | 7.6 | 0.5 | 0.6 | 3.0 |

TABLE 14-continued

Inhibition of Chimeric Antigen Binding by Fc or Mannan

| | Relative MFI | | | |
|---|---|---|---|---|
| | Mannan | Mouse Fcγ | Mannan & Fcγ | Media |
| 2.5 µg/ml HBV S1/S2-TBD | 21.5 | 2.0 | 3.3 | 22.6 |
| 6 µg/ml HBV S1/S2-TBD | 41.6 | 5.7 | 5.0 | 49.2 |

There was a progressive increase in the binding of the chimeric antigen with its concentration. Incubation of the cells with a high concentration of mouse Fcγ fragment abolished this binding, whereas mannan, an inhibitor of CD206 receptor binding, had only a marginal effect. Therefore, CD32 may be the primary receptor involved in the binding and uptake of the chimeric antigen.

M. Example 13

Glycosylation of HBV S1/S2 Antigen Imparts Immunogenicity

The insect cell pathway of protein glycosylation is different from that of mammalian cells in that proteins synthesized in insect cells undergo glycosylation that results in high mannose content and a lack of terminal sialic acid residues in the secreted protein (Altman, et al., *Glycoconjug* 16:109-123 (1999)). HBV S1/S2, the antigen component of the chimeric antigen was expressed in both *E. coli* (no glycosylation) and in High Five™ insect cells (mannose glycosylation).

1. Effect of Glycosylation on Binding of Antigen

These antigens were compared for their binding to dendritic cells, as described in Example 9. Maturing dendritic cells were loaded with 10 µg/ml of HBV S1/S2 expressed in insect cells or in *E. coli*. Glycosylated protein showed better binding by dendritic cells (Table 15).

TABLE 15

Effect of Glycosylation on Binding of HBV S1/S2

| | % Specific positive cells | Relative MFI |
|---|---|---|
| Insect cells | 69.9 | 40.3 |
| *E. coli* | 12.2 | 3.9 |

2. Effect of Glycosylation on Eliciting Immune Response

Glycosylation of HBV S1/S2 elicits increased immunogenicity and T Cell responses. HBV S1/S2, expressed in both *E. coli* and High Five™ insect cells, were compared for T cell responses when presented by dendritic cells. Both intracellular and secreted interferon-γ levels were measured, as described in Example 8 (using 2.5 µg/ml HBV S1/S2 protein), and the results are presented in Table 16.

TABLE 16

Effect of Glycosylation on Interferon-γ Levels

| | Intracellular IFNγ (% IFNγ positive T cells) | Secreted IFNγ (pg/ml) |
|---|---|---|
| Baculovirus HBV S1/S2 | 2.1 | 18.9 |
| *E. coli* HBV S1/S2 | 0.83 | 4.3 |
| No antigen | 0.77 | 4.4 |
| T cells alone | 0.21 | 1.6 |

HBV S1/S2 expressed in insect cells generated a higher level of both intracellular and secreted interferon, as compared to the unglycosylated protein expressed in *E. coli*.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

What is claimed is:

1. A purified chimeric antigen for eliciting an immune response against Hepatitis B virus (HBV) in a host, wherein the chimeric antigen comprises:
   a polypeptide immune response domain, wherein the immune response domain comprises at least one antigenic portion of an HBV protein selected from the group consisting of HBV S1/S2, HBV S1/S2/S, HBV Core, HBV Core ctm and HBV polymerase;

a polypeptide target binding domain, wherein the target binding domain consists of a hinge region, at least a portion of a $C_H1$ region and a xenotypic Fc antibody fragment comprising at least part of a $C_H2$ and $C_H3$ domain;

wherein the immune response domain and the target binding domain are linked by peptide linkage; and wherein the chimeric antigen is non-mammalian glycoslyated.

2. The chimeric antigen of claim 1, wherein the chimeric antigen comprises more than one immune response domain.

3. The chimeric antigen of claim 1, wherein the target binding domain is capable of binding to an antigen presenting cell.

4. The chimeric antigen of claim 1, wherein the linkage is a covalent peptide linkage.

5. The chimeric antigen of claim 1, which elicits a multi-epitopic immune response.

6. The chimeric antigen of claim 1, which elicits an immune response to at least one epitope of the immune response domain.

7. The chimeric antigen of claim 1, which elicits a humoral immune response.

8. The chimeric antigen of claim 1, which elicits a cellular immune response.

9. The chimeric antigen of claim 1, which elicits a Th1 immune response, a Th2 immune response, a CTL response, or a combination thereof.

10. A pharmaceutical composition comprising a pharmaceutically acceptable excipient and a chimeric antigen of claim 1.

11. The pharmaceutical composition of claim 10, wherein the pharmaceutical composition is formulated for parenteral administration.

12. The pharmaceutical composition of claim 11, wherein the pharmaceutical composition is formulated for transdermal, intradermal, intravenous, subcutaneous, intramuscular, nasal, pulmonary or oral administration.

13. An article of manufacture comprising a chimeric antigen of claim 1 and instructions for administering the chimeric antigen to a subject in need thereof.

14. The chimeric antigen of claim 1, which is recombinantly produced.

15. The chimeric antigen of claim 1, wherein the immune response domain and the target binding domain are produced separately.

16. The chimeric antigen of claim 1, wherein the immune response elicited is greater than that elicited by the immune response domain alone.

17. The chimeric antigen of claim 1, wherein the non-mammalian glycosylation comprises mannose glycosylation.

18. The chimeric antigen of claim 17, wherein the mannose glycosylation comprises high mannose glycosylation.

19. The chimeric antigen of claim 17, wherein the glycosylation comprises pauci mannose glycosylation.

20. The chimeric antigen of claim 1, wherein the non-mammalian glycosylation is an insect cell generated post-translational modification that is capable of binding to a member of the C-type lectin family of endocytic receptors to increase immunogenicity in the host.

21. The chimeric antigen of claim 3, wherein the antigen presenting cell is a dendritic cell.

22. The chimeric antigen of claim 1, wherein the chimeric antigen is capable of binding to an Fc receptor.

23. The chimeric antigen of claim 22, wherein the Fc receptor is selected from the group consisting of CD16, CD32, and CD64.

24. The composition of claim 10, further comprising a nanoparticle.

25. The composition of claim 10, further comprising a nanosphere.

26. The chimeric antigen of claim 1, comprising a monomer comprising:
a polypeptide immune response domain wherein the immune response domain comprises at least one antigenic portion of an HBV protein selected from the group consisting of HBV S1/S2, HBV S1/S2/S, HBV Core, HBV Core ctm and HBV polymerase;
and a polypeptide target binding domain, wherein the target binding domain consists of a hinge region, at least a portion of a $C_H1$ region and a xenotypic Fc antibody fragment comprising at least part of a $C_H2$ and $C_H3$ domain.

27. The chimeric antigen of claim 1, comprising a dimer of a monomer comprising:
a polypeptide immune response domain wherein the immune response domain comprises at least one antigenic portion of an HBV protein selected from the group consisting of HBV S1/S2, HBV S1/S2/S, HBV Core, HBV Core ctm and HBV polymerase;
and a polypeptide target binding domain, wherein the target binding domain consists of a hinge region, at least a portion of a $C_H1$ region and a xenotypic Fc antibody fragment comprising at least part of a $C_H2$ and $C_H3$ domain.

28. The chimeric antigen of claim 20, wherein the member of the C-type lectin family of endocytic receptors is a macrophage mannose receptor.

29. The chimeric antigen of claim 1, wherein at least one of the immune response domain and target binding domain are non-mammalian glycosylated.

* * * * *